United States Patent
Olson et al.

(10) Patent No.: US 6,919,307 B2
(45) Date of Patent: Jul. 19, 2005

(54) THERAPEUTIC AGENTS AND METHODS OF USE THEREOF FOR THE MODULATION OF ANGIOGENESIS

(75) Inventors: Gary L. Olson, Mountainside, NJ (US); Christopher Self, West Caldwell, NJ (US); Lily Lee, Edison, NJ (US); Charles Michael Cook, Mendham, NJ (US); Jens Birktoft, New York, NY (US)

(73) Assignee: Praecis Pharmaceuticals, Inc., Waltham, MA (US)

( * ) Notice: Subject to any disclaimer, the term of this patent is extended or adjusted under 35 U.S.C. 154(b) by 0 days.

(21) Appl. No.: 10/138,935

(22) Filed: May 2, 2002

(65) Prior Publication Data

US 2003/0109671 A1 Jun. 12, 2003

Related U.S. Application Data

(63) Continuation-in-part of application No. 10/001,945, filed on Nov. 1, 2001, which is a continuation-in-part of application No. 09/972,772, filed on Oct. 5, 2001, which is a continuation-in-part of application No. 09/704,251, filed on Nov. 1, 2000, now Pat. No. 6,548,477.

(51) Int. Cl.[7] ...................... A61K 31/336; A61K 38/08
(52) U.S. Cl. ............................ 514/2; 514/16; 514/475; 514/478; 514/588
(58) Field of Search .................. 514/2, 16, 255.01, 514/315, 317, 326, 428, 475, 478, 588; 530/300, 329, 350; 544/386, 391; 546/224, 244; 548/567; 549/332; 560/157, 159; 564/32

(56) References Cited

U.S. PATENT DOCUMENTS

| | | | | |
|---|---|---|---|---|
| 5,180,735 A | | 1/1993 | Kishimoto et al. | 514/443 |
| 5,422,363 A | * | 6/1995 | Yanai et al. | 514/410 |
| 6,017,954 A | * | 1/2000 | Folkman et al. | 514/475 |
| 6,086,865 A | * | 7/2000 | Folkman et al. | 424/85.1 |
| 6,548,477 B1 | * | 4/2003 | Olson et al. | 514/2 |
| 2002/0151493 A1 | * | 10/2002 | Olson et al. | 514/12 |
| 2002/0193298 A1 | * | 12/2002 | Olson et al. | 514/12 |

FOREIGN PATENT DOCUMENTS

EP  658342 B1  3/1999

OTHER PUBLICATIONS

Griffith EC, et al. "Molecular recognition of angiogenesis inhibitors fumagillin and ovalicin by methionine aminopeptidase 2." *Proc Natl Acad Sci U S A.* Dec. 22, 1998;95(26):15183–8.

Zhang et al. "Angiogenesis inhibitors specific for methionine aminopeptidase 2 as drugs for malaria and *Leishmaniasis.*" *J. Biomed Sci.* 2002;9:34–40.

* cited by examiner

Primary Examiner—Jeffrey Edwin Russel
(74) Attorney, Agent, or Firm—Lahive & Cockfield, LLP; Giulio A. DeConti, Jr.; Maria Laccotripe Zacharakis

(57) ABSTRACT

The present invention provides methods of treating a parasitic infection, a lymphoid malignancy or an autoimmune disorder in a subject by administering to the subject a therapeutically effective amount of an angiogenesis inhibitor compound comprising a MetAP-2 inhibitory core coupled to a peptide.

53 Claims, 2 Drawing Sheets

SEQUENCE LISTING

<160> NUMBER OF SEQ ID NOS: 40

<210> SEQ ID NO 1
<211> LENGTH: 4
<212> TYPE: PRT
<213> ORGANISM: Artificial Sequence
<220> FEATURE:
<221> NAME/KEY: VARIANT
<222> LOCATION: 4
<223> OTHER INFORMATION: Xaa = amino acid
<220> FEATURE:
<223> OTHER INFORMATION: Description of Artificial Sequence: Motif

<400> SEQUENCE: 1

Pro Leu Gly Xaa
  1

<210> SEQ ID NO 2
<211> LENGTH: 5
<212> TYPE: PRT
<213> ORGANISM: Artificial Sequence
<220> FEATURE:
<221> NAME/KEY: VARIANT
<222> LOCATION: 2
<223> OTHER INFORMATION: Xaa represents L-cyclohexylalanine
<220> FEATURE:
<221> NAME/KEY: VARIANT
<222> LOCATION: 4
<223> OTHER INFORMATION: Xaa represents methylated cysteine
<220> FEATURE:
<223> OTHER INFORMATION: Description of Artificial Sequence: Motif

<400> SEQUENCE: 2

Pro Xaa Gly Xaa His
  1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 8
<223> OTHER INFORMATION: Xaa represents D-Arginine

<400> SEQUENCE: 3

Pro Gln Gly Ile Ala Gly Gln Xaa
  1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 4

Pro Gln Gly Ile Ala Gly Trp
  1               5

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Motif

```
<220> FEATURE:
<221> NAME/KEY: VARIANT
<222> LOCATION: 4
<223> OTHER INFORMATION: Xaa represents methylated cysteine
<220> FEATURE:
<221> NAME/KEY: VARIANT
<222> LOCATION: 7
<223> OTHER INFORMATION: Xaa represents D-Arginine

<400> SEQUENCE: 5

Pro Leu Gly Xaa His Ala Xaa
  1               5

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 7
<223> OTHER INFORMATION: Xaa represents D-Arginine

<400> SEQUENCE: 6

Pro Leu Gly Leu Trp Ala Xaa
  1               5

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 7

Pro Leu Ala Leu Trp Ala Arg
  1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 8

Pro Leu Ala Leu Trp Ala Arg
  1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 9

Pro Leu Ala Tyr Trp Ala Arg
  1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 10
```

```
Pro Tyr Ala Tyr Trp Met Arg
 1               5
```

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 2
<223> OTHER INFORMATION: Xaa represents L-cyclohexylalanine
<220> FEATURE:
<221> NAME/KEY: VARIANT
<222> LOCATION: 4
<223> OTHER INFORMATION: Xaa represents L-norvaline

<400> SEQUENCE: 11

```
Pro Xaa Gly Xaa His Ala
 1               5
```

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 4
<223> OTHER INFORMATION: Xaa represents L-norvaline

<400> SEQUENCE: 12

```
Pro Leu Ala Xaa
 1
```

<210> SEQ ID NO 13
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 13

```
Pro Leu Gly Leu
 1
```

<210> SEQ ID NO 14
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 14

```
Pro Leu Gly Ala
 1
```

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Motif

<400> SEQUENCE: 15

```
Arg Pro Leu Ala Leu Trp Arg Ser
```

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 2
<223> OTHER INFORMATION: Xaa represents L-cyclohexylalanine
<220> FEATURE:
<221> NAME/KEY: VARIANT
<222> LOCATION: 4
<223> OTHER INFORMATION: Xaa represents L-a-aminobutyryl
<220> FEATURE:
<221> NAME/KEY: VARIANT
<222> LOCATION: 5
<223> OTHER INFORMATION: Xaa represents methylated cysteine

<400> SEQUENCE: 16

Pro Xaa Ala Xaa Xaa His Ala
 1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 2
<223> OTHER INFORMATION: Xaa represents L-cyclohexylalanine
<220> FEATURE:
<221> NAME/KEY: VARIANT
<222> LOCATION: 5
<223> OTHER INFORMATION: Xaa represents methylated cysteine

<400> SEQUENCE: 17

Pro Xaa Ala Gly Xaa His Ala
 1               5

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Motif

<400> SEQUENCE: 18

Pro Lys Pro Gln Gln Phe Phe Gly Leu
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 19

Pro Lys Pro Leu Ala Leu
 1               5

<210> SEQ ID NO 20
<211> LENGTH: 9
<212> TYPE: PRT
<213> ORGANISM: Artificial Sequence

```
<220> FEATURE:
<223> OTHER INFORMATION: Description of Artificial Sequence: Motif
<220> FEATURE:
<221> NAME/KEY: VARIANT
<222> LOCATION: 7
<223> OTHER INFORMATION: Xaa represents L-norvaline

<400> SEQUENCE: 20

Arg Pro Lys Pro Tyr Ala Xaa Trp Met
 1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 7
<223> OTHER INFORMATION: Xaa represents L-norvaline

<400> SEQUENCE: 21

Arg Pro Lys Pro Val Glu Xaa Trp Arg
 1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 7
<223> OTHER INFORMATION: Xaa represents L-norvaline

<400> SEQUENCE: 22

Arg Pro Lys Pro Val Glu Xaa Trp Arg
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 7
<223> OTHER INFORMATION: Xaa represents L-norvaline

<400> SEQUENCE: 23

Arg Pro Lys Pro Leu Ala Xaa Trp
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 1
<223> OTHER INFORMATION: Xaa represents a modified Proline residue
      having an acetyl group attached

<400> SEQUENCE: 24

Xaa Leu Gly Met Trp Ala
```

```
                1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Motif

<400> SEQUENCE: 25

Gly Pro Leu Gly Met His Ala Gly
  1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 4
<223> OTHER INFORMATION: Xaa represents methylated glycine

<400> SEQUENCE: 26

Gly Pro Leu Xaa
  1

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 27

Gly Pro Leu Gly
  1

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Motif

<400> SEQUENCE: 28

Gly Met Gly Leu Pro
  1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Motif

<400> SEQUENCE: 29

Ala Met Gly Ile Pro
  1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Motif
<220> FEATURE:
```

```
<221> NAME/KEY: VARIANT
<222> LOCATION: 4
<223> OTHER INFORMATION: Xaa represents a modified tyrosine residue
      having an O-Methyl group attached

<400> SEQUENCE: 30

Arg Gly Asp Xaa Arg Glu
  1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence: Motif

<400> SEQUENCE: 31

Gly Arg Gly Asp Ser Pro
  1               5

<210> SEQ ID NO 32
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 32

Gly Arg Gly Asp
  1

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 1
<223> OTHER INFORMATION: Xaa represents a modified Proline residue
      having an acetyl group attached

<400> SEQUENCE: 33

Xaa Leu Gly Met Ala
  1               5

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: VARIANT
<222> LOCATION: 1
<223> OTHER INFORMATION: Xaa represents a modified Arginine residue
      having an acetyl group attached

<400> SEQUENCE: 34

Xaa Gly Asp Ser Pro Leu Gly Met Trp Ala
  1               5                  10

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Motif
```

```
<400> SEQUENCE: 35

Pro Leu Gly Met Trp Ser Arg
 1               5

<210> SEQ ID NO 36
<211> LENGTH: 5
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: VARIANT
<222> LOCATION: 1
<223> OTHER INFORMATION: Xaa represents a modified Proline residue
      having an acetyl group attached

<400> SEQUENCE: 36

Xaa Leu Gly Met Gly
 1               5

<210> SEQ ID NO 37
<211> LENGTH: 3
<212> TYPE: PRT
<213> ORGANISM: Artificial Sequence
<220> FEATURE:
<223> OTHER INFORMATION: Description of Artificial Sequence: Peptide

<400> SEQUENCE: 37

Met Trp Ala
 1

<210> SEQ ID NO 38
<211> LENGTH: 2
<212> TYPE: PRT
<213> ORGANISM: Artificial Sequence
<220> FEATURE:
<223> OTHER INFORMATION: Description of Artificial Sequence: Peptide

<400> SEQUENCE: 38

Met Gly
 1

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Peptide

<400> SEQUENCE: 39

Gly Pro Leu Gly Met Trp Ala Gly
 1               5

<210> SEQ ID NO 40
<211> LENGTH: 3
<212> TYPE: PRT
<213> ORGANISM: Artificial Sequence
<220> FEATURE:
<223> OTHER INFORMATION: Description of Artificial Sequence: Peptide
<220> FEATURE:
<221> NAME/KEY: VARIANT
```

```
-continued

<222> LOCATION: 3
<223> OTHER INFORMATION: Xaa represents 3-amino-3-pyridylpropionic acid

<400> SEQUENCE: 40

Gly Arg Xaa
 1
```

THERAPEUTIC AGENTS AND METHODS OF USE THEREOF FOR THE MODULATION OF ANGIOGENESIS

RELATED APPLICATIONS

This application is a continuation-in-part of U.S. patent application Ser. No. 10/001,945, filed Nov. 1, 2001, pending; which in turn is a continuation-in-part of U.S. patent application Ser. No. 09/972,772, filed Oct. 5, 2001, pending; which in turn is a continuation-in-part of U.S. patent application Ser. No. 09/704,251, filed Nov. 1, 2000, which issued on Apr. 15, 2003 as U.S. Pat. No. 6,548,477 B1. The entire contents of each of the aforementioned applications are hereby incorporated by reference.

BACKGROUND OF THE INVENTION

Angiogenesis is the fundamental process by which new blood vessels are formed and is essential to a variety of normal body activities (such as reproduction, development and wound repair). Although the process is not completely understood, it is believed to involve a complex interplay of molecules which both stimulate and inhibit the growth of endothelial cells, the primary cells of the capillary blood vessels. Under normal conditions, these molecules appear to maintain the microvasculature in a quiescent state (i.e., one of no capillary growth) for prolonged periods which may last for as long as weeks or in some cases, decades. When necessary, however, (such as during wound repair), these same cells can undergo rapid proliferation and turnover within a 5 day period (Folkman, J. and Shing, Y., *Journal of Biological Chemistry*, 267(16): 10931–10934, and Folkman, J. and Klagsbrun, M. (1987) *Science*, 235: 442–447).

Although angiogenesis is a highly regulated process under normal conditions, many diseases (characterized as "angiogenic diseases") are driven by persistent unregulated angiogenesis. Otherwise stated, unregulated angiogenesis may either cause a particular disease directly or exacerbate an existing pathological condition. For example, ocular neovacularization has been implicated as the most common cause of blindness and dominates approximately 20 eye diseases. In certain existing conditions such as arthritis, newly formed capillary blood vessels invade the joints and destroy cartilage. In diabetes, new capillaries formed in the retina invade the vitreous, bleed, and cause blindness. Growth and metastasis of solid tumors are also angiogenesis-dependent (Folkman, J. (1986) *Cancer Research* 46: 467–473 and Folkman, J. (1989) *Journal of the National Cancer Institute* 82: 4–6). It has been shown, for example, that tumors which enlarge to greater than 2 mm, must obtain their own blood supply and do so by inducing the growth of new capillary blood vessels. Once these new blood vessels become embedded in the tumor, they provide a means for tumor cells to enter the circulation and metastasize to distant sites, such as the liver, lung or bone (Weidner, N., et al (1991) *The New England Journal of medicine* 324(1):1–8).

Fumagillin is a known compound which has been used as an antimicrobial and antiprotozoal. Its physicochemical properties and method of production are well known (U.S. Pat. No. 2,803,586 and *Proc. Nat. Acad. Sci. USA* (1962) 48:733–735). Fumagillin and certain types of Fumagillin analogs have also been reported to exhibit anti-angiogenic activity. However, the use of such inhibitors (e.g., TNP-470) may be limited by their rapid metabolic degradation, erratic blood levels, and by dose-limiting central nervous system (CNS) side effects.

Accordingly, there is still a need for angiogenesis inhibitors which are more potent, less neurotoxic, more stable, and/or have longer serum half-lives.

SUMMARY OF THE INVENTION

The present invention provides angiogenesis inhibitor compounds which comprise a core, e.g., a Fumagillin core, that is believed to inhibit methionine aminopeptidase 2 (MetAP-2), coupled to a peptide. The present invention is based, at least in part, on the discovery that coupling the MetAP-2 inhibitory core to an amino acid residue or an amino acid derivative prevents the metabolic degradation of the angiogenesis inhibitor compound to ensure a superior pharmacokinetic profile and limits CNS side effects by altering the ability of the angiogenesis inhibitor compound to cross the blood brain barrier. The present invention is also based, at least in part, on the discovery that coupling the MetAP-2 inhibitory core to a peptide comprising a site-directed sequence allows for a cell specific delivery of the angiogenesis inhibitor compound and limits the toxicity of the angiogenesis inhibitor compound.

Accordingly, the present invention provides compounds of Formula I,

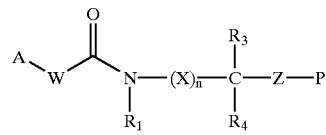

In Formula I, A is a MetAP-2 inhibitory core, W is O or $NR_2$, and $R_1$ and $R_2$ are each, independently, hydrogen or alkyl; X is alkylene or substituted alkylene, preferably linear $C_1$–$C_6$-alkylene; n is 0 or 1; $R_3$ and $R_4$ are each, independently, hydrogen, substituted or unsubstituted alkyl, substituted or unsubstituted aryl or arylalkyl or substituted or unsubstituted heteroaryl or heteroalkyl. $R_3$ and $R_4$ can also, together with the carbon atom to which they are attached, form a carbocyclic or heterocyclic group; or $R_1$ and $R_4$ together can form an alkylene group; Z is —C(O)—, alkylene-C(O)— or alkylene; and P is a peptide comprising from 1 to about 100 amino acid residues attached at its amino terminus to Z or a group $OR_5$ or $N(R_6)R_7$, wherein $R_5$, $R_6$ and $R_7$ are each, independently, hydrogen, alkyl, substituted alkyl, azacycloalkyl or substituted azacycloalkyl. $R_6$ and $R_7$ can also form, together with the nitrogen atom to which they are attached, a substituted or unsubstituted heterocyclic ring structure.

In another embodiment of the compounds of Formula I, W, X, n, $R_1$, $R_3$ and $R_4$ have the meanings given above for these variables; Z is —O—, —$NR_8$—, alkylene-O— or alkylene-$NR_8$—, where $R_8$ is hydrogen or alkyl; and P is hydrogen, alkyl, preferably normal or branched $C_1$–$C_4$-alkyl or a peptide consisting of from 1 to about 100 amino acid residues attached at its carboxy terminus to Z.

In compounds of Formula I, when any of $R_1$–$R_8$ is an alkyl group, preferred alkyl groups are substituted or unsubstituted normal, branched or cyclic $C_1$–$C_6$ alkyl groups. Particularly preferred alkyl groups are normal or branched $C_1$–$C_4$ alkyl groups. A substituted alkyl group includes at least one non-hydrogen substituent, such as an amino group, an alkylamino group or a dialkylamino group; a halogen, such as a fluoro, chloro, bromo or iodo substituent; or hydroxyl.

When at least one of $R_3$ and $R_4$ is a substituted or unsubstituted aryl or heteroaryl group, preferred groups include substituted and unsubstituted phenyl, naphthyl, indolyl, imidazoly and pyridyl. When at least one of $R_3$ and $R_4$ is substituted or unsubstituted arylalkyl or heteroarylalkyl, preferred groups include substituted and unsubstituted benzyl, naphthylmethyl, indolylmethyl, imidazolylmethyl and pyridylmethyl groups. Preferred substituents on aryl, heteroaryl, arylalkyl and heteroarylalkyl groups are independently selected from the group consisting of amino, alkyl-substituted amino, halogens, such as fluoro, chloro, bromo and iodo; hydroxyl groups and alkyl groups, preferably normal or branched $C_1$–$C_6$-alkyl groups, most preferably methyl groups. X is preferably linear $C_1$–$C_6$-alkylene, more preferably $C_1$–$C_4$-alkylene and most preferably methylene or ethylene. When Z is alkylene-C(O)—, alkylene-O— or alkylene-$NR_8$, the alkylene group is preferably linear $C_1$–$C_6$-alkylene, more preferably $C_1$–$C_4$-alkylene and most preferably methylene or ethylene.

$R_6$ and $R_7$, in addition to alkyl, substituted alkyl or hydrogen, can each also independently be a substituted or unsubstituted azacycloalkyl group or a substituted or unsubstituted azacycloalkylalkyl group. Suitable substituted azacycloalkyl groups include azacycloalkyl groups which have an N-alkyl substituent, preferably an N—$C_1$–$C_4$-alkyl substituent and more preferably an N-methyl substituent. $R_6$ and $R_7$ can also, together with the nitrogen atom to which they are attached, form a heterocyclic ring system, such as a substituted or unsubstituted five or six-membered aza- or diazacycloalkyl group. Preferably, the diazacycloalkyl group includes an N-alkyl substituent, such as an N—$C_1$–$C_4$-alkyl substituent or, more preferably, an N-methyl substituent.

In particularly preferred embodiments, —N($R_6$)$R_7$ is $NH_2$ or one of the groups shown below:

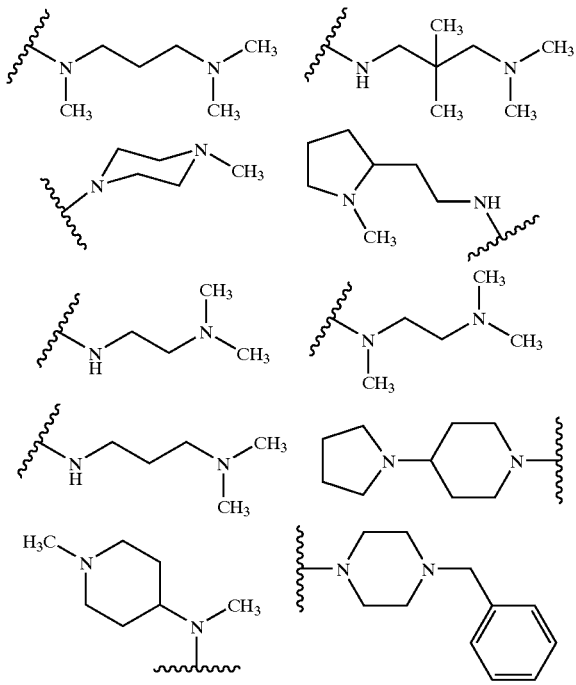

Preferably, the compounds of Formula I do not include compounds wherein Z is —O—, P is hydrogen, $R_3$ and $R_4$ are both hydrogen, n is 1 and X is methylene. Preferably, the compounds of Formula I further do not include compounds wherein Z is methylene-O—, $R_3$ and $R_4$ are both hydrogen, and n is 0.

In another aspect, the present invention is directed to angiogenesis inhibitor compounds of Formula XV,

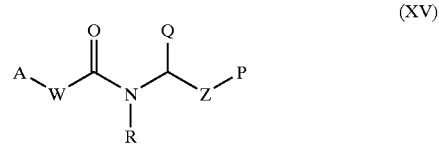

(XV)

where A is a MetAP-2 inhibitory core and W is O or NR. In one embodiment, Z is —C(O)— or -alkylene-C(O)— and P is NHR, OR or a peptide consisting of one to about one hundred amino acid residues connected at the N-terminus to Z. In this embodiment, Q is hydrogen, linear, branched or cyclic alkyl or aryl, provided that when P is —OR, Q is not hydrogen.

In another embodiment, Z is -alkylene-O— or -alkylene-N(R)— and P is hydrogen or a peptide consisting of from one to about one hundred amino acid residues connected to Z at the carboxyl terminus. In this embodiment, Q is hydrogen, linear, branched or cyclic alkyl or aryl, provided that when P is hydrogen, Q is not hydrogen.

In the angiogenesis inhibitor compounds of Formula XV, each R is, independently, hydrogen or alkyl.

In another aspect, the invention features pharmaceutical compositions comprising the angiogenesis inhibitor compounds of Formula I or XV and a pharmaceutically acceptable carrier.

In yet another aspect, the invention features a method of treating an angiogenic disease, e.g., cancer (such as lung cancer, brain cancer, kidney cancer, colon cancer, liver cancer, pancreatic cancer, stomach cancer, prostate cancer, breast cancer, ovarian cancer, cervical cancer, melanoma, and metastatic versions of any of the preceding cancers), in a subject. The method includes administering to the subject a therapeutically effective amount of one or more angiogenesis inhibitor compounds of Formula I or XV.

In one embodiment, the present invention provides a method of treating a subject suffering from a parasitic infection, such as an infection by *Plasmodium* species, such as *Plasmodium falciparum*, or an infection by *Leishmania* species, such as *Leishmania donavani*. The method comprises the step of administering to the subject a therapeutically effective amount of a compound of the invention. The subject can be an individual who is suffering from, or susceptible to, infection by a parasitic organism. In a preferred embodiment, the subject suffers from malaria or *Leishmaniasis*.

The invention further provides a method of treating a subject suffering from a lymphoid malignancy. The method comprises the step of administering to the subject a therapeutically effective amount of a compound of the invention. Suitable lymphoid malignancies which can be treated with a compound of the invention include lymphoid leukemias, such as chronic lymphoid leukemia and acute lymphoid leukemia, and lymphomas, such as T cell lymphoma and B cell lymphoma.

In a further embodiment, the invention provides a method of treating a subject suffering from an autoimmune disorder, comprising the step of administering to the subject a therapeutically effective amount of a compound of the invention. The autoimmune disorder can be, for example, rheumatoid arthritis, lupus erytlematosus, psoriasis, multiple sclerosis, myasthenia gravis, vasculitis, or diabetes mellitus.

Other features and advantages of the invention will be apparent from the following detailed description and claims.

DETAILED DESCRIPTION OF THE INVENTION

Figure 1:
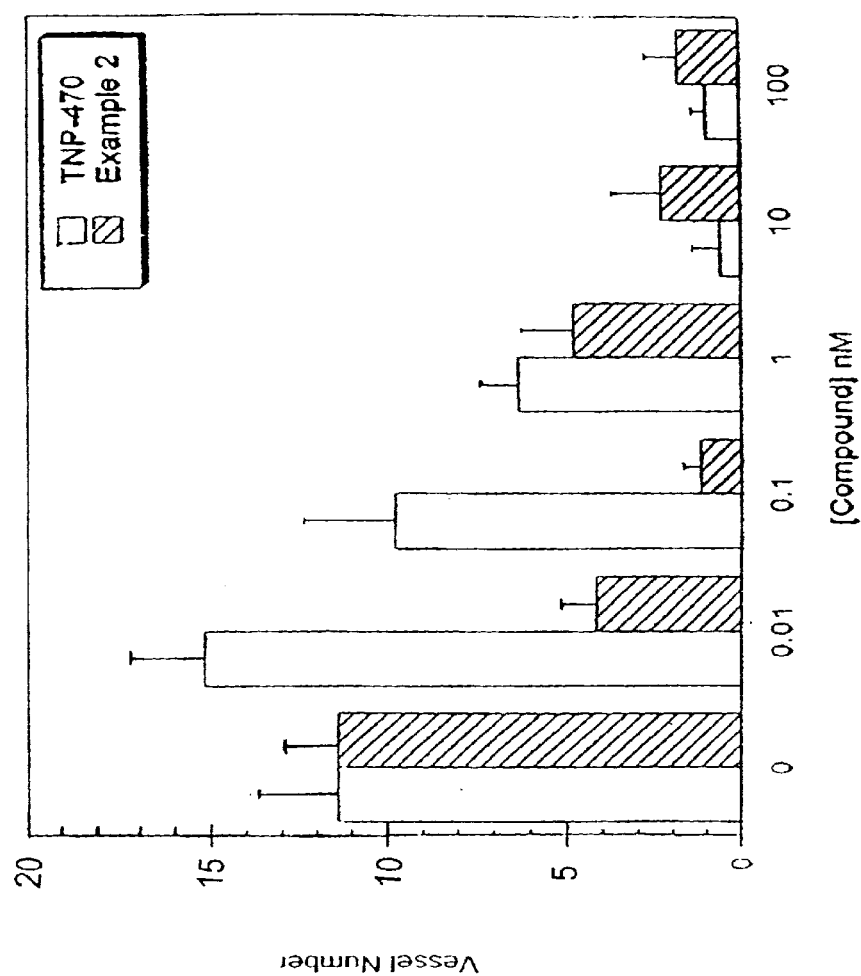
FIG. 1 is a graph depicting the results from the rat aortic ring assay (RARA) used to test the ability of the angiogenesis inhibitor compounds of the invention to inhibit angiogenesis.

The present invention provides compounds useful as angiogenesis inhibitors and methods for using these compounds in the treatment of angiogenic diseases. Without intending to be limited by theory, it is believed that the angiogenesis inhibitor compounds of the invention inhibit angiogenesis by inhibiting methionine aminopeptidase 2 (MetAP-2), an enzyme which cleaves the N-terminal methionine residue of newly synthesized proteins to produce the active form of the protein. At the same time, the presence of a peptide in the angiogenesis inhibitor compounds of the invention prevents the metabolic degradation of the angiogenesis inhibitor compounds and ensures a superior pharmacokinetic profile. The presence of the peptide in the angiogenesis inhibitor compounds of the invention also alters the ability of the angiogenesis inhibitor compound to cross the blood brain barrier to, for example, limit CNS side effects (such as CNS toxicity). The presence of peptides comprising a site-directed sequence in the angiogenesis inhibitor compounds of the invention allows for a site-specific delivery of the angiogenesis inhibitor compounds and, thus, limits the toxicity of the angiogenesis inhibitor compounds.

The angiogenesis inhibitor compounds of the invention comprise a MetAP-2 inhibitory core and a peptide attached, directly or indirectly, thereto. In one embodiment, the invention provides angiogenesis inhibitor compounds of Formula I

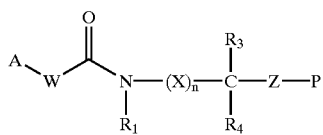

In Formula I, A is a MetAP-2 inhibitory core, W is O or $NR_2$, and $R_1$ and $R_2$ are each, independently, hydrogen or alkyl; X is alkylene or substituted alkylene, preferably linear $C_1$–$C_6$-alkylene; n is 0 or 1; $R_3$ and $R_4$ are each, independently, hydrogen, substituted or unsubstituted alkyl, substituted or unsubstituted aryl or arylalkyl or substituted or unsubstituted heteroaryl or heteroalkyl. $R_3$ and $R_4$ can also, together with the carbon atom to which they are attached, form a carbocyclic or heterocyclic group; or $R_1$ and $R_4$ together can form an alkylene group; Z is —C(O)—, alkylene-C(O)— or alkylene; and P is a peptide comprising from 1 to about 100 amino acid residues attached at its amino terminus to Z or a group $OR_5$ or $N(R_6)R_7$, wherein $R_5$, $R_6$ and $R_7$ are each, independently, hydrogen, alkyl, substituted alkyl, azacycloalkyl or substituted azacycloalkyl. $R_6$ and $R_7$ can also form, together with the nitrogen atom to which they are attached, a substituted or unsubstituted heterocyclic ring structure.

In another embodiment of the compounds of Formula I, W, X, n, $R_1$, $R_3$ and $R_4$ have the meanings given above for these variables; Z is —O—, —$NR_8$—, alkylene-O— or alkylene-$NR_8$—, where $R_8$ is hydrogen or alkyl; and P is hydrogen, alkyl, preferably normal or branched $C_1$–$C_4$-alkyl or a peptide consisting of from 1 to about 100 amino acid residues attached at its carboxy terminus to Z.

In compounds of Formula I, when any of $R_1$–$R_8$ is an alkyl group, preferred alkyl groups are substituted or unsubstituted normal, branched or cyclic $C_1$–$C_6$ alkyl groups. Particularly preferred alkyl groups are normal or branched $C_1$–$C_4$ alkyl groups. A substituted alkyl group includes at least one non-hydrogen substituent, such as an amino group, an alkylamino group or a dialkylamino group; a halogen, such as a fluoro, chloro, bromo or iodo substituent; or hydroxyl.

When at least one of $R_3$ and $R_4$ is a substituted or unsubstituted aryl or heteroaryl group, preferred groups include substituted and unsubstituted phenyl, naphthyl, indolyl, imidazolyl and pyridyl. When at least one of $R_3$ and $R_4$ is substituted or unsubstituted arylalkyl or heteroarylalkyl, preferred groups include substituted and unsubstituted benzyl, naphthyhnethyl, indolylmethyl, imidazolyhnethyl and pyridylmethyl groups. Preferred substituents on aryl, heteroaryl, arylalkyl and heteroarylalkyl groups are independently selected from the group consisting of amino, alkyl-substituted amino, halogens, such as fluoro, chloro, bromo and iodo; hydroxyl groups and alkyl groups, preferably normal or branched $C_1$–$C_6$-alkyl groups, most preferably methyl groups. X is preferably linear $C_1$–$C_6$-alkylene, more preferably $C_1$–$C_4$-alkylene and most preferably methylene or ethylene. When Z is alkylene-C(O)—, alkylene-O— or alkylene-$NR_8$, the alkylene group is preferably linear $C_1$–$C_6$-alkylene, more preferably $C_1$–$C_4$-alkylene and most preferably methylene or ethylene.

$R_6$ and $R_7$, in addition to alkyl, substituted alkyl or hydrogen, can each also independently be a substituted or unsubstituted azacycloalkyl group or a substituted or unsubstituted azacycloalkylalkyl group. Suitable substituted azacycloalkyl groups include azacycloalkyl groups which have an N-alkyl substituent, preferably an N—$C_1$–$C_4$-alkyl substituent and more preferably an N-methyl substituent. $R_6$ and $R_7$ can also, together with the nitrogen atom to which they are attached, form a heterocyclic ring system, such as a substituted or unsubstituted five or six-membered aza- or diazacycloalkyl group. Preferably, the diazacycloalkyl group includes an N-alkyl substituent, such as an N—$C_1$–$C_4$-alkyl substituent or, more preferably, an N-methyl substituent.

In particularly preferred embodiments, —$N(R_6)R_7$ is $NH_2$ or one of the groups shown below:

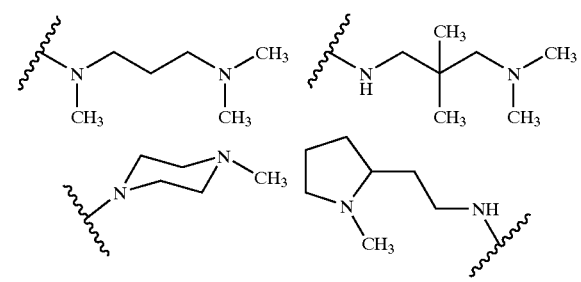

Preferably, the compounds of Formula I do not include compounds wherein Z is

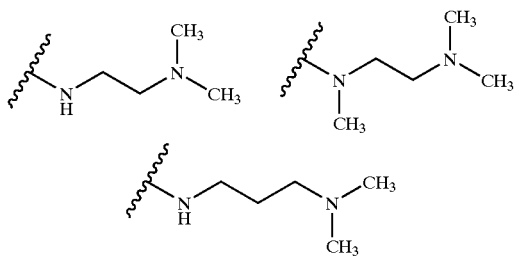

—O—, P is hydrogen, $R_3$ and $R_4$ are both hydrogen, n is 1 and X is methylene. Preferably, the compounds of Formula I further do not include compounds wherein Z is methylene-O—, $R_3$ and $R_4$ are both hydrogen, and n is 0.

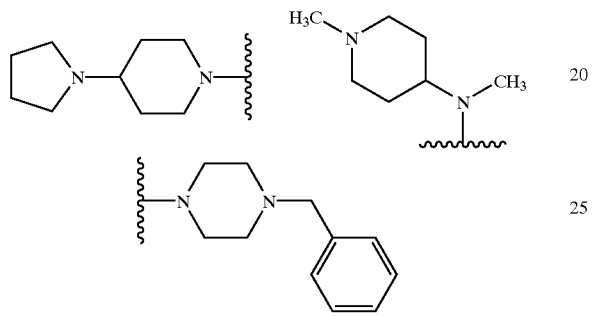

In another embodiment, the invention provides angiogenesis inhibitor compounds of Formula XV,

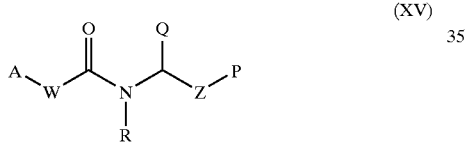

(XV)

where A is a MetAP-2 inhibitory core and W is O or NR. In one embodiment, Z is —C(O)— or -alkylene-C(O)— and P is NhR, OR or a peptide consisting of one to about one hundred amino acid residues connected at the N-terminus to Z. In this embodiment, Q is hydrogen, linear, branched or cyclic alkyl or aryl, provided that when P is —OR, Q is not hydrogen. Z is preferably —C(O)— or $C_1$–$C_4$-alkylene-C(O)—, and, more preferably, —C(O)— or $C_1$–$C_2$-alkylene-C(O)—. Q is preferably linear, branched or cyclic $C_1$–$C_6$-alkyl, phenyl or naphthyl. More preferably, Q is isopropyl, phenyl or cyclohexyl.

In another embodiment, Z is -alkylene-O— or -alkylene-N(R)—, where alkylene is, preferably, $C_1$–$C_6$-alkylene, more preferably $C_1$–$C_4$-alkylene and, most preferably, $C_1$–$C_2$-alkylene. P is hydrogen or a peptide consisting of from one to about one hundred amino acid residues connected to Z at the carboxyl terminus. In this embodiment, Q is hydrogen, linear, branched or cyclic alkyl or aryl, provided that when P is hydrogen, Q is not hydrogen. Q is preferably linear, branched or cyclic $C_1$–$C_6$-alkyl, phenyl or naphthyl. More preferably, Q is isopropyl, phenyl or cyclohexyl.

In the compounds of Formula XV, each R is, independently, hydrogen or alkyl. In one embodiment, each R is, independently, hydrogen or linear, branched or cyclic $C_1$–$C_6$-alkyl. Preferably, each R is, independently, hydrogen or linear or branched $C_1$–$C_4$-alkyl. More preferably, each R is, independently, hydrogen or methyl. In the most preferred embodiments, each R is hydrogen.

In Formulas I and XV, A is a MetAP-2 inhibitory core. As used herein, a "MetAP-2 inhibitory core" includes a moiety able to inhibit the activity of methionine aminopeptidase 2 (MetAP-2), e.g., the ability of MetAP-2 to cleave the N-terminal methionine residue of newly synthesized proteins to produce the active form of the protein. Preferred MetAP-2 inhibitory cores are Fumagillin derived structures.

Suitable MetAP-2 inhibitory cores include the cores of Formula II,

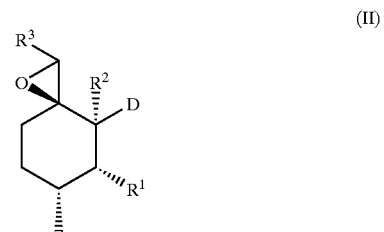

(II)

where $R^1$ is hydrogen or alkoxy, preferably $C_1$–$C_4$-alkoxy and more preferably, methoxy. $R^2$ is hydrogen or hydroxy; and $R^3$ is hydrogen or alkyl, preferably $C_1$–$C_4$-alkyl and more preferably, hydrogen. D is linear or branched alkyl, preferably $C_1$–$C_6$-alkyl; arylalkyl, preferably aryl-$C_1$–$C_4$-alkyl and more preferably phenyl-$C_1$–$C_4$-alkyl; or D is of the structure

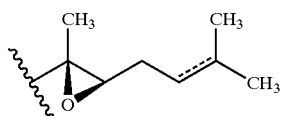

where the dashed line represents a single bond or a double bond.

A can also be a MetAP-2 inhibitory core of Formula III,

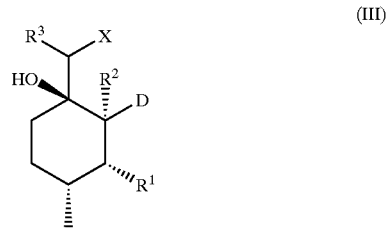

(III)

Where $R^1$, $R^2$, $R^3$ and D have the meanings given above for Formula II, and X is a leaving group, such as a halogen.

Examples of suitable MetAP-2 inhibitory cores include, but are not limited to, the following.

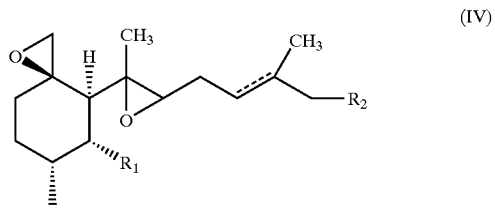

(IV)

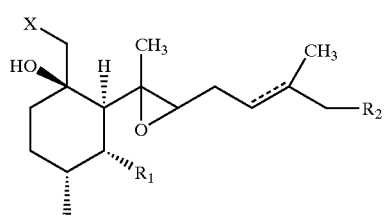
(V)

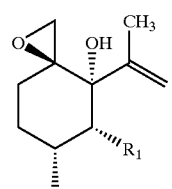
(VI)

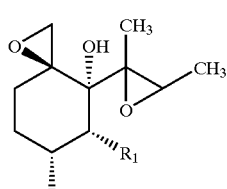
(VII)

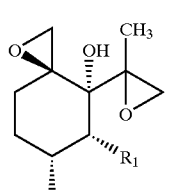
(VIII)

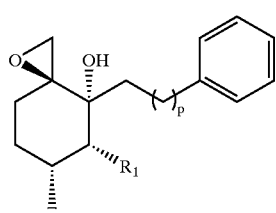
(IX)

In each of Formulas IV–X, the indicated valence on the ring carbon is the point of attachment of the structural variable W, as set forth in Formulas I–XV. In Formula IX, p is an integer from 0 to 10, preferably 1–4. In Formulas IV, V and VI–IX, $R_1$ is hydrogen or $C_1$–$C_4$-alkoxy, preferably methoxy. In Formulas IV and V, the dashed line indicates that the bond can be a double bond or a single bond. In Formula V, X represents a leaving group, such as a thioalkoxy group, a thioaryloxy group, a halogen or a dialkylsulfinium group. In Formulas IV and V, $R_2$ is H, OH, amino, $C_1$–$C_4$-alkylamino or di($C_1$–$C_4$-alkyl)amino), preferably H. In formulas in which the stereochemistry of a particular stereocenter is not indicated, that stereocenter can have either of the possible stereochemistries, consistent with the ability of the angiogenesis inhibitor compound to inhibit the activity of MetAP-2.

In particularly preferred embodiments, A is the MetAP-2 inhibitory core of Formula X below.

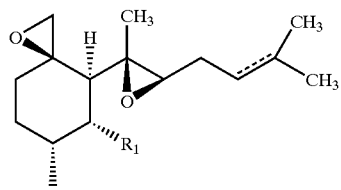
(X)

As used herein, the terms "P" and "peptide" include compounds comprising from 1 to about 100 amino acid residues (e.g., 1, 2, 3, 4, 5, 6, 7, 8, 9, 10, 11, 12, 13, 14, 15, 16, 17, 18, 19, 20 or more amino acid residues). In preferred embodiments, the peptide includes compounds comprising less than about 90, 80, 70, 60, 50, 40, 30, 20, or 10 amino acid residues, preferably about 1–10, 1–20, 1–30, 1–40, 1–50, 1–60, 1–70, 1–80 or 1–90 amino acid residues. The peptides may be natural or synthetically made. The amino acid residues are preferably a-amino acid residues. For example, the amino acid residues can be independently selected from among the twenty naturally occurring amino acid residues, the D-enantiomers of the twenty natural amino acid residues, and may also be non-natural amino acid residues (e.g., norleucine, norvaline, phenylglycine, β-alanine, or a peptide mimetic such as 3-amino-methylbenzoic acid). In one embodiment, the amino acid residues are independently selected from residues of Formula XI, Formula XII, and Formula XIII.

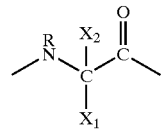
XI

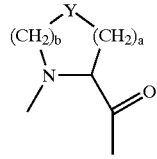
XII

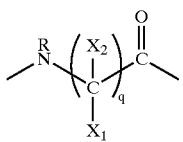
XIII

In Formula XI, $X_1$ is hydrogen, a side chain of one of the twenty naturally-occurring amino acid residues, a linear, branched or cyclic $C_1$–$C_8$-alkyl group, an aryl group, such as a phenyl or naphthyl group, an aryl-$C_1$–$C_4$-alkyl group, a heteroaryl group, such as a pyridyl, thienyl, pyrrolyl, or furyl group, or a heteroaryl-$C_1$–$C_4$-alkyl group; and $X_2$ is hydrogen a linear, branched or cyclic $C_1$–$C_8$-alkyl group, an aryl group, such as a phenyl or naphthyl group, an aryl-$C_1$–$C_4$-alkyl group or a heteroaryl group as described above for $X_1$. Preferably, $X_2$ is hydrogen. In Formula XII, Y is methylene, oxygen, sulfur or NH, and a and b are each, independently, 0–4, provided that the sum of a and b is between 1 and 4. Formulas XI and XII encompass α-amino acid residues having either a D or an L stereochemistry at the alpha carbon atom. One or more of the amino acid residues can also be an amino acid residue other than an a-amino acid residue, such as a β-, γ- or ϵ-amino acid residue. Suitable examples of such amino acid residues are of Formula XIII, wherein q is an integer of from 2 to about 6, and each $X_1$ and $X_2$ independently have the meanings given above for these variables in Formula XI.

In a preferred embodiment, the peptide used in the angiogenesis inhibitor compounds of the invention may include a site-directed sequence in order to increase the specificity of binding of the angiogenesis inhibitor compound to a cell surface of interest. As used herein, the term "site-directed sequence" is intended to include any amino acid sequence (e.g., comprised of natural or non natural amino acid residues) which serves to limit exposure of the angiogenesis inhibitor compound to the periphery and/or which serves to direct the angiogenesis inhibitor compound to a site of interest, e.g., a site of angiogenesis or aberrant cellular proliferation.

The peptide contained within the angiogenesis inhibitor compounds of the invention may include a peptide cleavage site for an enzyme which is expressed at sites of angiogenesis or aberrant cell proliferation, allowing tissue-selective delivery of a cell-permeable active angiogenesis inhibitor compound or fragment thereof (e.g., a fragment containing the MetAP-2 inhibitory core of the angiogenesis inhibitor compound). The peptide may also include a sequence which is a ligand for a cell surface receptor which is expressed at a site of angiogenesis or aberrant cell proliferation, thereby targeting angiogenesis inhibitor compounds to a cell surface of interest. For example, a peptide contained within the angiogenesis inhibitor compounds of the invention can include a cleavage site for a matrix metalloproteinase, or an integrin binding RGD (Arg-Gly-Asp) sequence, or a combination of both an enzyme "cleavage" sequence and a cell surface "ligand" which serve to target the angiogenesis inhibitor compound to the membrane of an endothelial cell. However, the selection of a peptide sequence must be such that the active angiogenesis inhibitor compound is available to be delivered to the cells in which MetAP-2 inhibition is desired.

For example, a sequence that is cleaved by a matrix matalloproteinase produces a product that contains the MetAP-2 inhibitory core, a coupling group, and a peptide fragment. Sequences are selected so that the active angiogenesis inhibitor compound, e.g., the active angiogenesis inhibitor compound generated by the matrix matalloproteinase cleavage, is cell permeable. Preferably, the active angiogenesis inhibitor compound does not contain a free acid after the cleavage.

In one embodiment, the peptide includes a cleavage site for a matrix metalloprotease, such as matrix metalloprotease-2 (MMP-2), MMP-1, MMP-3, MMP-7, MMP-8, MMP-9, MMP-12, MMP-13 or MMP-26. Preferably, the peptide includes a cleavage site for MMP-2 or MMP-9. For example, the peptide can comprise the sequence -Pro-Leu-Gly-Xaa-(SEQ ID NO:1), where Xaa is any naturally occurring amino acid residue consistent with matrix metalloprotease (MMP) cleavage at the Gly-Xaa bond. Xaa is preferably a hydrophobic amino acid residue, such as tryptophan, phenylalanine, methionine, leucine, isoleucine, proline, and valine.

Other suitable sequences include sequences comprising one or more of Pro-Cha-Gly-Cys(Me)-His (SEQ ID NO:2); Pro-Gln-Gly-Ile-Ala-Gly-Gln-D-Arg (SEQ ID NO:3); Pro-Gln-Gly-Ile-Ala-Gly-Trp (SEQ ID NO:4); Pro-Leu-Gly-Cys (Me)-His-Ala-D-Arg (SEQ ID NO:5); Pro-Leu-Gly-Met-Trp-Ser-Arg (SEQ ID NO:35); Pro-Leu-Gly-Leu-Trp-Ala-D-Arg (SEQ ID NO:6); Pro-Leu-Ala-Leu-Trp-Ala-Arg (SEQ ID NO:7); Pro-Leu-Ala-Leu-Trp-Ala-Arg (SEQ ID NO:8); Pro-Leu-Ala-Tyr-Trp-Ala-Arg (SEQ ID NO:9); Pro-Tyr-Ala-Tyr-Trp-Met-Arg (SEQ ID NO:10); Pro-Cha-Gly-Nva-His-Ala (SEQ ID NO:11); Pro-Leu-Ala-Nva (SEQ ID NO:12); Pro-Leu-Gly-Leu (SEQ ID NO:13); Pro-Leu-Gly-Ala (SEQ ID NO:14); Arg-Pro-Leu-Ala-Leu-Trp-Arg-Ser (SEQ ID NO:15); Pro-Cha-Ala-Abu-Cys(Me)-His-Ala (SEQ ID NO:16); Pro-Cha-Ala-Gly-Cys(Me)-His-Ala (SEQ ID NO:17); Pro-Lys-Pro-Gln-Gln-Phe-Phe-Gly-Leu (SEQ ID NO:18); Pro-Lys-Pro-Leu-Ala-Leu (SEQ ID NO:19); Arg-Pro-Lys-Pro-Tyr-Ala-Nva-Trp-Met (SEQ ID NO:20); Arg-Pro-Lys-Pro-Val-Glu-Nva-Trp-Arg (SEQ ID NO:21); Arg-Pro-Lys-Pro-Val-Glu-Nva-Trp-Arg (SEQ ID NO:22); and Arg-Pro-Lys-Pro-Leu-Ala-Nva-Trp (SEQ ID NO:23). These sequences identify the natural amino acid residues using the customary three-letter abbreviations; the following abbreviations represent the indicated non-natural amino acids: Abu=L-a-aminobutyryl; Cha=L-cyclohexylalanine; Nva=L-norvaline.

In certain embodiments, P is an amino acid sequence selected from the group consisting of Ac-Pro-Leu-Gly-Met-Trp-Ala (SEQ ID NO:24); Gly-Pro-Leu-Gly-Met-His-Ala-Gly (SEQ ID NO:25); Gly-Pro-Leu-(Me)Gly (SEQ ID NO:26); Gly-Pro-Leu-Gly (SEQ ID NO:27); Gly-Met-Gly-Leu-Pro (SEQ ID NO:28); Ala-Met-Gly-Ile-Pro (SEQ ID NO:29); Gly-Arg-Gly-Asp-(O-Me-Tyr)-Arg-Glu (SEQ ID NO:30); Gly-Arg-Gly-Asp-Ser-Pro (SEQ ID NO:31); Gly-Arg-Gly-Asp (SEQ ID NO:32); Asp-Gly-Arg; Ac-Pro-Leu-Gly-Met-Ala (SEQ ID NO:33); Ac-Arg-Gly-Asp-Ser-Pro-Leu-Gly-Met-Trp-Ala (SEQ ID NO:34); Ac-Pro-Leu-Gly-Met-Gly (SEQ ID NO:36); Met-Trp-Ala (SEQ ID NO:37); Met-Gly (SEQ ID NO:38); Gly-Pro-Leu-Gly-Met-Trp-Ala-Gly (SEQ ID NO:39); and Gly-Arg-(3-amino-3-pyridylpropionic acid) (SEQ ID NO:40). (Ac in the foregoing sequences represents an Acetyl group).

The peptide can be attached to the MetAP-2 inhibitory core at either its N-terminus or C-terminus. When the peptide is attached to the MetAP-2 inhibitory core at its C-terminus, the N-terminus of the peptide can be —$NR_2R_3$, where $R_2$ is hydrogen, alkyl or arylalkyl and $R_3$ is hydrogen, alkyl, arylalkyl or acyl. When the peptide is attached to the MetAP-2 inhibitory core at its N-terminus, the C-terminus can be —$C(O)R_4$, where $R_4$ is —OH, —O-alkyl, —O-arylalkyl, or —$NR_2R_3$, where $R_2$ is hydrogen, alkyl or arylalkyl and $R_3$ is hydrogen, alkyl, arylalkyl or acyl. In this embodiment, the C-terminal residue can also be present in a reduced form, such as the corresponding primary alcohol.

The present invention also includes pharmaceutically acceptable salts of the angiogenesis inhibitor compounds of the invention. A "pharmaceutically acceptable salt" includes a salt that retains the desired biological activity of the parent angiogenesis inhibitor compound and does not impart any undesired toxicological effects. Examples of such salts are salts of acids such as hydrochloric acid, hydrobromic acid, sulfuric acid, phosporic acid, nitric acid, and the like; acetic acid, oxalic acid, tartaric acid, succinic acid, malic acid, benzoic acid, pamoic acid, alginic acid, methanesulfonic acid, naphthalenesulfonic acid, and the like. Also included are salts of cations such as sodium, potassium, lithium, zinc, copper, barium, bismuth, calcium, and the like; or organic cations such as trialkylammonium. Combinations of the above salts are also useful.

Preferred Angiogenesis Inhibitor Compounds of Formula I

One set of particularly preferred angiogenesis inhibitor compounds of the invention includes compounds in which A is the MetAP-2 inhibitory core of Formula X, W is O or $NR_2$, and the structure

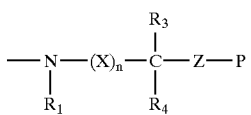
is represented by the structures set forth below.
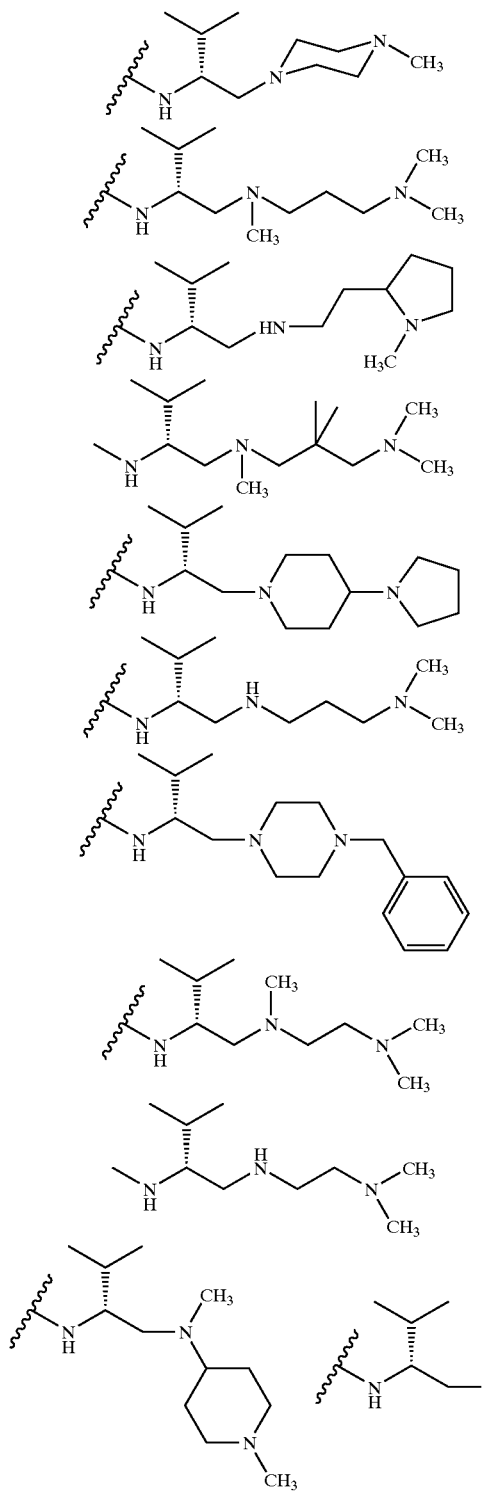
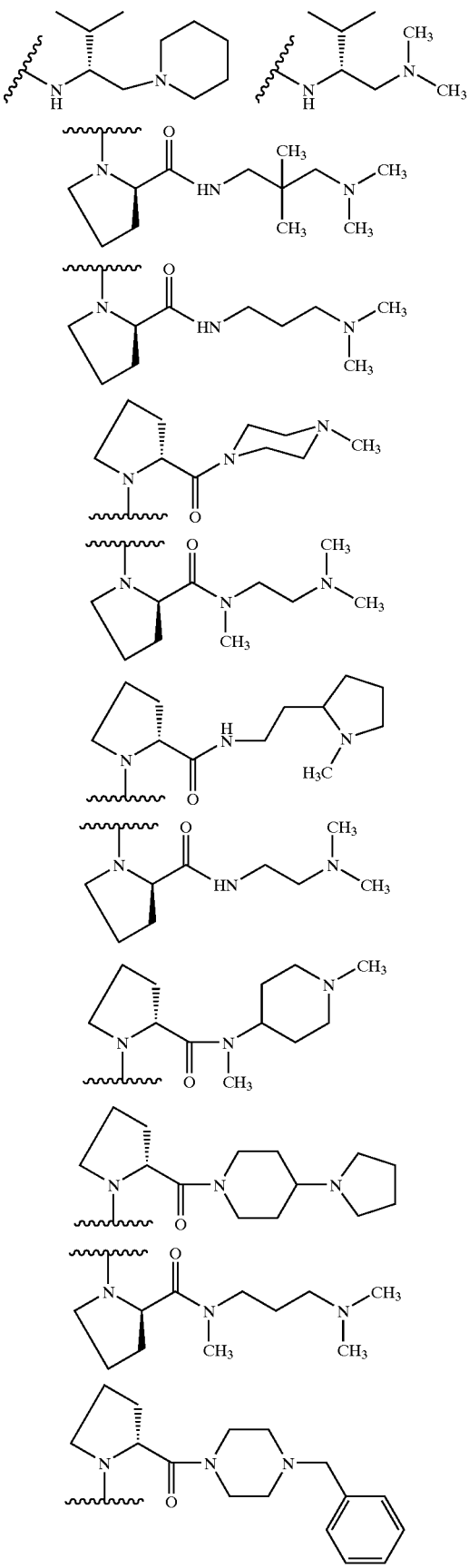

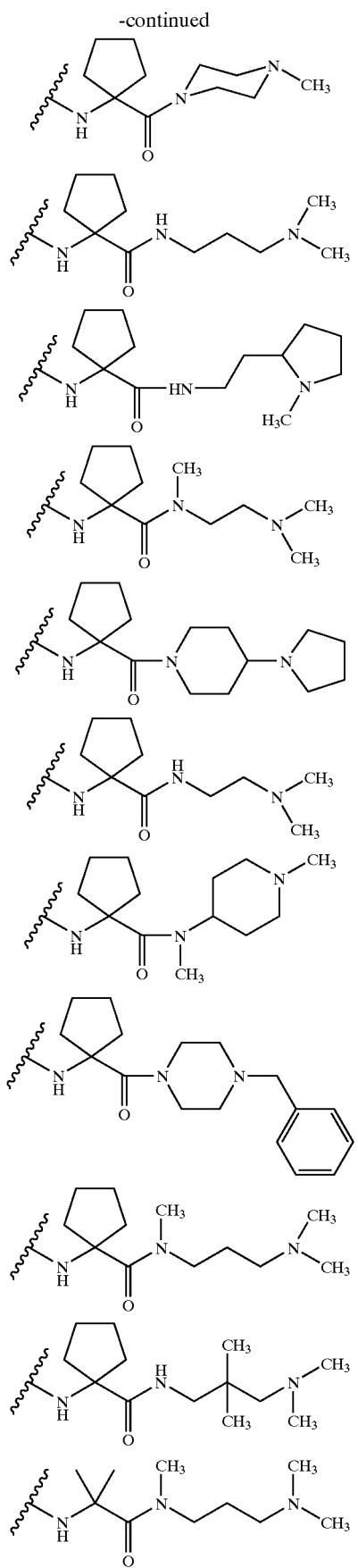
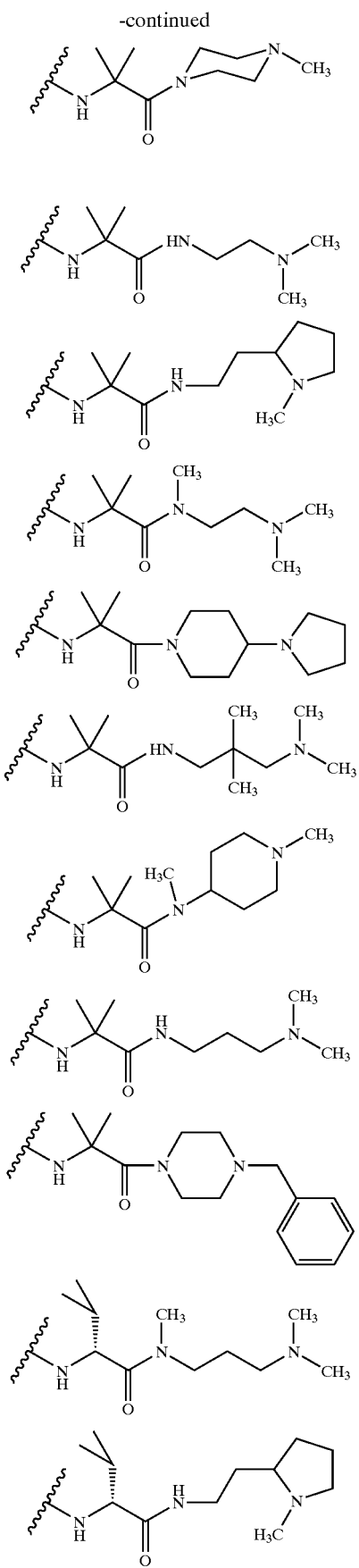

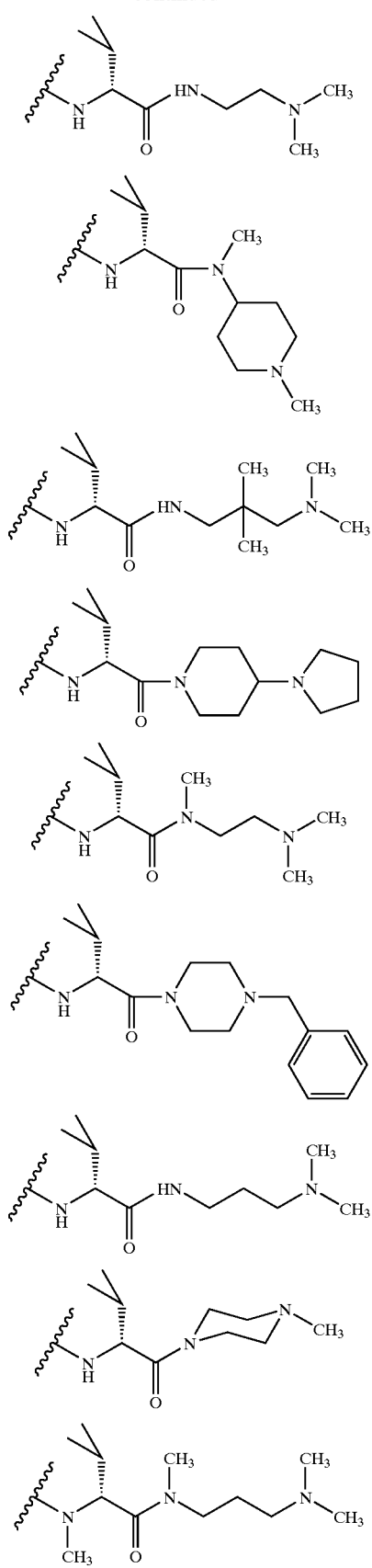
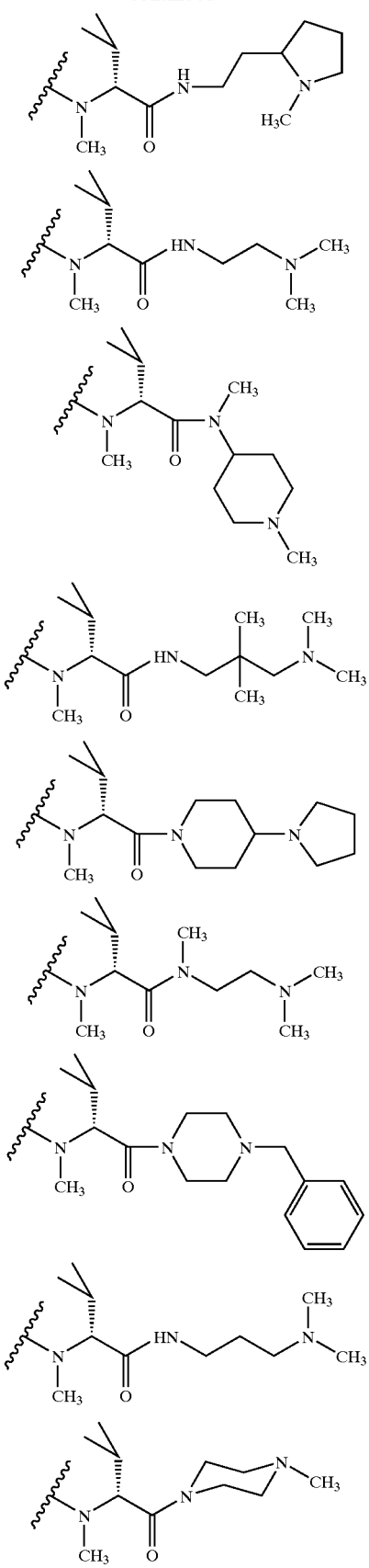

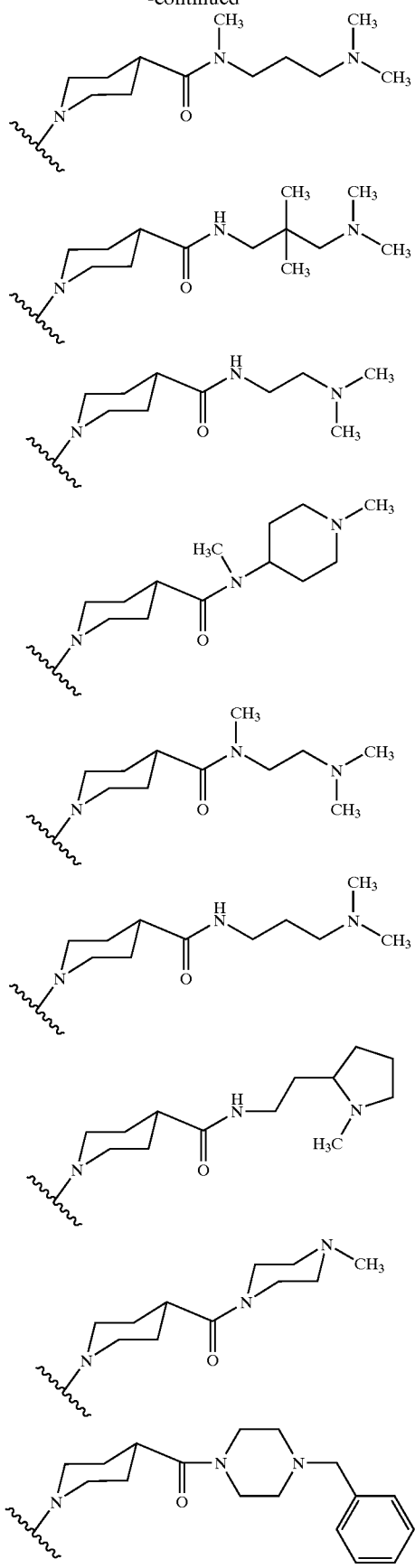
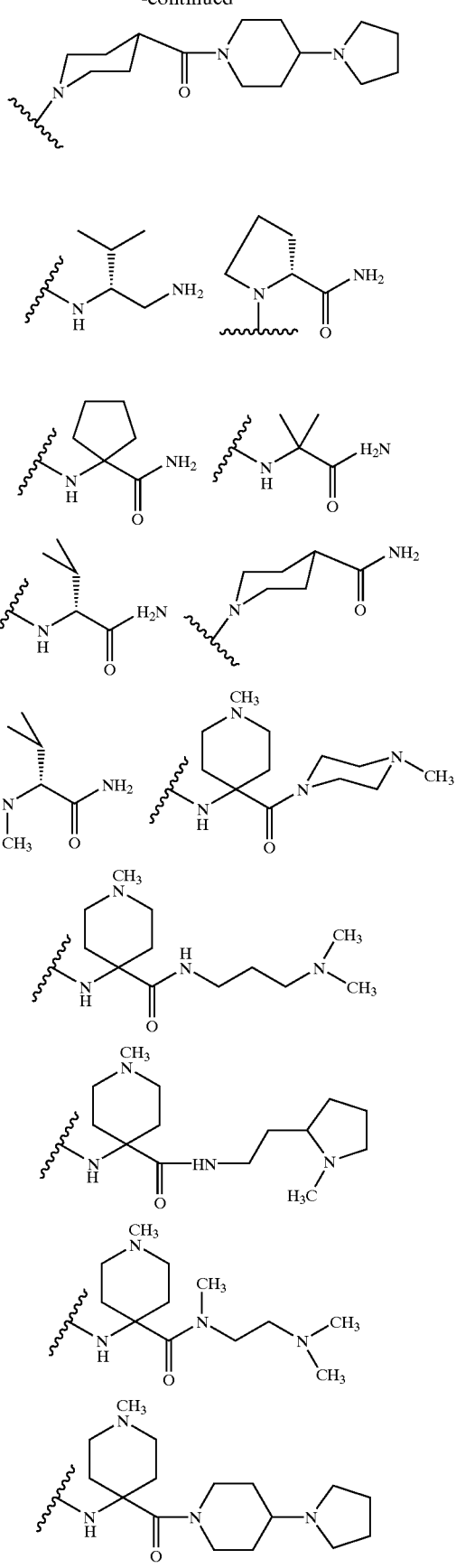

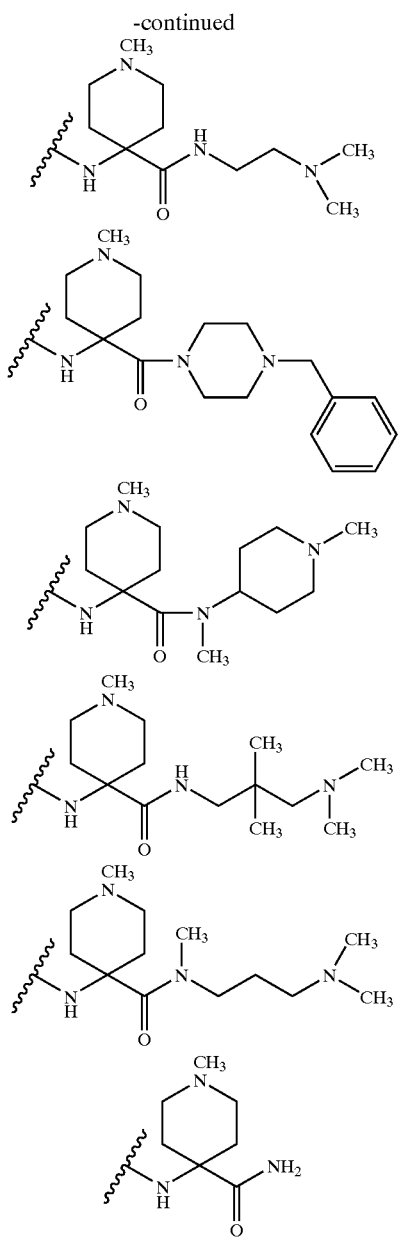

Preferred Angiogenesis Inhibitor Compounds of Formula XV

A preferred subset of the angiogenesis inhibitor compounds of Formula XV comprises Formula XIV shown below.

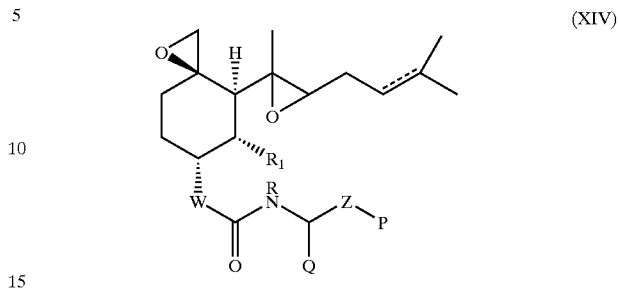

(XIV)

In one embodiment, W is O or NR. Z is —C(O) or -alkylene-C(O)—, preferably $C_1$–$C_4$-alkylene-C(O)—. R is hydrogen or a $C_1$–$C_4$-alkyl. Q is hydrogen; linear, branched or cyclic $C_1$–$C_6$-alkyl; or aryl. $R_1$ is hydroxy, $C_1$–$C_4$-alkoxy or halogen. P is $NH_2$, OR or a peptide attached to Z at its N-terminus and comprising from 1 to 100 amino acid residues independently selected from naturally occurring amino acid residues, D-enantiomers of the naturally occurring amino acid residues and non-natural amino acid residues. When Q is H, P is not NH2 or OR. In preferred embodiments, W is O or NH; Q is isopropyl; $R_1$ is methoxy; P comprises from 1 to 15 amino acid residues; and the dashed line present in Formula XIV represents a double bond. In particularly preferred embodiments, W is O, and P comprises 10 or fewer amino acid residues.

In another embodiment of the compounds of Formula XIV, W is O or NR. Z is alkylene-O or alkylene-NR, preferably C1–C4-alkylene-O or C1–C4-alkylene-NR—. R is hydrogen or a $C_1$–$C_4$-alkyl. Q is hydrogen; linear, branched or cyclic $C_1$–$C_6$-alkyl; or aryl. $R_1$ is hydroxy, $C_1$–$C_4$-alkoxy or halogen. P is hydrogen or a peptide attached to Z at its C-terminus and comprising from 1 to 100 amino acid residues independently selected from naturally occurring amino acid residues, D-enantiomers of the naturally occurring amino acid residues and non-natural amino acid residues. When Q is H, P is not H. In preferred embodiments, W is O or NH; Q is isopropyl; $R_1$ is methoxy; P comprises from 1 to 15 amino acid residues; and the dashed line present in Formula XIV represents a double bond. In particularly preferred embodiments, W is O, and P comprises 10 or fewer amino acid residues or P is hydrogen.

One set of particularly preferred angiogenesis inhibitor compounds of the invention is represented by the structures set forth below.

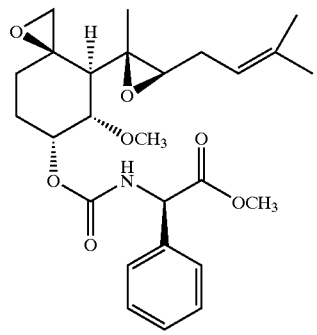
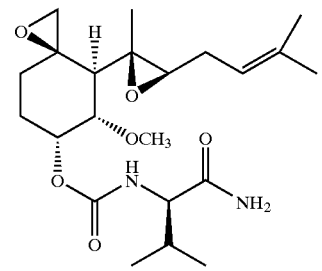

-continued
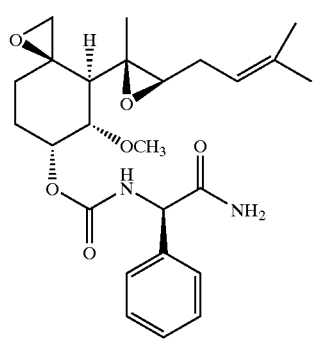
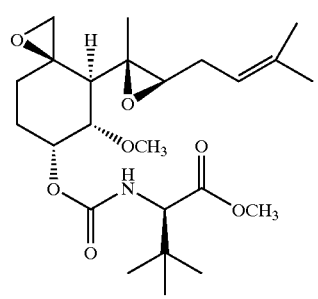
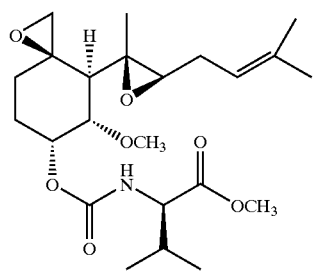
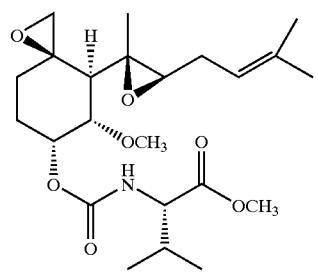
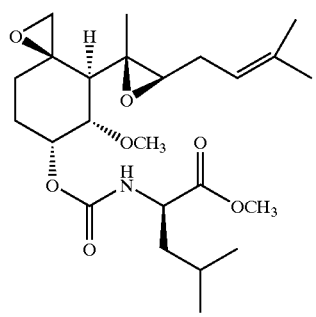
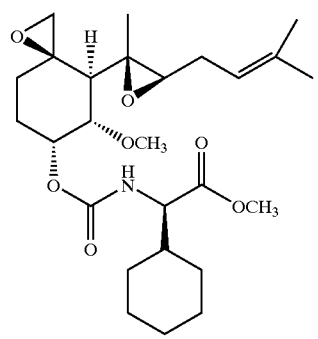
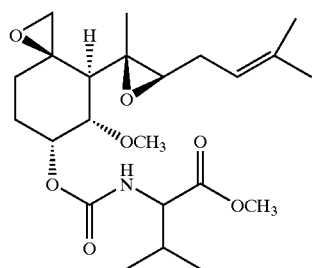
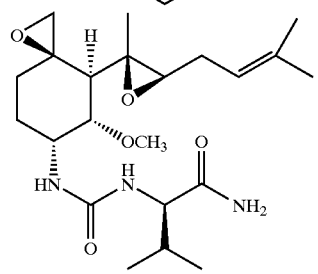
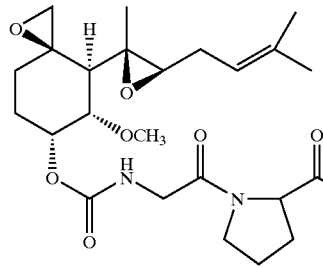
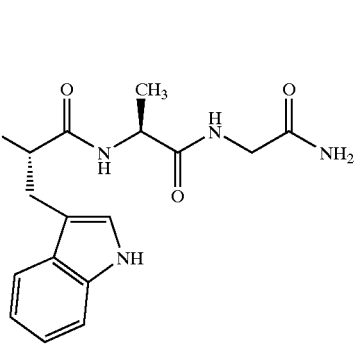

-continued
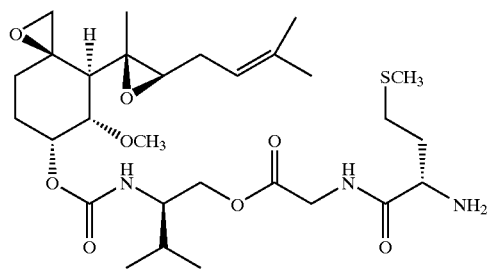
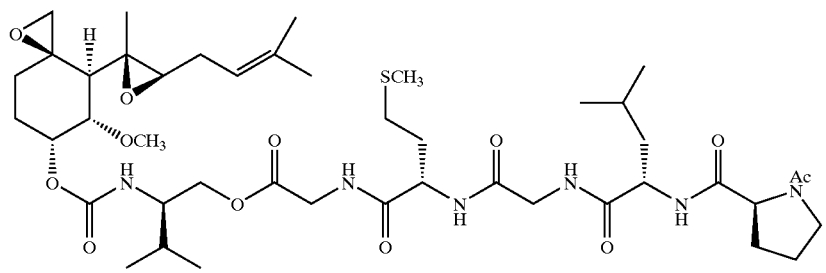
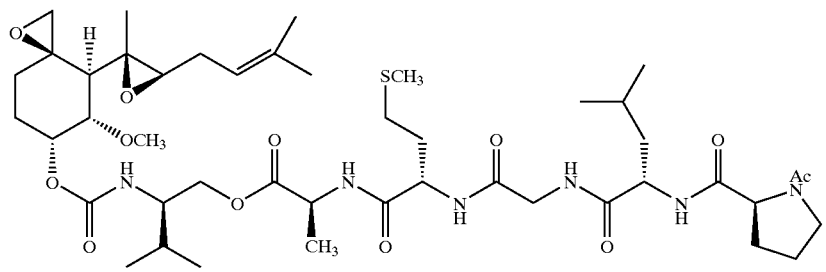
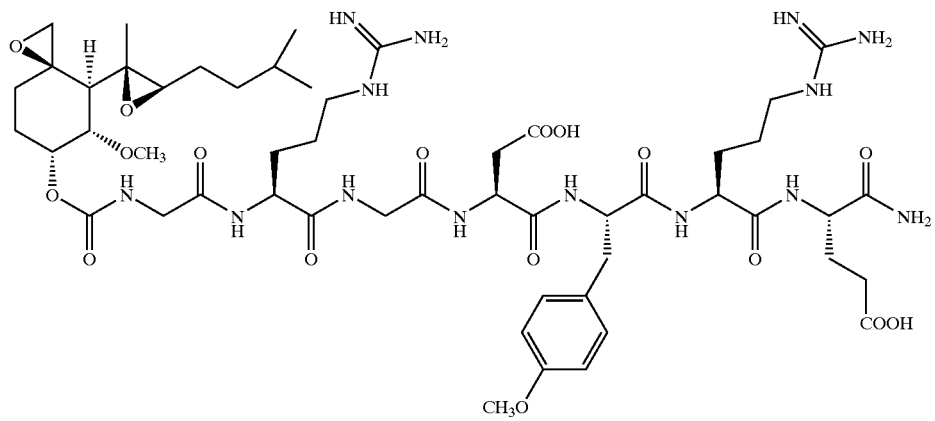
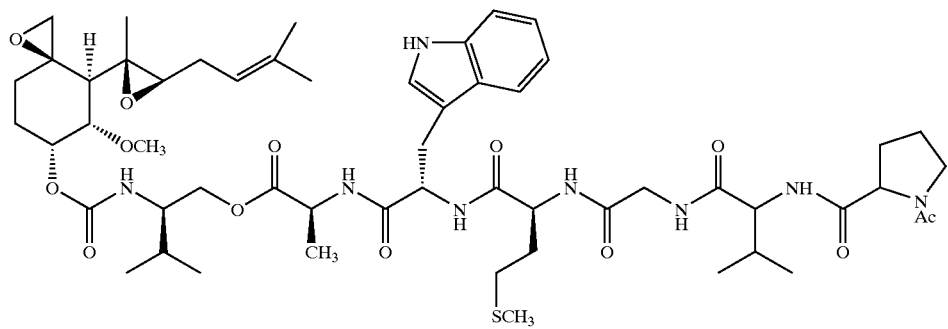

-continued
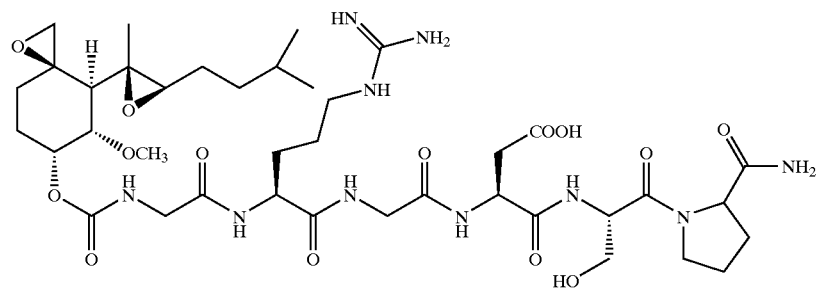
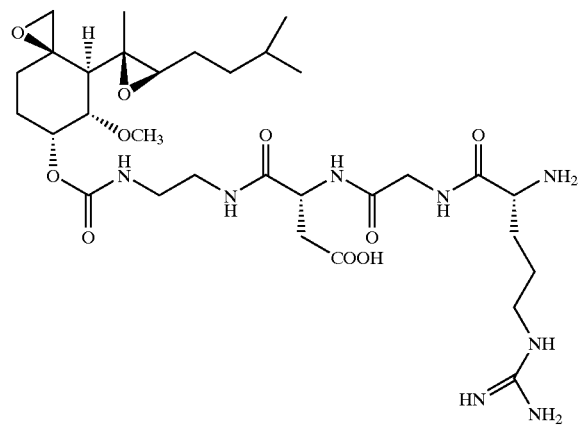
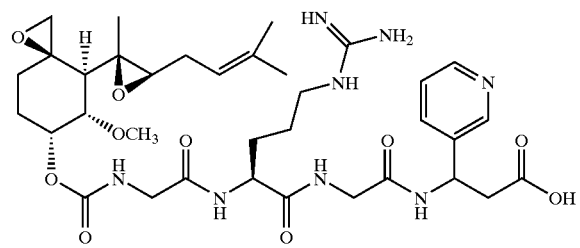
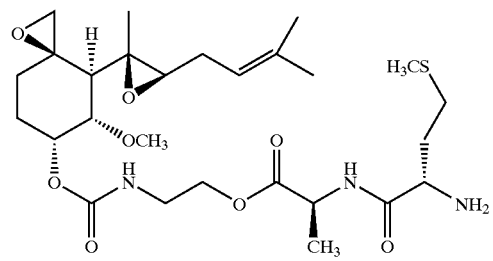
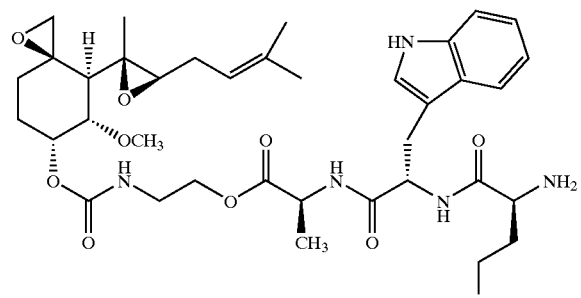
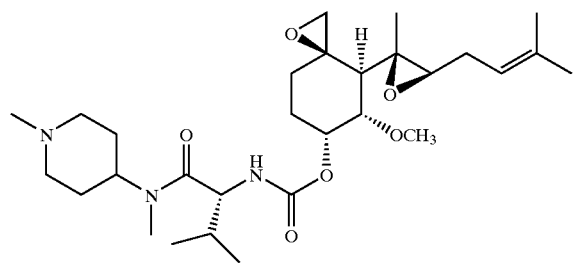
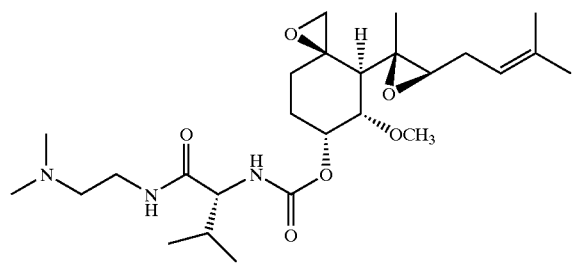
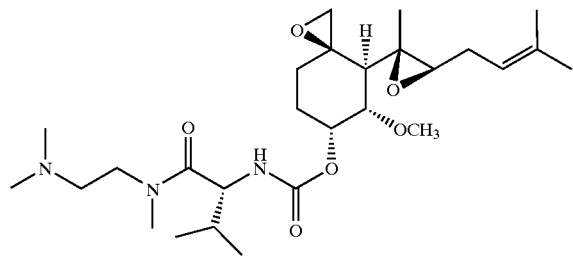
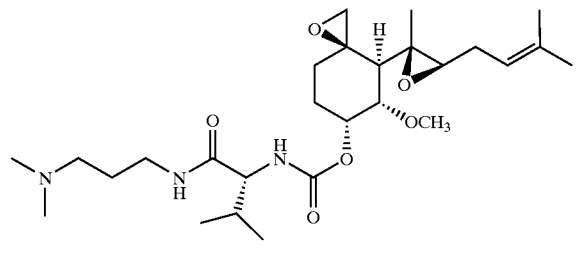

-continued

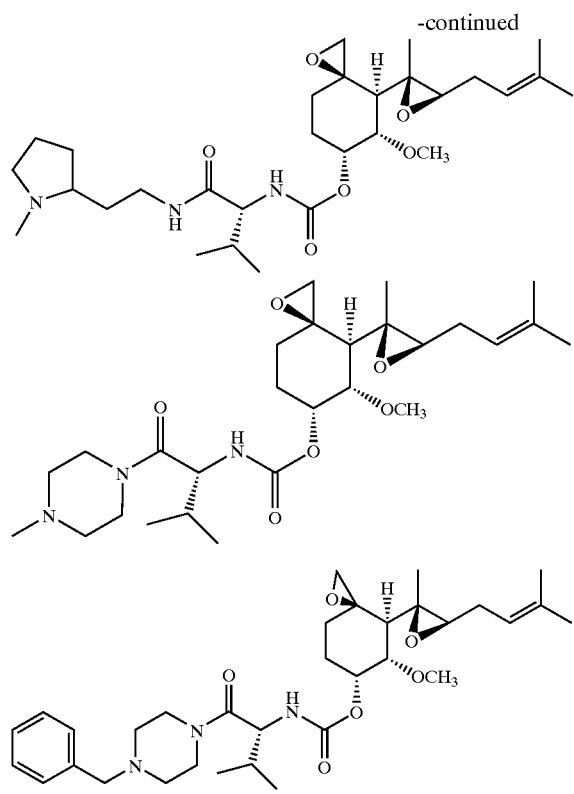

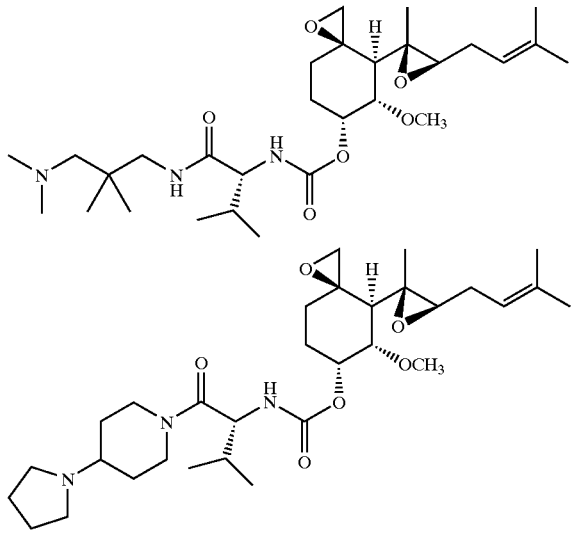

Methods of Using the Angiogenesis inhibitor Compounds for the Treatment of Angiogenic Disease In another embodiment, the present invention provides a method of treating an angiogenic disease in a subject. The method includes administering to the subject a therapeutically effective amount of an angiogenesis inhibitor compound of the present invention, thereby treating the angiogenic disease in the subject.

As used herein, the term "angiogenic disease" includes a disease, disorder, or condition characterized or caused by aberrant or unwanted, e.g., stimulated or suppressed, formation of blood vessels (angiogenesis). Aberrant or unwanted angiogenesis may either cause a particular disease directly or exacerbate an existing pathological condition. Examples of angiogenic diseases include ocular disorders, e.g., diabetic retinopathy, retinopathy of prematurity, corneal graft rejection, retrolental fibroplasia, neovascular glaucoma, rubeosis, retinal neovascularization due to macular degeneration, hypoxia, angiogenesis in the eye associated with infection or surgical intervention, ocular tumors and trachoma, and other abnormal neovascularization conditions of the eye, where neovascularization may lead to blindness; disorders affecting the skin, e.g., psoriasis and pyogenic granuloma; cancer, e.g., carcinomas and sarcomas, where progressive growth is dependent upon the continuous induction of angiogenesis by these tumor cells, lung cancer, brain cancer, kidney cancer, colon cancer, liver cancer, pancreatic cancer, stomach cancer, prostate cancer, breast cancer, ovarian cancer, cervical cancer, melanoma, and metastatic versions of any of the preceding cancers; lymphoid malignancies, e.g., lymphoid leukemias, such as chronic lymphoid leukemia and acute lymphoid leukemia, and lymphomas, such as T cell lymphoma and B cell lymphoma; pediatric disorders, e.g., angiofibroma, and hemophiliac joints; blood vessel diseases such as hemangiomas, and capillary proliferation within atherosclerotic plaques; disorders associated with surgery, e.g., hypertrophic scars, wound granulation and vascular adhesions; and autoimmune diseases such as rheumatoid, immune and degenerative arthritis, where new vessels in the joint may destroy articular cartilage and scleroderma; lupus erythematosus, psoriasis, multiple sclerosis, myasthenia gravis, vasculitis, or diabetes mellitus.

The term angiogenic disease also includes diseases characterized by excessive or abnormal stimulation of endothelial cells, including but not limited to intestinal adhesions, Crohn's disease, atherosclerosis, scleroderma, and hypertrophic scars, i.e., keloids; diseases that have angiogenesis as a pathologic consequence such as cat scratch disease (Rochele ninalia quintosa) and ulcers (*Helicobacter pylori*). In addition, the angiogenesis inhibitor compounds of the present invention are useful as birth control agents (by virtue of their ability to inhibit the angiogenesis dependent ovulation and establishment of the placenta) and may also be used to reduce bleeding by administration to a subject prior to surgery.

The compounds of the invention may also be used to treat a subject suffering from a parasitic infection, such as an infection by *Plasmodium* species, such as *Plasmodium falciparum* or an infection by Leishmania species, such as *Leishmania donavani*. The method comprises the step of administering to the subject a therapeutically effective amount of a compound of the invention. The subject can be an individual who is suffering from, or susceptible to, infection by a parasitic organism. In a preferred embodiment, the subject suffers from malaria or Leishmaniasis.

The compounds of the invention can also be used to treat a subject suffering from a thymoma. Thus the invention provides a method of treating a thymoma in a patient, comprising the step of administering to the patient a therapeutically effective amount of a compound of the invention.

The compounds of the invention can also be used as immunosuppressive agents in clinical protocols in which suppression of the immune system is desired. Thus. the present invention provides a method of inducing an immunosuppressed condition in a subject, comprising the step of administering to the subject an immunosupressive amount of a compound of the invention. For example, the compounds of the invention can be used to suppress immune function in subjects undergoing, or who have undergone, an organ, tissue or cell transplant from a donor. In one embodiment, the transplanted tissue, organ or cell is bone marrow, stem cells, pancreatic cells, such as islet cells, or cornea. In another embodiment, the transplanted organ is a solid organ, such as a liver, a kidney, a heart or a lung.

The compounds of the invention may also be used to treat rheumatic diseases, such as rheumatoid arthritis, lupus, akylosing spondylitis, psoriatic arthritis, scleroderma, Kawasaki syndrome and other rheumatic diseases as set forth in Primer on the Rheumatic Diseases, 11th Edition (John H. Klippel MD, editor; Arthritis Foundation:Atlanta Ga. (1997)).

As used herein, the term "subject" includes warm-blooded animals, preferably mammals, including humans. In a preferred embodiment, the subject is a primate. In an even more preferred embodiment, the primate is a human.

As used herein, the term "administering" to a subject includes dispensing, delivering or applying an angiogenesis inhibitor compound, e.g., an angiogenesis inhibitor compound in a pharmaceutical formulation (as described herein), to a subject by any suitable route for delivery of the compound to the desired location in the subject, including delivery by either the parenteral or oral route, intramuscular injection, subcutaneous/intradennal injection, intravenous injection, buccal administration, transdermal delivery and administration by the rectal, colonic, vaginal, intranasal or respiratory tract route.

As used herein, the term "effective amount" includes an amount effective, at dosages and for periods of time necessary, to achieve the desired result, e.g., sufficient to treat an angiogenic disease in a subject. An effective amount of an angiogenesis inhibitor compound, as defined herein may vary according to factors such as the disease state, age, and weight of the subject, and the ability of the angiogenesis inhibitor compound to elicit a desired response in the subject. Dosage regimens may be adjusted to provide the optimum therapeutic response. An effective amount is also one in which any toxic or detrimental effects (e.g., side effects) of the angiogenesis inhibitor compound are outweighed by the therapeutically beneficial effects.

A therapeutically effective amount of an angiogenesis inhibitor compound (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of an angiogenesis inhibitor compound can include a single treatment or, preferably, can include a series of treatments. In one example, a subject is treated with an angiogenesis inhibitor compound in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of an angiogenesis inhibitor compound used for treatment may increase or decrease over the course of a particular treatment.

The methods of the invention further include administering to a subject a therapeutically effective amount of an angiogenesis inhibitor compound in combination with another pharmaceutically active compound known to treat an angiogenic disease, e.g., a chemotherapeutic agent such as Taxol, Paclitaxel, or Actinomycin D, or an antidiabetic agent such as Tolbutamide; or a compound that may potentiate the angiogenesis inhibitory activity of the angiogenesis inhibitor compound, such as heparin or a sulfated cyclodextrin. Other pharmaceutically active compounds that may be used can be found in Harrison's Principles of Internal Medicine, Thirteenth Edition, Eds. T. R. Harrison et al. McGraw-Hill N.Y., N.Y.; and the Physicians Desk Reference 50th Edition 1997, Oradell N.J., Medical Economics Co., the complete contents of which are expressly incorporated herein by reference. The angiogenesis inhibitor compound and the pharmaceutically active compound may be administered to the subject in the same pharmaceutical composition or in different pharmaceutical compositions (at the same time or at different times).

Pharmaceutical Compositions of the Angiogenesis Inhibitor Compounds

The present invention also provides pharmaceutically acceptable formulations comprising one or more angiogenesis inhibitor compounds. Such pharmaceutically acceptable formulations typically include one or more angiogenesis inhibitor compounds as well as a pharmaceutically acceptable carrier(s) and/or excipient(s). As used herein, "pharmaceutically acceptable carrier" includes any and all solvents, dispersion media, coatings, antibacterial and anti fungal agents, isotonic and absorption delaying agents, and the like that are physiologically compatible. The use of such media and agents for pharmaceutically active substances is well known in the art. Except insofar as any conventional media or agent is incompatible with the angiogenesis inhibitor compounds, use thereof in the pharmaceutical compositions is contemplated.

Supplementary pharmaceutically active compounds known to treat an angiogenic disease, e.g., a chemotherapeutic agent such as Taxol, Paclitaxel, or Actinomycin D, or an antidiabetic agent such as Tolbutamide; or compounds that may potentiate the angiogenesis inhibitory activity of the angiogenesis inhibitor compound, such as heparin or a sulfated cyclodextrin, can also be incorporated into the compositions of the invention. Suitable pharmaceutically active compounds that may be used can be found in Harrison's Principles of Internal Medicine (supra).

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the pharmaceutical composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the angiogenesis inhibitor compound in the required amount in an appropriate solvent with one or a combination of the ingredients enumerated above, as required, followed by filtered sterilization. Generally, dispersions are prepared by incorporating the angiogenesis inhibitor compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the angiogenesis inhibitor compound plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the angiogenesis inhibitor compound can be incorporated with excipients and used in the form of tablets, troches, or capsules. Oral compositions can also include an enteric coating. Oral compositions can also be prepared using a fluid carrier for use as a mouthwash, wherein the angiogenesis inhibitor compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a As. sweetening agent such as sucrose or saccharin; or a flavoring agent such as peppermint, methyl salicylate, or orange flavoring.

For administration by inhalation, the angiogenesis inhibitor compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the angiogenesis inhibitor compounds are formulated into ointments, salves, gels, or creams as generally known in the art.

The angiogenesis inhibitor compounds can also be prepared in the form of suppositories (e.g., with conventional suppository bases such as cocoa butter and other glycerides) or retention enemas for rectal delivery.

In one embodiment, the angiogenesis inhibitor compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. Nos. 4,522,811, 5,455,044 and 5,576,018, and 4,883,666, the contents of all of which are incorporated herein by reference.

The angiogenesis inhibitor compounds of the invention can also be incorporated into pharmaceutical compositions which allow for the sustained delivery of the angiogenesis inhibitor compounds to a subject for a period of at least several weeks to a month or more. Such formulations are described in U.S. Pat. No. 5,968,895, the contents of which are incorporated herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of angiogenesis inhibitor compounds calculated to produce the desired therapeutic effect in association with the required pharmaceutical carrier. The specification for the dosage unit forms of the invention are dictated by and directly dependent on the unique characteristics of the angiogenesis inhibitor compound and the particular therapeutic effect to be achieved, and the limitations inherent in the art of compounding such angiogenesis inhibitor compounds for the treatment of individuals.

Toxicity and therapeutic efficacy of such angiogenesis inhibitor compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Angiogenesis inhibitor compounds which exhibit large therapeutic indices are preferred. While angiogenesis inhibitor compounds that exhibit toxic side effects may be used, care should be taken to design a delivery system that targets such angiogenesis inhibitor compounds to the site of affected tissue in order to minimize potential damage to uninfected cells and, thereby, reduce side effects.

The data obtained from the cell culture assays and animal studies can be used in formulating a range of dosage for use in humans. The dosage of such angiogenesis inhibitor compounds lies preferably within a range of circulating concentrations that include the ED50 with little or no toxicity. The dosage may vary within this range depending upon the dosage form employed and the route of administration utilized. For any angiogenesis inhibitor compounds used in the methods of the invention, the therapeutically effective dose can be estimated initially from cell culture assays. A dose may be formulated in animal models to achieve a circulating plasma concentration range that includes the IC50 (i.e., the concentration of the angiogenesis inhibitor compound which achieves a half-maximal inhibition of symptoms) as determined in cell culture. Such information can be used to more accurately determine useful doses in humans. Levels in plasma may be measured, for example, by high performance liquid chromatography.

Assays for Detecting the Activity of the Angiogenesis Inhibitor Compounds

The angiogenesis inhibitor compounds of the invention may be tested for their ability to modulate (e.g., inhibit or stimulate) angiogenesis in a variety of well known assays, e.g., the rat aortic ring angiogenesis inhibition assay (described herein in Example 27) or in a chorioallantoic membrane (CAM) assay.

The CAM assay may be performed essentially as described in Liekens S. et al. (1997) *Oncology Research* 9: 173–181, the contents of which are incorporated herein by reference. Briefly, fresh fertilized eggs are incubated for 3 days at 37° C. On the third day, the shell is cracked and the egg is placed into a tissue culture plate and incubated at 38° C. For the assay, the angiogenesis inhibitor compound to be tested is attached on a matrix of collagen on a nylon mesh. The mesh is then used to cover the chorioallantoic membrane and the eggs are incubated at 37° C. If angiogenesis occurs, new capillaries form and grow through the mesh within 24 hours. The ability of the angiogenesis inhibitor compound (at various concentrations) to modulate, e.g., inhibit, angiogenesis, e.g., FGF-induced angiogenesis, may then be determined.

The angiogenesis inhibitor compounds of the invention may also be tested for their ability to modulate (e.g., inhibit or stimulate) human endothelial cell growth. Human umbilical vein endothelial cells (HUVE) may be isolated by perfusion of an umbilical vein with a trypsin-containing medium. HUVE may then be cultured in GIT medium (Diago Eiyou Kagaku, Co., Japan) supplemented with 2.5% fetal bovine serum and 2.0 ng/ml of recombinant human basic fibroblast growth factor (rbFGF, Biotechnology Research Laboratories, Takeda, Osaka, Japan) at 37° C. under 5% $CO_2$ and 7% $O_2$. HUVE are then plated on 96-well microtiter plates (Nunc, 1-67008) at a cell density of $2 \times 10^3$/100 $\mu$l of medium. The following day, 100 $\mu$l of medium containing rbFGF (2 ng/ml at the final concentration) and each angiogenesis inhibitor compound at various concentrations may be added to each well. The angiogenesis inhibitor compounds are dissolved in dimethylsulfoxide (DMSO) and then diluted with culture medium so that the final DMSO concentration does not exceed 0.25%. After a 5-day culture, medium is removed, 100 $\mu$l of 1 mg/ml of MTT (3-(4,5-dimethyl-2-thiazolyl)-2,5-diphenyl-2 H-tetrazolium bromide) solution is added to the wells, and microtiters are kept at 37° C. for 4 hours. Then, 100 $\mu$l of 10% sodium dodecyl sulfate (SDS) solution is added to wells, and the microtiters are kept at 37° C. for 5–6 hours. To determine the effects of the angiogenesis inhibitor compound on cell number, the optical density (590 $\mu$m) of each well is measured using an optical densitometer.

The ability of the angiogenesis inhibitor compounds of the invention to modulate capillary endothelial cell migration in vitro may also be tested using the Boyden chamber assay (as described in Falk et al. (1980) *J. Immunol. Meth.* 33:239–247, the contents of which are incorporated herein by reference). Briefly, bovine capillary endothelial cells are plated at $1.5 \times 10^4$ cells per well in serum-free DMEM (Dulbecco's Modified Eagle's Medium) on one side of nucleopore filters pre-coated with fibronectin (7.3 $\mu$g fibronectin/ml PBS). An angiogenesis inhibitor compound is dissolved in ethanol and diluted in DMEM so that the final concentration of ethanol does not exceed 0.01%. Cells are exposed to endothelial mitogen (Biomedical Technologies, Mass.) at 200 $\mu$g/ml and different concentrations of the angiogenesis inhibitor compound in serum-free DMEM for 4 hours at 37° C. At the end of this incubation, the number of cells that migrate through $8\mu$ pores in the filters is determined by counting cells with an ocular grid at 100× in quadruplicate.

The ability of the angiogenesis inhibitor compounds of the invention to modulate tumor growth may be tested in vivo. An animal model, e.g., a C57BL/6N mouse with a mouse reticulum cell sarcoma (M 5076) intraperitoneally transplantated therein, may be used. The tumor cells in ascites can be collected by centrifugation, and suspended in saline. The cell suspension ($2 \times 10^6$ cells/100 $\mu$l/mouse) is inoculated into the right flanks of mice. Tumor-bearing mice are then subcutaneously treated with the angiogenesis inhibitor compound (at various concentrations suspended in 5% arabic gum solution containing 1% of ethanol) for 12 days beginning one day after the tumor inoculation. The tumor growth may be determined by measuring tumor size in two directions with calipers at intervals of a few days.

Finally, the ability of the angiogenesis inhibitor compounds of the invention to modulate the activity of MetAP2 may be tested as follows. Recombinant human MetAP2 may be expressed and purified from insect cells as described in Li and Chang, (1996) *Biochem. Biophys. Res. Commun.* 227:152–159. Various amounts of angiogenesis inhibitor compound is then added to buffer H (10 mM Hepes, pH 7.35, 100 mM KCl, 10% glycerol, and 0.1 M $Co^{2+}$) containing 1 nM purified recombinant human MetAP2 and incubated at 37° C. for 30 minutes. To start the enzymatic reaction a peptide containing a methionine residue, e.g., Met-Gly-Met, is added to the reaction mixture (to a concentration of 1 mM). Released methionine is subsequently quantified at different time points (e.g., at 0, 2, 3, and 5 minutes) using the method of Zou et al. (1995) *Mol. Gen Genetics* 246:247–253).

This invention is further illustrated by the following examples which should not be construed as limiting. The contents of all references, patents and published patent applications cited throughout this application, as well as the Figures and the Sequence Listing, are hereby incorporated by reference.

EXAMPLES

Synthetic Methods

Compounds of the invention can be prepared using one or more of the following general methods.

General Procedure A:

To a mixture of carbonic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester 4-nitro-phenyl ester[1] (1, 0.47 mmol; Han, C. K.; Ahn, S. K.; Choi, N. S.; Hong, R. K.; Moon, S. K.; Chun, H. S.; Lee, S. J.; Kim, J. W.; Hong, C. I.; Kim, D.; Yoon, J. H.; No, K. T. *Biorg. Med. Chem. Lett.* 2000, 10, 39–43) and amine (2.35 mmol) in EtOH (9 mL) was added dropwise, diisopropyl ethyl amine (2.35 mmol). After 3–18 hours, the ethanol was removed in vacuo and the crude material was dissolved into EtOAc (10 mL) and washed with $H_2O$ (2×5 mL), and then brine (5 mL). The organic phase was dried over $Na_2SO_4$ and the solvent removed in vacuo. Purification via flash chromatography (2–5% $MeOH/CH_2Cl_2$) afforded product.

General Procedure B. Part I:

A solution of (3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino)-acetic acid[2] (2, 0.11 mmol; U.S. Pat. No. 6,017,954) in DMF (1 mL) was added to a 10 mL round bottomed flask containing swelled PS-DCC (0.28 mmol). In a separate vessel, the peptide (0.04 mmol) was dissolved into DMF (0.5 mL) and neutralized with NMM (0.04 mmol). After 1 hour, the solution of peptide was added to the pre-activated acid, and the reaction was continued for 5–18 hours. The resin was removed by filtration, washed with DMF (0.5 mL) and the solvent removed in vacuo. Purification via HPLC ($CH_3CN/H_2O$) afforded the product.

General Procedure B. Part II:

A solution of the product in Part I (0.009 mmol) was dissolved into MeOH (1 mL) and was treated with Pd/C (2 mg), then subjected to a $H_2$ atmosphere (38 psi) for 24 hours. The mixture was then filtered through Celite, washed with MeOH (0.5 mL) and the solvent removed in vacuo. Purification via HPLC ($CH_3CN/H_2O$) afforded the product as a white solid.

General Procedure C:

(1-Hydroxymethyl-methyl-propyl)-carbamic acid (3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester (Example 7, 189 mg, 0.46 mmol), acid (0.46 mmol) and DMAP (0.69 mmol) were dissolved into anhydrous $CH_2Cl_2$ (5 mL) and treated with diisopropylcarbodiimide (0.46 mmol). After 7–18 hours, the solvent was removed in vacuo and purification via flash chromatography ($MeOH/CH_2Cl_2$) afforded the product.

Example 1

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid methyl ester

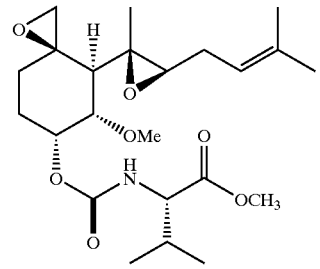

General procedure A was followed using 1 (31 mg, 0.07 mmol), L-valine methyl ester hydrochloride (58 mg, 0.35 mmol), and DIEA (60 μL, 0.35 mmol) in EtOH (2 mL). Purification via flash chromatography (1% $MeOH/CH_2Cl_2$) afforded the product as a clear oil (10 mg, 0.02 mmol, 33% yield); $R_f$=0.60 (20% $EtOAc/CH_2Cl_2$); LRMS (m/z) $[M+1]^+$ 440.3 (calculated for $C_{23}H_{38}NO_7$, 440.3).

Example 2

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid methyl ester

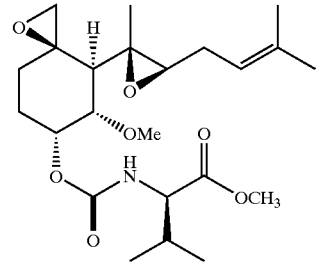

General procedure A was followed using 1 (41 mg, 0.09 mmol) and D-valine methyl ester hydrochloride (77 mg, 0.45 mmol), and DIEA (80 μL, 0.45 mmol) in EtOH (2 mL). Purification via flash chromatography (1% $MeOH/CH_2Cl_2$) afforded the product as a clear oil (18 mg, 0.04 mmol, 45% yield); $R_f$=0.39 (20% $EtOAc/CH_2Cl_2$); LRMS (m/z) $[M+1]^+$ 440.3 (calculated for $C_{23}H_{38}NO_7$, 440.3).

Example 3

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanoic acid methyl ester

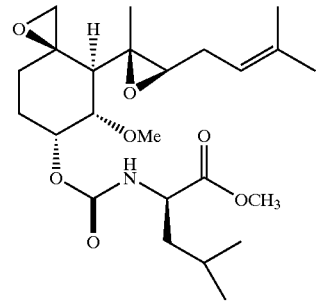

General procedure A was followed using 1 (23 mg, 0.05 mmol), D-leucine methyl ester hydrochloride (47 mg, 0.25 mmol), and DIEA (45 μL, 0.25 mmol) in EtOH (2 mL). Purification via flash chromatography (1% $MeOH/CH_2Cl_2$) afforded the product as a clear oil (19 mg, 0.04 mmol, 83% yield); $R_f$=0.22 (15% EtOAc/CH$_2$Cl$_2$); LRMS (m/z) [M+1]$^+$ 454.3 (calculated for C$_{24}$H$_{40}$NO$_7$, 454.3).

Example 4

{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-phenyl-acetic acid methyl ester

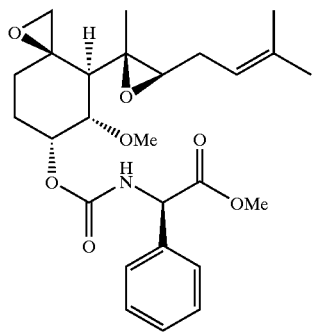

General procedure A was followed using 1 (37 mg, 0.08 mmol), D-phenyl glycine methyl ester hydrochloride (83 mg, 0.40 mmol), and DIEA (72 μL, 0.40 mmol) in EtOH (2 mL). Purification via flash chromatography (1% MeOH/CH$_2$Cl$_2$) afforded the product as a clear oil (32 mg, 0.07 mmol, 82% yield); $R_f$=0.41 (2% MeOH/CH$_2$Cl$_2$); LRMS (m/z) [M+1]$^+$ 474.3 (calculated for C$_{26}$H$_{36}$NO$_7$, 474.3).

Example 5

(1-Carbamoyl-2-methyl-propyl)-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester

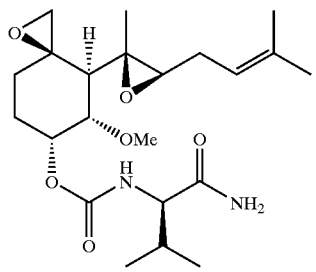

General procedure A was followed using 1 (55 mg, 0.12 mmol), D-valine amide hydrochloride (93 mg, 0.62 mmol), and DIEA (110 μL, 0.62 mmol) in EtOH (2 mL). Purification via flash chromatography (2% MeOH/CH$_2$Cl$_2$) afforded the product as a clear oil (42 mg, 0.10 mmol, 80% yield); $R_f$=0.19 (2% MeOH/CH$_2$Cl$_2$); LRMS (m/z) [M+]$^+$ 425.5 (calculated for C$_{22}$H$_{37}$N$_2$O$_6$, 425.5).

Example 6

(1-Carbamoyl-2-methyl-propyl)-carbamic acid-(3R, 4S, 5S, 6R)-5-methoxy-4-[(2R, 3R)-2-methyl-3-(3-methyl-butyl)-oxiranyl]-1-oxa-spiro[2.5]oct-6-yl ester

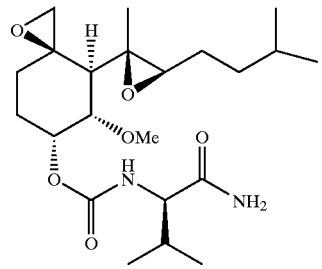

The compound in Example 4 (18 mg, 0.04 mmol) was dissolved into anhydrous MeOH (1.5 mL) and treated with Pd—C (2 mg) under a H$_2$ atmosphere. After 12 hours, the reaction was filtered through Celite and the solvent removed in vacuo to afford the product as a clear oil (18 mg, 0.04 mmol, 100% yield); $R_f$=0.21 (2% MeOH/CH$_2$Cl$_2$); LRMS (m/z) [M+1]$^+$ 427.5 (calculated for C$_{22}$H$_{39}$N$_2$O$_6$, 427.5).

Example 7

(1-Hydroxymethyl-2-methyl-propyl)-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester

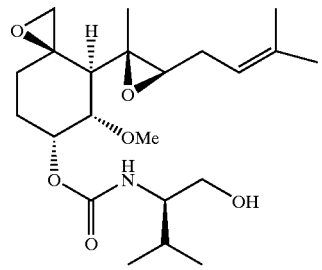

General procedure A was followed using 1 (290 mg, 0.65 mmol), D-valinol (337 mg, 3.25 mmol), and DIEA (560 μL, 3.25 mmol) in EtOH (5 mL). Purification via flash chromatography (2% MeOH/CH$_2$Cl$_2$) afforded the product as a clear oil (200 mg, 0.49 mmol, 75% yield); $R_f$=0.26 (2% MeOH/CH$_2$Cl$_2$); LRMS (m/z) [M+1]$^+$ 412.5 (calculated for C$_{22}$H$_{38}$N$_2$O$_6$, 412.5).

Example 8

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester

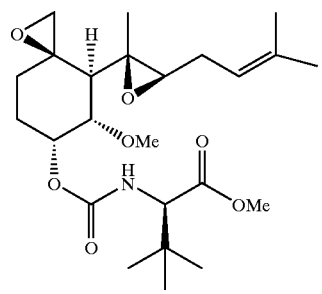

General procedure A was followed using 1 (65 mg, 0.15 mmol), D-tBu glycine methyl ester hydrochloride (132 mg, 0.73 mmol), and DIEA (127 μL, 0.73 mmol) in EtOH (8 mL). Purification via flash chromatography (10% EtOAc/CH$_2$Cl$_2$) afforded the product as a clear oil (10 mg, 0.02 mmol, 15% yield); $R_f$=0.22 (10% EtOAc/CH$_2$Cl$_2$); LRMS (m/z) [M+1]$^+$ 454.5 (calculated for C$_{24}$H$_{24}$NO$_7$, 454.5).

Example 9

Cyclohexyl-2-{(3R, 4S, 5S, 6R)-5-Methoxy-4-[(2R, 3R)-2-methyl-3-(3-but-2-enyl)-oxiranyl]-1-oxa-spiro[2.5]oct-6-yloxycarbonylamino}-acetic acid methyl ester

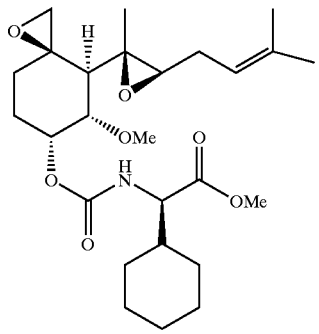

General procedure A was followed using 1 (65 mg, 0.15 mmol), D-cyclohexyl glycine methyl ester hydrochloride (207 mg, 0.73 mmol), and DEA (127 μL, 0.73 mmol) in EtOH (7 mL). Purification via flash chromatography (10% EtOAc/CH$_2$Cl$_2$) afforded the product as a clear oil (20 mg, 0.04 mmol, 28% yield); $R_f$=0.22 (10% EtOAc/CH$_2$Cl$_2$); LRMS (m/z) [M+1]$^+$ 480.3 (calculated for C$_{26}$H$_{42}$NO$_7$, 480.3).

Example 10

2-{(3R, 4S, 5S, 6R)-5-Methoxy-4-[(2R, 3R)-2-methyl-3-3-methyl-but-2-enyl)-oxiranyl]-1-oxa-spiro[2.5]oct-6-yloxycarbonylamino}-3-methyl-pentanoic acid methyl ester

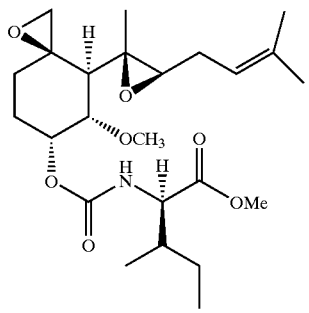

General procedure A was followed using 1 (65 mg, 0.15 mmol), D-isoleucine methyl ester hydrochloride (132 mg, 0.73 mmol), and DIEA (127 μL, 0.73 mmol) in EtOH (7 mL). Purification via flash chromatography (10% EtOAc/CH$_2$Cl$_2$) afforded the product as a clear oil (20 mg, 0.04 mmol, 30% yield); $R_f$=0.20 (10% EtOAc/CH$_2$Cl$_2$); LRMS (m/z) [M+1]$^+$ 454.5 (calculated for C$_{24}$H$_{40}$NO$_7$, 454.5).

Example 11

[1-(1-Carbamoyl-2-hydroxy-ethylcarbamoyl)-2-methyl-propyl]-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester

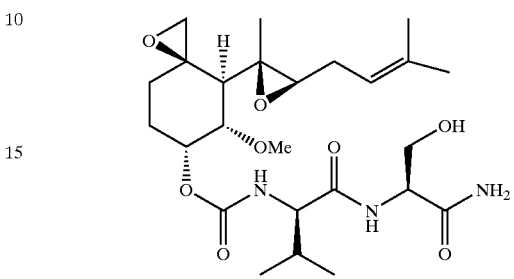

General procedure A was followed using 1 (74 mg, 0.17 mmol), H-D-vS-NH$_2$.TFA (262 mg, 0.83 mmol), and DIEA (140 μL, 0.83 mmol) in EtOH (5 mL). Purification via HPLC (60% CH$_3$CN/H$_2$O) afforded the as a white solid (34 mg, 0.07 mmol, 40% yield); $R_f$=0.21 (5% MeOH/CH$_2$Cl$_2$); LRMS (m/z) [M+1]$^+$ $^{512.5}$ (calculated for C$_{25}$H$_{42}$N$_3$O$_8$, 512.3).

Example 12

2-(3-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yl}-ureido)-3-methyl-butyramide

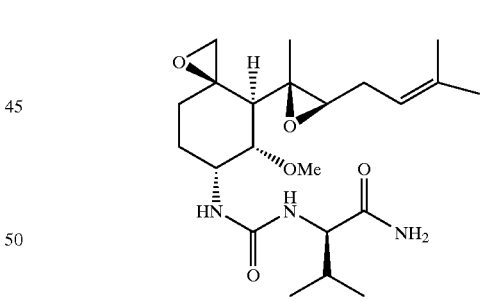

(3R, 4S, 5S, 6R)-5-Methoxy-4-[(2R, 3R)-2-methyl-3-(3-methyl-but-2-enyl)-oxiranyl]-1-oxa-spiro[2.5]oct-6-ylamine (3; PCT Publication No. WO 99/59987) was prepared according to the published procedure. To a solution of crude 3 (29 mg, 0.1 mmol), DIEA (21 mL, 0.1 mmol) and DMAP (2 mg) in CH$_2$Cl$_2$ (1.5 mL) cooled to 0° C. was added p-NO$_2$ phenyl chloroformate (25 mg, 0.12 mmol). After 45 minutes, the reaction was warmed to room temperature and a solution of H-D-val-NH$_2$.HCl (40 mg, 0.15 mmol) in EtOH (1 mmL) and DIEA (35 μL, 0.2 mmol) was added.

The reaction was continued for 1 hour, then was concentrated in vacuo, taken up into EtOAc (15 mL), and washed with dilute $HCl_{aq}$ (2×15 mL), $H_2O$ (2×15 mL) and brine (15 mL). Purification via flash chromatography (5% MeOH/ $CH_2Cl_2$) afforded the product as a white solid (6 mg, 0.014 mmol, 13% yield from 3); $R_f$=0.12 (5% MeOH/$CH_2Cl_2$); LRMS (m/z) [M+1]$^+$ 424.4 (calculated for $C_{22}H_{38}N_3O_5$, 424.4)

Example 13

N-Carbamoyl (ID#31) 3R, 4S, 5S, 6R) 5-methoxy-4-[(2R, 3R)2-methyl-3-(3-methyl-butyl)-oxiranyl]-1-oxa-spiro[2.5]oct-6-yl ester

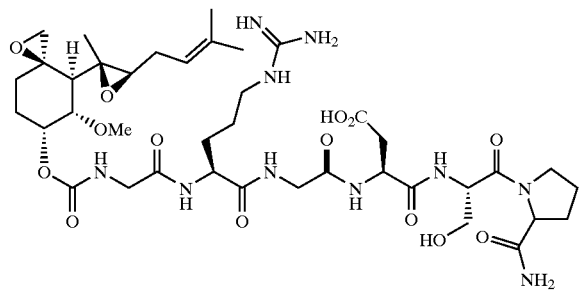

General Procedure B, Part I was followed using 2 (41 mg, 0.11 mmol), PS-DCC (256 mg, 0.28 mmol) in DMF (1 mL) and H-RGD(Bn)S(OBn)P—$NH_2$.2TFA (37 mg, 0.04 mmol), NMM (4 μL, 0.04 mmol) in DMF (0.5 mL). Purification via HPLC (70% $CH_3CN/H_2O$/0.075% TFA) afforded the product as a white floculent solid (9.3 mg, 0.009 mmol, 17% yield); LRMS (m/z) [M+1]$^+$ 1075.4 (calculated for $C_{53}H_{75}N_{10}O_{14}$, 1075.5).

General Procedure, Part II was followed using the product in Part 1 (9.3 mg, 0.009 mmol) and Pd/C (2 mg) in MeOH (1 mL), and a $H_2$ atmosphere (38 psi) for 24 hours. Purification via HPLC (55% $CH_3CN/H_2O$/0.075% TFA) afforded the product as a white solid (5 mg, 0.006 mmol, 65% yield); LRMS (m/z) [M+1]$^+$ 897.3 (calculated for $C_{39}H_{65}N_{10}O_{14}$, 897.5).

Example 14

N-Carbamoyl (ID#30) 3R, 4S, 5S, 6R) 5-methoxy-4-[(2R, 3R)2-methyl-3-(3-methyl-butyl)-oxiranyl]-1-oxa-spiro[2.5]oct-6-yl ester

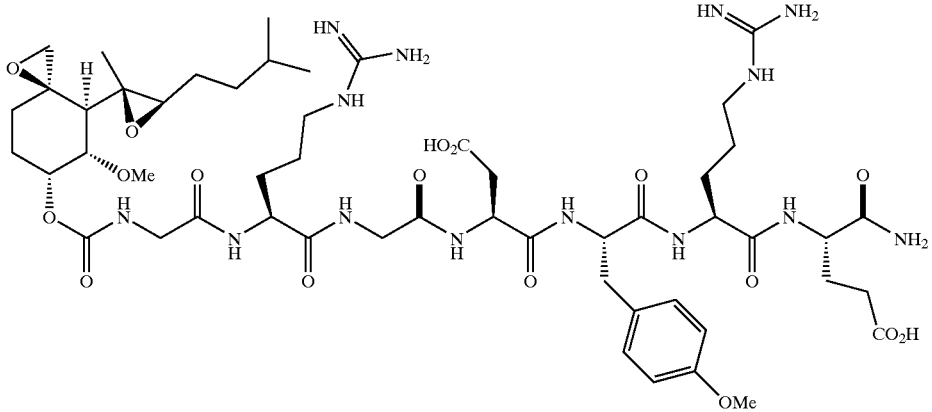

General Procedure, Part I was followed using 2 (38 mg, 0.10 mmol) and PS-DCC (238 mg, 0.25 mmol) in DMF (1 mL), H-RGD(Bn)Y(OMe)RE(Bn)—$NH_2$.3TFA (35 mg, 0.03 mmol) and NMM (3 μL, 0.03 mmol) in DMF (0.5 mL). Purification via HPLC (70% $CH_3CN/H_2O$/0.075% TFA) afforded the product as a white floculent solid (4.0 mg, 0.002 mmol, 8% yield); LRMS (m/z) [M+2/2]$^+$ 677.6 (calculated for $C_{66}H_{92}N14O_{17}$, 677.8).

General Procedure, Part II was followed using the product in Part 1 (3.0 mg, 0.002 mmol) and Pd/C (2 mg) in MeOH (1 mL), under a $H_2$ atmosphere (38 psi) for 24 hours. Purification via HPLC (55% $CH_3CN/H_2O$/0.075% TFA) afforded the product as a white solid (3.3 mg, 0.0027 mmol, 94% yield); LRMS (m/z) [M+2/2]$^+$ 588.5 (calculated for $C_{52}H_{82}N14O_{17}$, 588.7).

Example 15

N-Carbamoyl (ID#32) 3R, 4S, 5S, 6R) 5-methoxy-4-[(2R, 3R)2-methyl-3-(3-methyl-butyl)-oxiranyl]-1-oxa-spiro[2.5]oct-6-yl ester

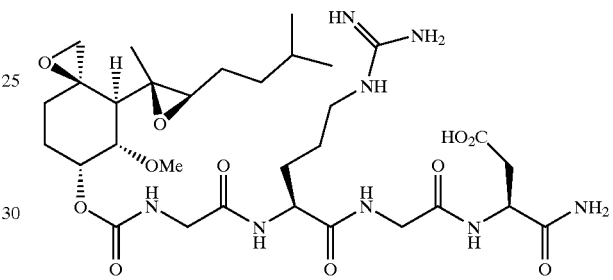

General Procedure B, Part I was followed using 2 (38 mg, 0.10 mmol), PS-DCC (238 mg, 0.25 mmol), and HOBt (29 mg, 0.25mmol) in DMF (1 mL), and H-RGD(Bn)$NH_2$.TFA (29 mg, 0.04 mmol) and NMM (4.8 μL, 0.04 mmol) in DMF (0.5 mL). Purification via HPLC (60% $CH_3CN/H_2O$/0.075% TFA) afforded the product as a white solid (35 mg, 0.04 mmol, 44% yield); LRMS (m/z) 801.2 (calculated for $C_{38}H_{57}N_8O_{11}$, 801.4).

General Procedure, Part II was followed using the product in Part 1 (35 mg, 0.04 mmol) and Pd/C (2 mg) in MeOH (1 mL), under a $H_2$ atmosphere (38 psi) for 24 hours. Purification via HPLC (50% $CH_3CN/H_2O$/0.075% TFA) afforded the product as a white solid (22 mg, 0.03 mmol, 71% yield); LRMS (m/z) 713.2 (calculated for $C_{31}H_{53}N_8O_{11}$, 713.4).

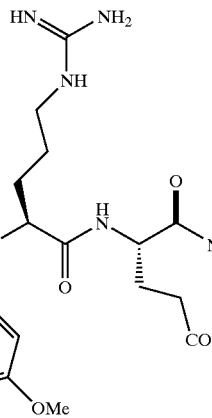

Example 16

N-Carbamoyl (ID#40) (3R, 4S, 5S, 6R) 5-methoxy-4-[(2R, 3R)2-methyl-3-(3-methyl-but-2-enyl)-oxiranyl]-1-oxa-spiro[2.5]oct-6-yl ester

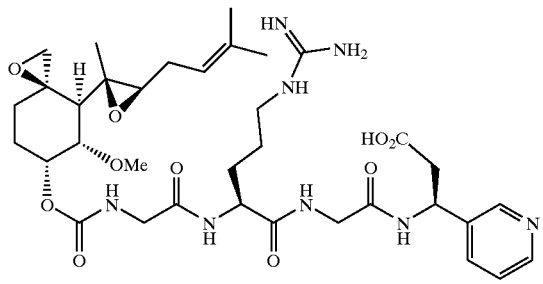

General Procedure B, Part I was followed using 2 (65 mg, 0.17 mmol), PS-DCC (405 mg, 0.43 mmol), and HOBt (34 mg, 0.26 mmol) in DMF (1 mL), and H-RG(pyridyl)D-OMe (43 mg, 0.06 mmol) and NMM (7 μL, 0.06 mmol) in DMF (0.5 mL). Purification via HPLC (50% $CH_3CN/H_2O/0.075\%$ TFA) afforded the product as a white solid (15 mg, 0.02 mmol, 34% yield); LRMS (m/z) 773.2 (calculated for $C_{34}H_{55}N_4O_{10}$, 773.4).

The product of Part I (11 mg, 0.01 mmol) was dissolved into THF:MeOH:$H_2O$ (2:1:1, 500 μL) and treated with LiOH.$H_2O$ (1.2 mg, 0.02 mmol) for 2 hours. The crude material was diluted with EtOAc (5 mL) and acidified with dilute HCl (10 mL). The aqueous phase was washed with additional EtOAc (2×5 mL), the combined organic extracts dried over $Na_2SO_4$ and the solvent removed in vacuo. Purification via HPLC (30% $CH_3CN/H_2O/0.075\%$ TFA) afforded the product as a white solid (2 mg, 0.003 mmol, 19% yield). LRMS (m/z) 745.3 (calculated for $C_{33}H_{53}N_4O_{10}$, 745.4).

Example 17

N-Carbamoyl (ID#39) (3R, 4S, 5S, 6R) 5-methoxy-4-[(2R, 3R)2-methyl-3-(3-methyl-but-2-enyl)-oxiranyl]-1-oxa-spiro[2.5]oct-6-yl ester General procedure B, Part I was followed using 2 (25 mg, 0.07 mmol) and PS-DCC (155 mg, 0.16 mmol) in DMF (1 mL), and H-PLGMWAG-$NH_2$ (20 mg, 0.03 mmol) and NMM (3 μL, 0.03 mmol) in DMF (0.5 mL). Purification via HPLC (70% $CH_3CN/H_2O/0.075\%$ TEA) afforded the product as a white solid (1.4 mg, 0.001 mmol, 5% yield); LRMS (m/z) [M+1]$^+$ 1095.6 (calculated for $C_{53}H_{79}N_{10}O_{13}S$, 1095.6).

Example 18

N-Carbamoyl (ID#26) (3R, 4S, 5S, 6R) 5-methoxy-4-[(2R, 3R)2-methyl-3-(3-methyl-but-2-enyl)-oxiranyl]-1-oxa-spiro[2.5]oct-6-yl ester

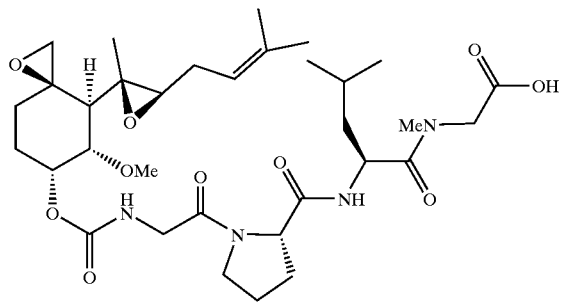

General Procedure B, Part I was followed using 2 (69 mg, 0.18 mmol), PS-DCC (429 mg, 0.45 mmol) and HOBt (21 mg, 0.18 mmol) in DMF (1 mL), and H-PL(N-Me)G-OMe (31 mg, 0.07 mmol) and NMM (8 μL, 0.07 mmol) in DMF (0.5 mL). Purification via HPLC (70% $CH_3CN/H_2O/0.075\%$ TFA) afforded the product as a white solid (27 mg, 0.04 mmol, 59% yield); LRMS (m/z) [M+1]$^+$ 679.4 (calculated for $C_{34}H_{55}N_4O_{10}$, 679.4).

The product of Part I (27 mg, 0.04 mmol) was dissolved into THF:MeOH:$H_2O$ (2:1:1, 1.5 mL) and treated with LiOH.$H_2O$ (4 mg, 0.10 mmol) for 1 hour. The solution was acidified to pH 3 using 0.1 N HCl, and the MeOH and THF removed in vacuo. Purification via HPLC (60% $CH_3CN/H_2O/0.075\%$ TFA) afforded the product as a white solid (6 mg, 0.01 mmol, 23% yield). LRMS (m/z) 665.4 (calculated for $C_{33}H_{53}N_4O_{10}$, 665.4).

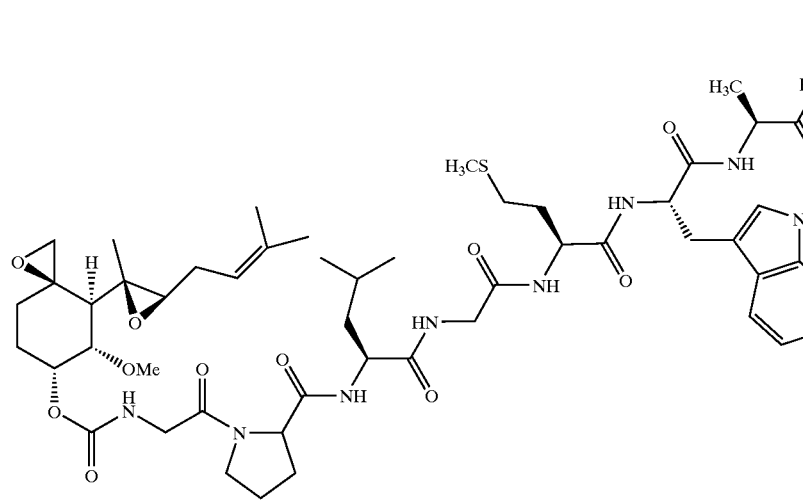
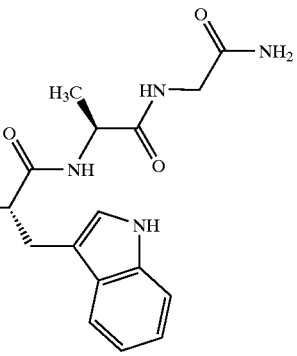

Example 19

N-Carbamoyl (ID#27) (3R, 4S, 5S, 6R) 5-methoxy-4-[(2R, 3R)2-methyl-3-(3-methyl-but-2-enyl)-oxiranyl]-1-oxa-spiro[2.5]oct-6-yl ester

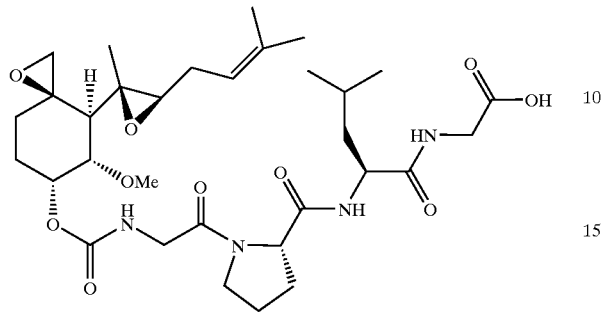

General Procedure B, Part I was followed using 2 (44 mg, 0.12 mmol), PS-DCC (276 mg, 0.29 mmol) and HOBt (27 mg, 0.23 mmol) in DMF (1 mL), and H-PLG-OMe (20 mg, 0.05 mmol) and NMM (5 µL, 0.05 mmol) in DMF (0.5 mL). Purification via HPLC (90% $CH_3CN/H_2O/0.075\%$ TFA) afforded the product as a white solid (13 mg, 0.02 mmol, 43% yield); LRMS (m/z) $[M+1]^+$ 664.4 (calculated for $C_{34}H_{52}N_4O_{10}$, 664.4).

The product in Part 1 (27 mg, 0.04 mmol) was dissolved into $THF:MeOH:H_2O$ (2:1:1, 790 µL) and treated with $LiOH.H_2O$ (1.2 mg, 0.03 mmol) for 2 hours. The solution was acidified to pH 3 using 0.1 N HCl, and the MeOH and THF removed in vacuo. Purification via HPLC (90% $CH_3CN/H_2O/0.075\%$ TFA) afforded the product as a white solid (1.8 mg, 0.003 mmol, 15% yield). LRMS (m/z) 650.4 (calculated for $C_{32}H_{50}N_4O_{10}$, 650.4).

Example 20

(ID#24)-(2R-{(3R, 4S, 5S, 6R)5-methoxy-4-[(2R, 3R)2-methyl-3-(3-methyl-but-2-enyl)-oxiranyl]-1-oxa-spiro[2.5]oct-6-yloxycarbonyl}amino-3-methyl-butanol) ester

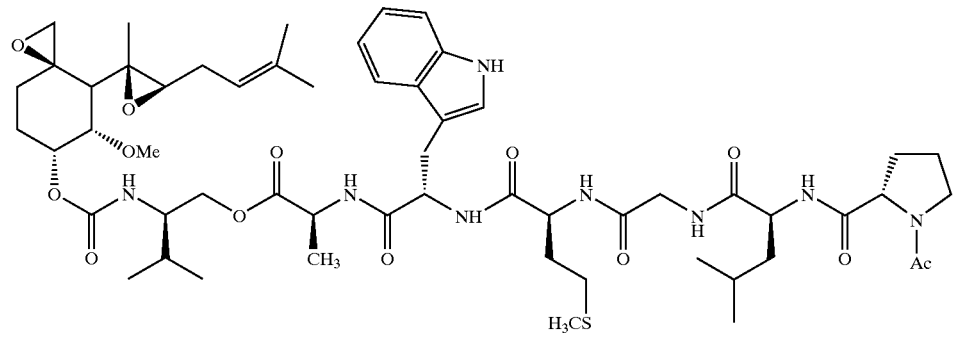

General Procedure C was followed using the compound in Example 7 (189 mg, 0.46 mmol), Ac-PLGMWA-OH (329 mg, 0.46 mmol), DMAP (84 mg, 0.69 mmol) and DIC (72 µL, 0.46 mmol) in $CH_2Cl_2$ (5 mL). After 18 hours, the solvent was removed in vacuo and purification via flash chromatography (2% $MeOH/CH_2Cl_2$) afforded the product as a white solid (357 mg, 0.32 mmol, 70% yield); $R_f$=0.18 (5% $MeOH/CH_2Cl_2$); LRMS (m/z) $[M+1]^+$ 1110.3 (calculated for $C_{56}H_{85}N_8O_{13}S$, 1110.3).

Example 21

(ID#36)-(2R-{(3R, 4S, 5S, 6R) 5-methoxy-4-[(2R, 3R)2-methyl-3-methyl-but-2-enyl)-oxiranyl]-1-oxa-spiro[2.5]oct-6-yloxycarbonyl}amino-3-methyl-butanol) ester

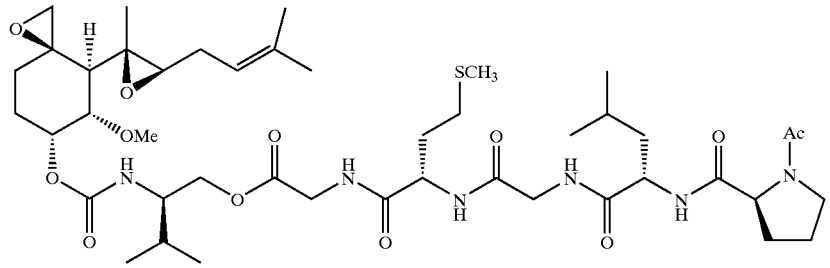

General Procedure C was followed using the compound in Example 7 (61 mg, 0.15 mmol), Ac-PLGMG-OH (92 mg, 0.18 mmol), DMAP (22 mg, 0.18 mmol) and DIC (28 µL, 0.18 mmol) in $CH_2Cl_2$ (2 mL). After 7 hours, the solvent was removed in vacuo and purification via flash chromatography (3% $MeOH/CH_2Cl_2$) afforded the product as a white solid (61 mg, 0. mmol, 45% yield); $R_f$=0.20 (5% $MeOH/CH_2Cl_2$); LRMS (m/z) [M+1]$^+$ 909.7 (calculated for $C_{44}H_{73}N_6O_{12}S$, 909.5).

Example 22

(ID#37)-(2R-{(3R, 4S, 5S, 6R) 5-methoxy-4-[(2R, 3R)2-methyl-3-(3-methyl-but-2-enyl)-oxiranyl]-1-oxa-spiro[2.5]oct-6-yloxycarbonyl}amino-3-methyl-butanol) ester

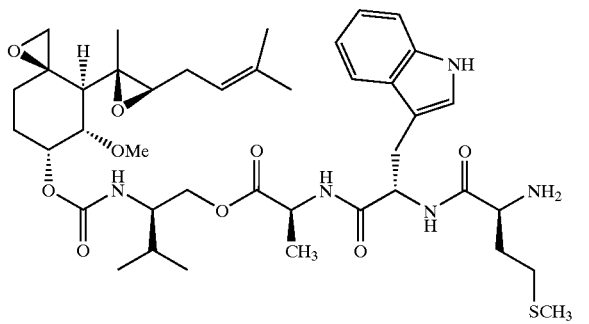

General Procedure C was followed using the compound in Example 7 (79 mg, 0.19 mmol), Fmoc-MWA-OH (121 mg, 0.19 mmol) and DMAP (4 mg, 0.03 mmol) and DIC (30 µL, 0.19 mmol) in $CH_2Cl_2$ (2 mL). After 11 hours, the solvent was removed in vacuo and purification via flash chromatography (2% $MeOH/CH_2Cl_2$) afforded the product as a white solid (128 mg, 0.12 mmol, 65% yield); LRMS (m/z) [M$^+$ 1]$^+$ 1022.9 (calculated for $C_{44}H_{73}N_6O_{12}S$, 1022.5).

The product from General Procedure C (above) (54 mg, 0.05 mmol) was dissolved into anhydrous $CH_2Cl_2$ (3 mL) cooled to 0° C., then treated with a gentle stream of $NH_{3(g)}$ for 15 minutes. The reaction was sealed and continued at 0° C. for 36 hours. The solvent was removed in vacuo, and the crude residue acidified with $CH_3CN/H_2O$(0.075% TFA) (5 mL). Purification via HPLC (70% $CH_3CN/H_2O$/0,075% TFA) afforded the product as a white solid (2 mg, 0.003 mmol, 5% yield); LRMS (m/z) [M+1]$^+$ 800.6 (calculated for $C_{41}H_{62}N_5O_9S$, 800.5).

Example 23

(ID#38)-(2R-{(3R, 4S, 5S, 6R) 5-methoxy-4-[(2R, 3R)2-methyl-3-(3-methyl-but-2-enyl)-oxiranyl]-1-oxa-spiro[2.5]oct-6-yloxycarbonyl}amino-3-methyl-butanol) ester

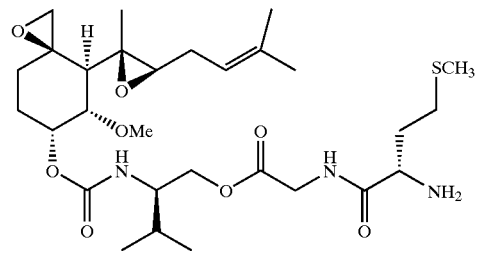

General Procedure C was followed using the compound in Example 7 (76 mg, 0.18 mmol), Fmoc-MG-OH (79 mg, 0.18 mmol) and DMAP (4 mg, 0.03 mmol) and VDIC (29 µL, 0.18 mmol) in $CH_2Cl_2$ (2 mL). After 10 hours, the solvent was removed in vacuo and purification via flash chromatography (2% $MeOW/CH_2Cl_2$) afforded the product as a white solid (128 mg, 0.12 mmol, 65% yield); LRMS (m/z) [M+1]$^+$ 822.6 (calculated for $C_{44}H_{60}N_3O_{10}S$, 822.5).

The product from General Procedure C (above) (42 mg, 0.05 mmol) was dissolved into anhydrous $CH_2Cl_2$ (3 mL) cooled to 0° C., then treated with a gentle stream of $NH_{3(g)}$ for 15 minutes. The reaction was sealed and continued at 0° C. for 36 hours. The solvent was removed in vacuo, and the crude residue acidified with $CH_3CN/H_2O$(0.075% TFA) (5 mL). Purification via HPLC (70% $CH_3CN/H_2O$/0.075% TFA) afforded the product as a white solid (2 mg, 0.003 mmol, 5% yield); LRMS (m/z) [M+1]$^+$ 600.4 (calculated for $C_{29}H_{50}N_3O_8S$, 600.4).

Example 24

2-{(3R, 4S, 5S, 6R)-5-Methoxy-4-[(2R, 3R)-2-methyl-3-(3-methyl-but-2-enyl)-oxiraynol]-1-oxa-spiro[2.5]oct-6-yloxycarbonylamino}-3-methyl-butyric acid

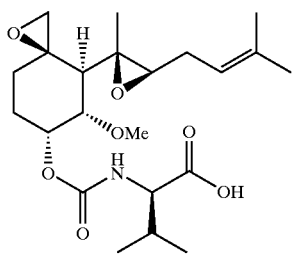

The compound in Example 2 (9 mg, 0.02 mmol) was dissolved into THF:MeOH:H$_2$O(1 mL) and treated with LiOH.H$_2$O(2 mg, 0.05 mmol). After 2 hours, the reaction was partitioned between EtOAc (5 mL) and dilute HCl (5 mmL). The organic phase was dried over Na$_2$SO$_4$ and the solvent removed in vacuo. Purification via HPLC (85% CH$_3$CN/H$_2$O/0.075% TFA) afforded the product as a white solid (0.58 mg, 0.001 mmol, 6% yield); LRMS (m/z) [M+1]$^+$ 426.4 (calculated for C$_{22}$H$_{36}$NO$_7$, 426.5).

Example 25

(ID#34)-(2R-{(3R, 4S, 5S, 6R) 5-methoxy-4-[(2R, 3R)2-methyl-3-(3-methyl-but-2-enyl)-oxiranyl]-1-oxa-spiro[2.5]oct-6-yloxycarbonyl}amino-3-methyl-butanol) ester

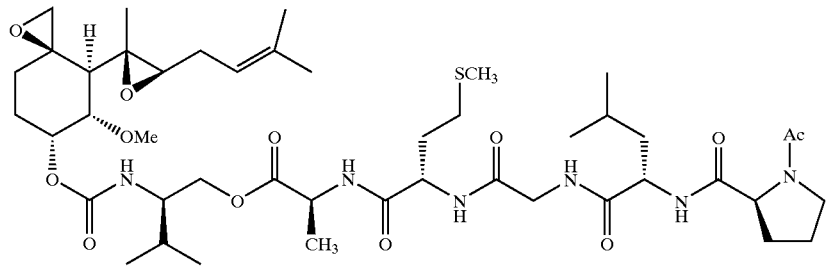

General Procedure C was followed using the compound in Example 7 (41 mg, 0.10 mmol), Ac-PLGMG-OH (63 mg, 0.12 mmol), DMAP (15 mg, 0.12 mmol) and DIC (19 μL, 0.12 mmol) in CH$_2$C$_2$ (2 mL). After 7 hours, the solvent was removed in vacuo and purification via flash chromatography (3% MeOH/CH$_2$Cl$_2$) afforded the product as a white solid (43 mg, 0.05 mmol, 47% yield); R$_f$=0.21 (5% MeOH/CH$_2$Cl$_2$); LRMS (m/z) [M+1]$^+$ 923.7 (calculated for C$_{45}$H$_{75}$N$_6$O$_{12}$S, 923.5).

Example 26

The angiogenesis inhibitor compounds of the invention were tested for their ability to modulate human endothelial cell growth and for their ability to modulate the activity of MetAP2. The MetAP enzyme assay was performed essentially as described in Turk, B. et al. (1999) *Chem. & Bio.* 6: 823–833, the entire contents of which are incorporated herein by reference. The bovine aortic endothelial cell growth assay (Baec assay) was performed essentially as described in Turk, B. et al. (supra), the entire contents of which are incorporated herein by reference.

For the human endothelial cell growth assay, human umbilical vein endothelial cells (HUVEC) were maintained in Clonetics endothelial growth medium (EGM) in a 37° C. humidified incubator. Cells were detached with trypsin and pelleted by centrifugation at 300×g for 5 minutes at room temperature. HUVEC were added to 96-well plates at 5,000 cells/well. After incubating for 6 hours, the medium was replaced with 0.2 ml fresh EGM supplemented with 0.5 nM bFGF and the desired concentration of test angiogenesis inhibitor compound. Test angiogenesis inhibitor compounds were initially dissolved in ethanol at stock concentrations of either 10 mM or 0.1 mM, and subsequently diluted in EGM to obtain concentrations from 1 pM to 10 μM. After 48 hours at 37° C., the medium was replaced with fresh bFGF-supplemented EGM and test angiogenesis inhibitor compound. Following incubation for an additional 48 hours at 37° C. MTT (3-[4,5-dimethylthiazol-2-yl]-2,5-diphenyl-tetrazolium bromide) was added to 1 mg/ml. After 2–4 hours at 37° C. the medium was replaced with 0.1 ml/well isopropanol. The plates were placed on a shaker for 15 minutes at room temperature and analyzed in a Labsystems Multi-skan plate spectrophotometer at an optical density of 570 nm.

The results of the assays, set forth below in Tables I–III, demonstrate that the angiogeness inhibitor compounds of the invention have excellent MetAP2 inhibitory activity and are able to inhibit endothelial cell growth at the picomolar range.

TABLE I

MetAP2 Assay

| Example | IC$_{50}$ (nM) |
|---|---|
| 1 | 4.7 |
| 2 | 2 |
| 3 | 5.5 |
| 4 | 2.7 |
| 13 | 2.9 |
| 14 | 4000 |
| 17 | 16.7 |

TABLE II

Huvec Assay

| Example | IC$_{50}$ (pM) |
|---|---|
| 1 | 18 |
| 2 | 40 |
| 3 | 38 |
| 4 | 36 |
| 5 | 93 |
| 13 | (>10 μM) |
| 14 | (>10 μM) |
| 15 | (>10 μM) |
| 17 | (95 nM) |
| 18 | (>100 nM) |
| 19 | (>100 nM) |
| 24 | 5444 |

TABLE III

Baec Assay

| Example | IC$_{50}$ (pM) |
|---|---|
| 1 | 17 |
| 2 | 48 |
| 3 | 118 |
| 4 | 35 |
| 5 | 46 |
| 6 | 220 |
| 7 | 128 |
| 8 | 313 |
| 9 | 165 |
| 10 | 179 |
| 11 | (>100 nM) |
| 16 | (>100 nM) |
| 19 | (>100 nM) |
| 22 | 326 |
| 23 | 207 |

The identity of the angiogenesis inhibitor compounds used in each of the experiments is shown in Tables IV and V below.

TABLE IV

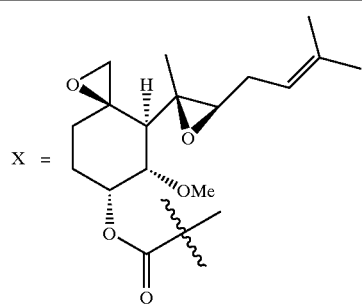

| Example | ID# | Sequence |
|---|---|---|
| 13 | 31 | X-GlyArgGlyAspSerPro-NH$_2$ |
| 14 | 30 | X-GlyArgGlyAspTyr(OMe)Arg Glu-NH$_2$ |
| 15 | 32 | X-GlyArgGlyAsp-NH$_2$ |
| 16 | 40 | X-GlyArg{3-amino-(3-pyridyl)}-proprionic acid |
| 17 | 39 | X-GlyProLeuGlyMetTrpAlaGly-NH$_2$ |
| 18 | 26 | X-GlyProLeuSar-OH |
| 19 | 27 | X-GlyProLeuGly-OH |

TABLE V

| Example | ID# | Sequence |
|---|---|---|
| 20 | 24 | Ac-ProLeuGly-MetTrpAla-Y |
| 21 | 36 | Ac-ProLeuGlyMetGly-Y |
| 22 | 37 | H-MetTrpAla-Y |
| 23 | 38 | H-MetGly-Y |
| 25 | 34 | Ac-ProLeuGlyMetAla-Y |

Example 27

The angiogenesis inhibitor compounds of the invention were also tested for their ability to modulate angiogenesis using the rat aortic ring assay (RARA). For this assay, male Sprague-Dawley rats weighing 125–150 grams were sacrificed by an intramuscular followed by a cardiac injection of catemine, submerged in ethanol, and transferred to a sterile culture hood for dissection. Following a mid-abdominal incision extending to the thorax, the ribs were resected to expose the thoracic cavity. The heart and lungs were moved aside to locate the thoracic aorta. The segment of the aorta distal to the aortic arch and extending to the diaphragm was removed and placed immediately in MCDB-131 medium containing 4 mM L-glutamine and 50 μg/ml gentamycin (buffer A). Buffer A was gently pipeted through the aorta with a pipetman to remove blood. The fibrous tissue was surrounding the aorta was carefully removed and the aorta was sliced into 1–2 mm sections with sterile razor blades. The sections were collected in 50 ml conical tubes and washed five times with fresh buffer A.

Twenty four-well culture plates were coated with 0.2 ml autoclaved 1.5% agarose in buffer A. After the agarose solidified, the wells were filled with 1 ml buffer A. One aortic segment was submerged in each well and incubated in a 35.5° C./5% CO$_2$ humidified incubator for 10 days. Buffer A was replaced every 2 days. The aortic segments were collected in 50 ml conical tubes and washed five times with fresh buffer A.

One milliliter of autoclaved 1.5% agarose in buffer A was added to each well of a twenty four-well culture plate and allowed to solidify. Agarose wells were cut from the solidified agarose with ethanol-sterilized cork borers and placed in twelve-well culture plates. Collagen solution was prepared by mixing 12.8 ml Collaborative Biomedical Products rat tail type I collagen with 2 ml 7.5× Dulbecco's Modified Eagle's Medium adjusted to pH 7 with approximately 0.2 ml 1N NaOH. One hundred microliters of collagen solution was added to the base of the agarose wells and allowed to set in a 35.5° C./5% CO$_2$ humidified incubator. Three hundred microliters of collagen solution supplemented with 0.5 nM bFGF and the desired concentration of test compound was added and an aortic segment was submerged within the upper collagen layer. Test compounds were initially dissolved in ethanol at a stock concentration of 0.1 mM, and subsequently diluted in buffer A and finally collagen solution to obtain concentrations from 0.1 nM to 100 nM. After the collagen set, the agarose wells were surrounded by 1.5 ml buffer A supplemented with 0.5 nM bFGF and the desired concentration of test angiogenesis inhibitor compound. The buffer surrounding the wells was replaced every 48 hours. After seven days, the vessels protruding from the aortic rings were counted under a microscope.

The results of this assay, set forth herein in FIG. 1, demonstrate that the angiogeness inhibitor compounds of the invention have excellent angiogenesis inhibitory activity (much better compared to the angiogenesis inhibitory activity of TNP-470).

Example 28

The plasma stability of the angiogenesis inhibitor compounds of the invention was also tested in human plasma at 37° C. (at a 20 gM concentration of the angiogenesis inhibitor compound). The matrix minus the test angiogenesis inhibitor compound was equilibrated at 37° C. for 3 minutes. The assay was initiated by addition of the test compound, and the reaction mixture was incubated in a shaking water bath at 37° C. Aliquots (100 $\mu$L) were withdrawn in triplicate at 0, 60, and 120 minutes and combined with 200 $\mu$L of ice cold acetonitrile to terminate the reaction. The supernatant was analysed by Liquid Chromatography/Mass spectrometry (LC/MS) using a four point standard curve to obtain percent recovery.

The parent compound remaining (relative to time 0) in the incubation mixture was plotted as a function of time; a first order exponential equation was fit to the observed data, and the elimination half-lives associated with the disappearance of the test angiogenesis inhibitor compound were determined. Results are shown below in Table VI.

TABLE VI

| Test Compound | Percent Recovery (Remaining) | | | | | | $T_{1/2}$ (min) |
|---|---|---|---|---|---|---|---|
| | 0 min | 15 min | 30 min | 60 min | 90 min | 120 min | |
| 5 | 100 | 108 | 103 | 97 | 129 | 107 | ≧500 |
| 20 | 110 | 114 | 114 | 120 | 106 | 103 | ≧500 |

The stability of the angiogenesis inhibitor compounds in liver microsomes was also tested. The test angiogenesis inhibitor compound at a concentration of 3 $\mu$M was incubated with male rat liver microsomes (0.5 mg/mL protein) in the presence of a NADPH regenerating system (1 mM NADP, 10 mM G6P, 1 U/mL G6PdH2, 3 mM MgCl$_2$) in 100 mM Phosphate buffer at pH 7.4 at 37° C. Incubations were performed in the presence and absence of 1 $\mu$M epoxide hydrolase (EH) inhibitor N-cyclohexyl-N'-(3-phenylpropyl) urea (M. Morisseau et al. (1999) PNAS 96:8849–54) and quantitative analysis performed using LC/MS/MS.

The parent compound remaining (relative to time 0) in the incubation mixture was plotted as a function of time; a first order exponential equation was fit to the observed data, and the elimination half-lives associated with the disappearance of the test compound were determined. Results are shown below in Table VII.

TABLE VII

| Test Compound | $T_{1/2}$ (without EH inhibitor) mins | $T_{1/2}$ (with EH inhibitor) mins |
|---|---|---|
| TNP-470 | >1.0 | >1.0 |
| 5 | 11.9 ± 1 | 12.1 ± 1 |

Example 29

The efficacy of the compound described above in example 5 was evaluated using a collagen-induced arthritis model. Briefly, syngeneic 8-week-old female Louvain rats were immunized intradermally under ether anesthesia on Day 0 with 0.5 mg chick collagen II (Genzyme, Boston, Mass.) solubilized in 0.1M acetic acid and emulsified in Incomplete Freund's Adjuvant (Difco, Detroit, Mich.). Using this method, more than 90% of rats typically develop synovitis in both hind limbs 10–14 days post immunization. Rats demonstrating definite arthritis (47 total) were entered into the study and randomly assigned to one of four protocols. The compound of example 5 was dissolved in a combination of ethanol and distilled water. The rats were dosed commencing on day 10 post immunization as follows: (1) control group: vehicle only daily via intravenous injection (iv) (12 rats), (2) high dose group: 30 mg/kg of the compound of example 5 iv every other day (12 rats), (3) low dose group: 15 mg/kg of the compound of example 5 iv every day (12 rats) and (4) oral group: 100 mg/kg of the compound of example 5 every other day by gavage (11 rats).

Daily clinical evaluations of each paw were graded on an integer scale ranging from 0 to 4, where a score of 0 indicates a normal, unaffected limb, and 4 indicates severe joint destruction. The clinical score is the sum of the four limb scores, and has a maximum possible value of 16. Collagen induced arthritis typically develops only in the hind limbs; therefore, a score of 6 to 8 represents severe arthritis.

Radiologic evaluations of the hind limbs were performed by an investigator blinded to the treatment protocol. The score assigned to each limb was based on (1) the degree of soft tissue swelling, (2) narrowing of the space between joints, (3) degree of periosteal new bone formation and (4) the presence of erosions or ankylosis. Each limb was scored on a scale of 1 to 3, with 1 representing a normal limb and 3 representing severe joint destruction. Each rat, thus, had a maximum possible radiographic score of 6 (sum of both hind limbs).

Figure 2:
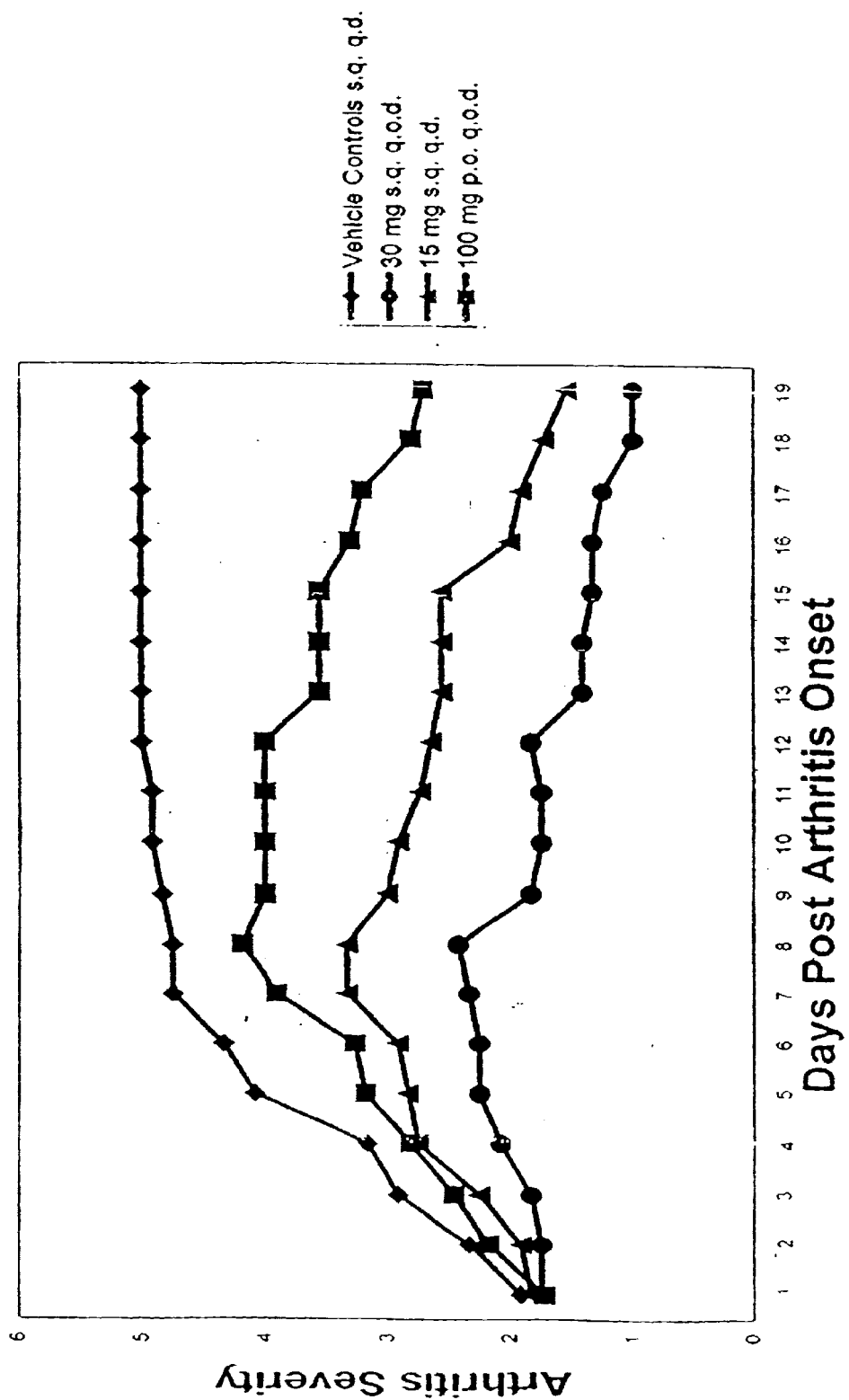
FIG. 2 is a graph depicting the mean daily clinical score for each of the four groups of rats tested over the 19 day period following induction of clinical arthritis.

The results of this study are set forth in FIG. 2, which presents the mean daily clinical score for each of the four groups of rats over the 19 day period following induction of clinical arthritis (day 10). The results indicate that each treatment group received a significant therapeutic benefit from the compound of example 5. Consistent with these observations, the mean radiological evaluation scores were 2.2 for the control group, 0.6 for the high dose group, 0.6 for the low dose group and 1.6 for the oral group. Thus, each group treated with the compound of example 5 received a significant benefit with regard to joint destruction compared to the control group.

Example 30

The compound of example 5 was also evaluated against a panel of cancer cell lines (Alley, M. C. et al. (1998) *Cancer Research* 48: 589–601; Grever, M. R., et al. (1992) *Seminars in Oncology*, Vol. 19, No. 6, pp 622–638; Boyd, M. R., and Paull, K. D. (1995) Drug Development Research 34: 91–109). The human tumor cell lines of the cancer screening panel were grown in RPMI 1640 medium containing 5% fetal bovine serum and 2 mM L-glutamine. Cells were inoculated into 96 well microtiter plates in 100 µL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 hours prior to addition of experimental drugs.

After the 24 hour incubation period, two plates of each cell line were fixed in situ with TCA, to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/ml gentamicin. Additional four, 10-fold or ½ log serial dilutions were made to provide a total of five drug concentrations plus control. Aliquots of 100 µl of these different drug dilutions were added to the appropriate microtiter wells already containing 100 µl of medium, resulting in the required final drug concentrations.

Following drug addition, the plates were incubated for an additional 48 hours at 37° C., 5% $CO_2$, 95% air, and 100% relative humidity. For adherent cells, the assay was terminated by the addition of cold TCA. Cells were fixed in situ by the gentle addition of 50 µl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µl) at 0.4% (w/v) in 1% acetic acid were added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension of the cells, the methodology used was the same except that the assay was terminated by fixing settled cells at the bottom of the wells by gently adding 50 µl of 80% TCA (final concentration, 16% TCA). Using the seven absorbance measurements [time zero, (Tz), control growth, (C), and test growth in the presence of drug at the five concentration levels (Ti)], the percentage growth was calculated at each of the drug concentrations levels.

Percentage growth inhibition was calculated as:

[(Ti−Tz)/(C−Tz)]×100 for concentrations for which Ti>/=Tz

[(Ti−Tz)/Tz]×100 for concentrations for which Ti<Tz.

Growth inhibition of 50% ($GI_{50}$) was calculated from [(Ti−Tz)/(C−Tz)]×100=50, which is the drug concentration resulting in a 50% reduction in the net protein increase (as measured by SRB staining) in control cells during the drug incubation. The $GI_{50}$ was calculated for each of the cell lines if the level of activity is reached; however, if the effect was not reached or is exceeded, the value for that parameter is expressed as greater or less than the maximum ($10^{-4}$ M) or minimum ($10^{-8}$ M) concentration tested.

TABLE VIII

Effect of the compound of example 5 on tumor cell line panel

| Cell line | Tumor type | $GI_{50}$ (moles liter$^{-1}$) |
|---|---|---|
| HL-60(TB) | Leukemia | $2.17 \times 10^{-5}$ |
| K-562 | Leukemia | $6.44 \times 10^{-5}$ |
| MOLT-4 | Leukemia | $3.56 \times 10^{-5}$ |
| RPMI-8226 | Leukemia | $<1 \times 10^{-8}$ |
| SR | Leukemia | $<1 \times 10^{-8}$ |
| EKVX | Non-Small Cell Lung | $2.08 \times 10^{-5}$ |
| HOP-62 | Non-Small Cell Lung | $<1 \times 10^{-8}$ |
| HOP-92 | Non-Small Cell Lung | $3.39 \times 10^{-5}$ |
| NCI-H226 | Non-Small Cell Lung | $7.91 \times 10^{-7}$ |
| NCI-H23 | Non-Small Cell Lung | $6.34 \times 10^{-6}$ |
| NCI-H322M | Non-Small Cell Lung | $4.68 \times 10^{-8}$ |
| NCI-H460 | Non-Small Cell Lung | $<1 \times 10^{-8}$ |
| NCI-H522 | Non-Small Cell Lung | $1.29 \times 10^{-5}$ |
| COLO 205 | Colon | $<1 \times 10^{-8}$ |
| HCT-116 | Colon | $<1 \times 10^{-8}$ |
| HCT-15 | Colon | $7.13 \times 10^{-6}$ |
| HT29 | Colon | $1.61 \times 10^{-5}$ |
| KM12 | Colon | $<1 \times 10^{-8}$ |
| SW-620 | Colon | $>1 \times 10^{-4}$ |
| SF-268 | CNS | $2.61 \times 10^{-5}$ |
| SF-295 | CNS | $<1 \times 10^{-8}$ |
| SF-539 | CNS | $2.06 \times 10^{-5}$ |
| SNB-19 | CNS | $<1 \times 10^{-8}$ |
| SNB-75 | CNS | $9.09 \times 10^{-5}$ |
| MALME-3M | Melanoma | $5.31 \times 10^{-8}$ |
| M14 | Melanoma | $<1 \times 10^{-8}$ |
| SK-MEL-2 | Melanoma | $>1 \times 10^{-4}$ |
| SK-MEL-28 | Melanoma | $5.96 \times 10^{-6}$ |
| SK-MEL-5 | Melanoma | $>1 \times 10^{-4}$ |
| UACC-257 | Melanoma | $1.48 \times 10^{-6}$ |
| UACC-62 | Melanoma | $<1 \times 10^{-8}$ |
| IGR-OV1 | Ovarian | $<1 \times 10^{-8}$ |
| OVCAR-3 | Ovarian | $4.18 \times 10^{-5}$ |
| OVCAR-4 | Ovarian | $3.66 \times 10^{-5}$ |
| OVCAR-5 | Ovarian | $1.35 \times 10^{-8}$ |
| OVCAR-8 | Ovarian | $1.84 \times 10^{-5}$ |
| SK-OV-3 | Ovarian | $7.37 \times 10^{-6}$ |
| 786-0 | Renal | $1.61 \times 10^{-5}$ |
| A498 | Renal | $>1 \times 10^{-4}$ |
| ACHN | Renal | $<1 \times 10^{-8}$ |
| CAKI-1 | Renal | $<1 \times 10^{-8}$ |
| RXF 393 | Renal | $4.02 \times 10^{-5}$ |
| SN12C | Renal | $<1 \times 10^{-8}$ |
| TK-10 | Renal | $5.43 \times 10^{-8}$ |
| PC-3 | Prostate | $1.80 \times 10^{-5}$ |
| DU-145 | Prostate | $<1 \times 10^{-8}$ |
| MCF7 | Breast | $1.24 \times 10^{-5}$ |
| NCI/ADR-RES | Breast | $3.42 \times 10^{-5}$ |
| MDA-MB-231/ATCC | Breast | $<1 \times 10^{-8}$ |
| HS 578T | Breast | $1.15 \times 10^{-6}$ |
| MDA-N | Breast | $1.58 \times 10^{-6}$ |

Results

The results of the cell line screen, presented in Table VIII, show that the compound of example 5 has a significant inhibitory effect on a wide variety of tumor cell lines. The results also show that certain cell lines are much more sensitive to the compound of example 5 than are others, indicating that this compound is selective for certain cell lines.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating a subject having a lymphoid malignancy, comprising administering to the subject a therapeutically effective amount of a compound comprising the structure of Formula XV,

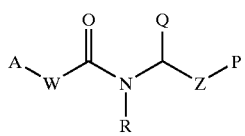

(XV)

wherein
A is a MetAP-2 inhibitory core;
W is O or NR;
each R is, independently, hydrogen or alkyl;
Z is —C(O)— or -alkylene-C(O)—;
P is NHR, OR or a peptide consisting of one to about one hundred amino acid residues connected at the N-terminus to Z;
Q is hydrogen, linear, branched or cyclic alkyl or aryl, provided that when P is —OR, Q is not hydrogen; or
Z is -alkylene-O— or -alkylene-N(R)—;
P is hydrogen or a peptide consisting of from one to about one hundred amino acid residues connected to Z at the carboxyl terminus;
Q is hydrogen, linear, branched or cyclic alkyl or aryl, provided that when P is hydrogen, Q is not hydrogen;
and pharmaceutically acceptable salts thereof.

2. The method of claim 1, wherein Z in said compound is Z is —C(O)— or $C_1$–$C_4$-alkylene-C(O)—.

3. The method of claim 2, wherein Z in said compound is —C(O)— or $C_1$–$C_2$-alkylene-C(O)—.

4. The method of claim 2, wherein Q in said compound is linear, branched or cyclic $C_1$–$C_6$-alkyl, phenyl or naphthyl.

5. The method of claim 4, wherein Q in said compound is isopropyl, phenyl or cyclohexyl.

6. The method of claim 1, wherein Z in said compound is $C_1$–$C_6$-alkylene-O— or $C_1$–$C_6$-alkylene-NR—.

7. The method of claim 6, wherein Z in said compound is $C_1$–$C_4$-alkylene-O— or $C_1$–$C_4$-alkylene-NH—.

8. The method of claim 7, wherein Z in said compound is $C_1$–$C_2$-alkylene-O— or $C_1$–$C_2$-alkylene-NH.

9. The method of claim 6, wherein Q in said compound is linear, branched or cyclic $C_1$–$C_6$-alkyl, phenyl or naphthyl.

10. The method of claim 9, wherein Q in said compound is isopropyl, phenyl or cyclohexyl.

11. The method of claim 1, wherein each R in said compound is, independently, hydrogen or linear, branched or cyclic $C_1$–$C_6$-alkyl.

12. The method of claim 11, wherein each R in said compound is, independently, hydrogen or linear or branched $C_1$–$C_4$-alkyl.

13. The method of claim 12, wherein each R in said compound is, independently, hydrogen or methyl.

14. The method of claim 13, wherein each R in said compound is hydrogen.

15. The method of claim 1, wherein A in said compound is of Formula II,

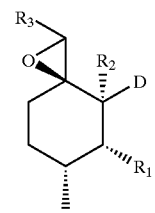

(II)

wherein $R_1$ is hydrogen or alkoxy;

$R_2$ is hydrogen or hydroxy;

$R_3$ is hydrogen or alkyl; and

D is linear or branched alkyl or arylalkyl; or D is of the structure

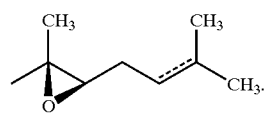

16. The method of claim 15, wherein $R_1$ in said compound is $C_1$–$C_4$-alkoxy.

17. The method of claim 16, wherein $R^1$ in said compound is methoxy.

18. The method of claim 15, wherein $R_3$ in said compound is hydrogen or $C_1$–$C_4$-alkyl.

19. The method of claim 18, wherein $R_3$ in said compound is methyl.

20. The method of claim 15, wherein D in said compound is linear, branched or cyclic $C_1$–$C_6$-alkyl; or aryl-$C_1$–$C_4$-alkyl.

21. The method of claim 1, wherein A in said compound is selected from the group consisting of

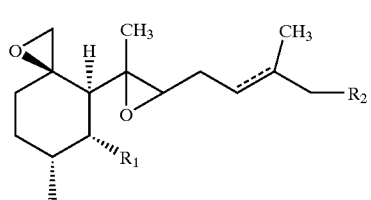

(IV)

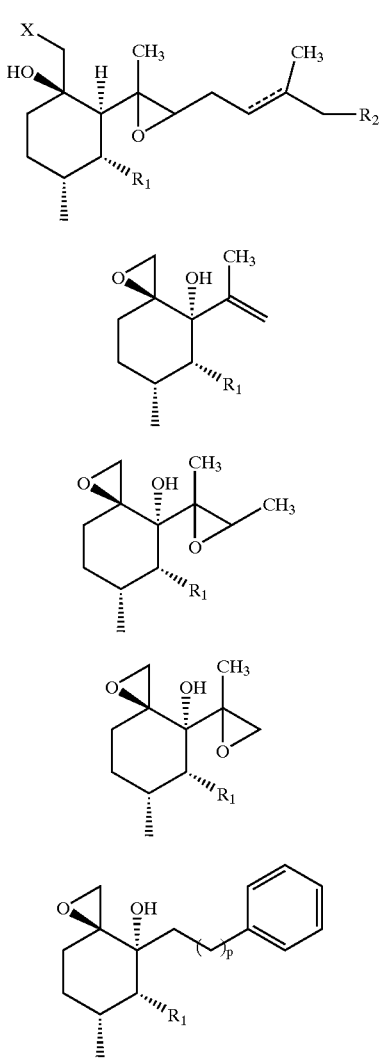

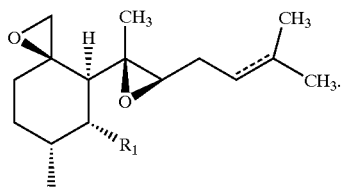

Wherein
p is an integer from 0 to 10;
R¹ is hydrogen, —OH or $C_1$–$C_4$-alkoxy;
X is a leaving group; and
$R_2$ is H, OH, amino, $C_1$–$C_4$-alkylamino or di($C_1$–$C_4$-alkyl)amino).

22. The method of claim 21, wherein A in said compound is of the formula

23. The method of claim 1, wherein P in said compound comprises from 1 to about 20 amino acid residues.

24. The method of claim 23, wherein P in said compound comprises an amino acid sequence which is a substrate for a matrix metalloprotease.

25. The method of claim 24, wherein the matrix metalloprotease is selected from the group consisting of MMP-2, MMP-1, MMP-3, MMP-7, MMP-8, MMP-9, MMP-12, MMP-13 and MMP-26.

26. The method of claim 25, wherein the matrix metalloprotease is MMP-2 or MMP-9.

27. The method of claim 26, wherein P in said compound comprises the sequence -Pro-Leu-Gly-Xaa-, wherein Xaa is a naturally occurring amino acid residue.

28. The method of claim 27, wherein P is Pro-Cha-Ala-Abu-Cys(Me)-His-Ala (SEQ ID NO:16).

29. A method of treating a subject having a lymphoid malignancy-comprising administering to the subject a therapeutically effective amount of a compound comprising the structure

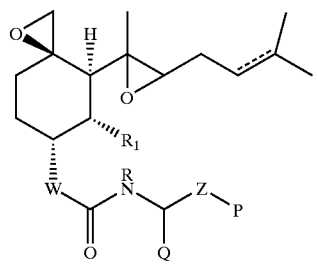

wherein
W is O or NR;
each R is, independently hydrogen or a $C_1$–$C_4$-alkyl;
Q is hydrogen; linear, branched or cyclic $C_1$–$C_6$-alkyl; or aryl;
$R_1$ is hydroxy, $C_1$–$C_4$-alkoxy or halogen;
Z is —C(O)— or $C_1$–$C_4$-alkylene;
P is NHR, OR, or a peptide comprising 1 to 100 amino acid residues attached to Z at the N-terminus; or
Z is alkylene-O or alkylene-NR; and
P is hydrogen or peptide comprising 1 to 100 amino acid residues attached to Z at the C-terminus;
or a pharmaceutically acceptable salt thereof; provided that when P is hydrogen, NHR or OR, Q is not hydrogen.

30. The method of claim 29, wherein
W is O or NH;
Z is alkylene-O or alkylene-NH;
Q is isopropyl;
$R_1$ is methoxy; and
P comprises from 1 to 15 amino acid residues.

31. The method of claim 30, wherein W in said compound is O; and P comprises 10 or fewer amino acid residues.

32. The method of claim 29, wherein P in said compound comprises from 1 to about 20 amino acid residues.

33. The method of claim 32, wherein P in said compound comprises an amino acid sequence which is a substrate for a matrix metalloprotease.

34. The method of claim 33, wherein the matrix metalloprotease is selected from the group consisting of MMP-2, MMP-1, MMP-3, MMP-7, MMP-8, MMP-9, MMP-12, MMP-13 and MMP-26.

35. The method of claim wherein the matrix metalloprotease is MMP-2 or MMP-9.

36. The method of claim 35, wherein P in said compound comprises the sequence -Pro-Leu-Gly-Xaa-, wherein Xaa is a naturally occurring amino acid residue.

37. The method of claim 36, wherein P is -Pro-Cha-Ala-Abu-Cys(Me)-His-Ala (SEQ ID NO:16).

38. A method of treating a subject having a lymphoid malignancy, comprising administering to the subject a therapeutically effective amount of a compound comprising a structure selected from the group consisting of {(3R, 4S, 5S, 6R)-5-Methoxy-4-[2R, 3R)-2-methyl-3-(3-methyl-but-2-enyl)-oxiranyl]-1-oxa-spiro[2.5]oct-6-yloxycarbonylamino}-3-methyl-butyric acid methyl ester;

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid methyl ester;

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanaic acid methyl ester;

{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-phenyl-acetic acid methyl ester;

(1-Carbamoyl-2-methyl-propyl)-caxbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;

(1-Carbamoyl-2-methyl-propyl)-carbamic acid-(3R, 4S, 5S, 6R)-5-methoxy-4-[(2R, 3R)-2-methyl-3-(3-methyl-butyl)-oxiranyl]-1-oxa-spiro[2.5]oct-6-yl ester;

(1-Hydroxymethyl-2-methyl-propyl)-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;

2-{(3R, 4S, 5S, 6R)-5-Methoxy-4-[2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester;

Cyclohexyl-2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-acetic acid methyl ester;

2-{(3R, 4S, 5S, 6R)-5-Methoxy-4-[(2R, 3R)-2-methyl-3 (3-methyl-but-2-enyl)-oxiranyl]-1-oxa-spiro[2.5]oct-6-yloxycarbonylamino}-3-methyl-pentanoic acid methyl ester;

[1-(1-Carbamoyl-2-hydroxy-ethylcarbamoyl)-2-methyl-propyl]-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;

2-(3-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yl}-ureido)-3-methyl-butyramide;

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid;

(ID#31) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#30) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#32) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#40) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#39) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#26) N-Carbamoyl (3R, 4S, 5S, 6R) 5-methoxy-4-[(2R, 3R)2-methyl-3-(3-(3-methyl-butyl)-oxiranyl]-1-oxa-spiro[2.5]oct-6-yl ester;

(ID#27) N-Carbamoyl (3R, 4S, 5S, 6R) 5-methoxy-4-[(2R, 3R)2-methyl-3-(3-(3-methyl-butyl)-oxiranyl]-1-oxa-spiro[2.5]oct-6-yl ester;

(ID#24)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#36)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#37)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#38)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#34)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

{2-Methyl-1-[methyl-(1-methyl-piperidin-4-yl)-carbamoyl]-propyl}-carbamic acid 5-methoxy-4-[2-methyl-3-(3-methyl-but-2-enyl)-oxiranyl]-1-oxa-spiro[2.5]oct-6-yl ester;

[1-(2-Dimethylamino-ethylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;

{1-[(2-Dimethylamino-ethyl)-methyl-carbamoyl]-2-methyl-Propyl}-carbamic acid 5-methoxy-4-[2-methyl-3-(3-methyl-but-2-enyl)-oxiranyl]-1-oxa-spiro[2.5]oct-6-yl ester;

[1-(3-Dimethylamino-propylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;

[1-(3-Dimethylamino-2,2-dimethyl-propylcarbamol)-2-methyl-propyl]-carbamic acid 5-methoxy-4-[2-methyl-3-(3-methyl-but-2-enyl)-oxiranyl]-1-oxa-spiro[2.5]oct-6-yl ester;

[2-Methyl-1-(4-methyl-piperazine-1-carbonyl)-propyl]-carbamic acid 5-methoxy-4-[2-methyl-3-(3-methyl-but-2-enyl)-oxiranyl]-1-oxa-spiro[2.5]oct-6-yl ester;

{2-Methyl-1-[2-(1-methyl-pyrrolidin-2-y1)-ethylcarbamoyl]-propyl}-carbamic acid 5-methoxy-4-[2-methyl-3-(3-methyl-but-2-enyl)-oxiranyl]-1-oxa-spiro[2.5]oct-6-yl ester;

[2-Methyl-1-(4-pyrrolidin-1-yl-piperidine-1-carbonyl)-propyl]-carbamic acid 5-methoxy-4-[2-methyl-3-(3-methyl-but-2-enyl)-oxiranyl]-1-oxa-spiro[2.5]oct-6-yl ester; and

[1-(4-Benzyl-piperazine-1-carbonyl)-2-methyl-propyl]-carbamic acid 5-methoxy-4-[2-methyl-3-(3-methyl-but-2-enyl)-oxiranyl]-1-oxa-spiro[2.5]oct-6-yl ester.

39. A method of treating a subject having a lymphoid malignancy, comprising administering to the subject a therapeutically effective amount of a compound comprising the structure

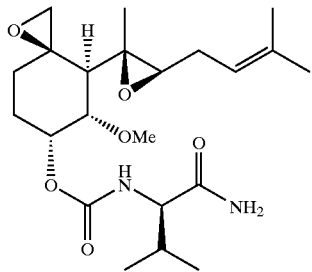

40. The method of any one of claims 1, 29, 38, 39, wherein said lymphoid malignancy is a lymphoma.

41. The method of claim 40 wherein said lymphoma is a B cell lymphoma.

42. The method any one of claims 1, 29, 38, 39, wherein said lymphoid malignancy is leukemia.

43. A method of treating a subject having a parasitic infection, comprising administering to the subject a therapeutically effective amount of a compound comprising the structure of Formula XV,

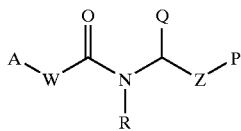

(XV)

wherein

A is a MetAP-2 inhibitory core;

W is O or NR;

each R is, independently, hydrogen or alkyl;

Z is —C(O)— or -alkylene-C(O)—;

P is NHR, OR or a peptide consisting of one to about one hundred amino acid residues connected at the N-terminus to Z;

Q is hydrogen, linear, branched or cyclic alkyl or aryl, provided that when P is —OR, Q is not hydrogen; or Z is -alkylene-O— or -alkylene-N(R)—;

P is hydrogen or a peptide consisting of from one to about one hundred amino acid residues connected to Z at the carboxyl terminus;

Q is hydrogen, linear, branched or cyclic alkyl or aryl, provided that when P is hydrogen, Q is not hydrogen;

and pharmaceutically acceptable salts thereof.

44. A method for treating a subject having a parasitic infection comprising administering to said subject a compound comprising the formula

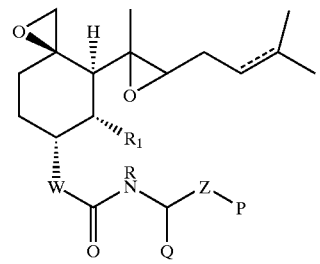

wherein

W is O or NR;

each R is, independently, hydrogen or $C_1$–$C_4$-alkyl;

Q is a linear, branched or cyclic $C_1$–$C_6$-alkyl; or aryl;

$R_1$ is hydroxyl, $C_1$–$C_4$-alkoxy or halogen;

Z is —C(O)—;

P is NHR or OR or a pharmaceutically acceptable salt thereof.

45. The method of claim 44, wherein

W is O;

$R_1$ is methoxy;

each R is hydrogen or methyl;

Q is linear, branched or cyclic alkyl or aryl; and

P is $NH_2$ or $OCH_3$.

46. The method of claim 45, wherein Q is linear, branched or cyclic $C_1$–$C_6$-alkyl and P is $NH_2$.

47. A method for treating a subject having a parasitic infection comprising administering to said subject a compound comprising the structure

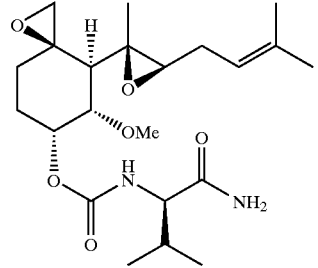

48. A method of treating a subject having a parasitic infection, comprising administering to the subject a therapeutically effective amount of a compound comprising a structure selected from the group consisting of {(3R, 4S, 5S, 6R)-5-Methoxy-4-[2R, 3R)-2-methyl-3-(3-methyl-but-2-enyl)-oxiranyl]-1-oxa-spiro[2.5]oct-6-yloxycarbonylamino}-3-methyl-butyric acid methyl ester;

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid methyl ester;

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanaic acid methyl ester;

{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-phenyl-acetic acid methyl ester;

(1-Carbamoyl-2-methyl-propyl)-caxbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;

(1-Carbamoyl-2-methyl-propyl)-carbamic acid-(3R, 4S, 5S, 6R)-5-methoxy-4-[(2R, 3R)-2-methyl-3-(3-methyl-butyl)-oxiranyl]-1-oxa-spiro[2.5]oct-6-yl ester;

(1-Hydroxymethyl-2-methyl-propyl)-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;

2-{(3R, 4S, 5S, 6R)-5-Methoxy-4-[2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester;

Cyclohexyl-2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-acetic acid methyl ester;

2-{(3R, 4S, 5S, 6R)-5-Methoxy-4-[(2R, 3R)-2-methyl-3 (3-methyl-but-2-enyl)-oxiranyl]-1-oxa-spiro[2.5]oct-6-yloxycarbonylamino}-3-methyl-pentanoic acid methyl ester;

[1-(1-Carbamoyl-2-hydroxy-ethylcarbamoyl)-2-methyl-propyl]-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;

2-(3-{(3R, 4S, 5S, 6R)-5-Methoxy-4-[(2R, 3R)-2-methyl-3-(3-methyl-but-2-enyl)-oxiranyl]-1-oxa-spiro[2.5] oct-6-yl}-ureido)-3-methyl-butyramide;

2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid;

(ID#31) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#30) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#32) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#40) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#39) N-Carbamoyl (3R, 4S, 5S, 6R) 5-methoxy-4-[(2R, 3R)2-methyl-3-(3-methyl-butyl)-oxiranyl]-1-oxa-spiro[2.5]oct-6-yl ester;

(ID#26) N-Carbamoyl (3R, 4S, 5S, 6R) 5-methoxy-4-[(2R, 3R)2-methyl-3-(3-(3-methyl-butyl)-oxiranyl]-1-oxa-spiro[2.5]oct-6-yl ester;

(ID#27) N-Carbamoyl (3R, 4S, 5S, 6R) 5-methoxy-4-[(2R, 3R)2-methyl-3-(3-(3-methyl-butyl)-oxiranyl]-1-oxa-spiro[2.5]oct-6-yl ester;

(ID#24)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#36)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#37)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#38)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

(ID#34)-(2R-{(3R, 4S, 5S, 6R) 5-methoxy-4-[(2R, 3R)2-methyl-3-(3-(3-methyl-butyl)-oxiranyl]-1-oxa-spiro[2.5]oct-6-yloxycarbonyl}amino-3-methyl-butanol) ester;

{2-Methyl-1-[methyl-(1-methyl-piperidin-4-yl)-carbamoyl]-propyl}-carbamic acid 5-methoxy-4-[2-methyl-3-(3-methyl-but-2-enyl)-oxiranyl]-1-oxa-spiro[2.5]oct-6-yl ester;

[1-(2-Dimethylamino-ethylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;

{1-[(2-Dimethylamino-ethyl)-methyl-carbamoyl]-2-methyl-Propyl}-carbamic acid 5-methoxy-4-[2-methyl-3-(3-methyl-but-2-enyl)-oxiranyl]-1-oxa-spiro[2.5]oct-6-yl ester;

[1-(3-Dimethylamino-propylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;

[1-(3-Dimethylamino-2,2dimethyl-propylcarbamol)-2-methyl-propyl]-carbamic acid 5-methoxy-4-[2-methyl-3-(3-methyl-but-2-enyl)-oxiranyl]-1-oxa-spiro[2.5] oct-6-yl ester;

[2-Methyl-1-(4-methyl-piperazine-1-carbonyl)-propyl]-carbamic acid 5-methoxy-4-[2-methyl-3-(3-methyl-but-2-enyl)-oxiranyl]-1-oxa-spiro[2.5]oct-6-yl ester;

{2-Methyl-1-[2-(1-methyl-pyrrolidin-2-y1)-ethylcarbamoyl]-propyl}-carbamic acid 5-methoxy-4-[2-methyl-3-(3-methyl-but-2-enyl)-oxiranyl]-1-oxa-spiro[2.5]oct-6-yl ester;

[2-Methyl-1-(4-pyrrolidin-1-yl-piperidine-1-carbonyl)-propyl]-carbamic acid 5-methoxy-4-[2-methyl-3-(3-methyl-but-2-enyl)-oxiranyl]-1-oxa-spiro[2.5]oct-6-yl ester; and

[1-(4-Benzyl-piperazine-1-carbonyl)-2-methyl-propyl]-carbamic acid 5-methoxy-4-[2-methyl-3-(3-methyl-but-2-enyl)-oxiranyl]-1-oxa-spiro[2.5]oct-6-yl ester.

49. The method any one of claims 1, 29, 38, 39, 43, 44, 47 or 48 wherein said subject is human.

50. The method any one of claims 1, 29, 38, 39, 43, 44, 47 or 48 wherein said compound is administered to said subject using a pharmaceutically acceptable formulation.

51. The method any one of claims 1, 29, 38, 39, 43, 44, 47 or 48 wherein said compound is administered to the subject intravenously.

52. The method any one of claims 1, 29, 38, 39, 43, 44, 47 or 48 wherein said compound is administered to the subject intramuscularly.

53. The method any one of claims 1, 29, 38, 39, 43, 44, 47 or 48 wherein said compound is administered to the subject orally.

* * * * *

UNITED STATES PATENT AND TRADEMARK OFFICE
CERTIFICATE OF CORRECTION

PATENT NO.      : 6,919,307 B2
DATED           : July 19, 2005
INVENTOR(S)     : Gary L. Olson et al.

It is certified that error appears in the above-identified patent and that said Letters Patent is hereby corrected as shown below:

Column 75,
Lines 42-43, replace "compound is Z is" with -- compound is --.

Column 77,
Lines 47-48, replace "di($C_1$-$C_4$-alkyl)amino)" with -- di($C_1$-$C_4$-alkyl)amino --.

Column 78,
Line 29, replace "independently hydrogen" with -- independently, hydrogen --.
Line 59, replace "claim wherein" with -- claim 34, wherein --.

Column 79,
Line 3, replace "{(3R, 4S, 5S, 6R)-5-Methoxy-4-[2R, 3R)-2-methyl-3-(3-methyl-but-2-enyl)-oxiranyl)-1-oxa-spiro[2.5]oct-6-yloxycarbonylamino}-3-methyl-butyric acid methyl ester;" with -- {(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-butyric acid methyl ester; --.

Line 11, replace "2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanaic acid methyl ester;" with -- 2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanoic acid methyl ester; --.

Line 19, replace "(1-Carbamoyl-2-methyl-propyl)-caxbamic acid-(3R, 4S, 5S, 6R )-5-methoxy-4-[(2R, 3R)-2-methyl-3-(3-methyl-but-2-enyl)-oxiranyl]-1-oxa-spiro[2.5]oct-6-yl ester;" with -- 1-Carbamoyl-2-methyl-propyl)-carbamic acid-(3R, 4S, 5S, 6R )-5-methoxy-4-[(2R, 3R)-2-methyl-3-(3-methyl-but-2-enyl)-oxiranyl]-1-oxa-spiro[2.5]oct-6-yl ester; --.

Line 29, replace "2-{(3R, 4S, 5S, 6R )-5-Methoxy-4-[2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester;" with -- 2-{(3R, 4S, 5S, 6R )-5-Methoxy-4-[(2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester; --.

Line 38, replace "2-{(3R, 4S, 5S, 6R)-5-Methoxy-4-[(2R, 3R)-2-methyl-3(3-methyl-but-2-enyl)-oxiranyl]-1-oxa-spiro[2.5]oct-6-yloxycarbonylamino}-3-methyl-pentanoic acid methyl ester;" with -- 2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-pentanoic acid methyl ester; --.

UNITED STATES PATENT AND TRADEMARK OFFICE
CERTIFICATE OF CORRECTION

PATENT NO. : 6,919,307 B2
DATED : July 19, 2005
INVENTOR(S) : Gary L. Olson et al.

It is certified that error appears in the above-identified patent and that said Letters Patent is hereby corrected as shown below:

Column 79 (cont'd),
Line 52, replace "(ID#31) N-Carbamoyl (3$R$, 4$S$, 5$S$, 6$R$) 5-methoxy-4-[(2$R$,3$R$)2-methyl-3-(3-methyl-butyl)-oxiranyl]-1-oxa-spiro[2.5]oct-6-yl ester; with -- (ID#31)-N-Carbamoyl-(3$R$, 4$S$, 5$S$, 6$R$)-5-methoxy-4-[(2$R$,3$R$)-2-methyl-3-(3-methyl-butyl)-oxiranyl]-1-oxa-spiro[2.5]oct-6-yl ester; --.

Line 56, replace "(ID#30) N-Carbamoyl(3$R$, 4$S$, 5$S$, 6$R$) 5-methoxy-4-[(2R,3R)2-methyl-3-(3-methyl-butyl)-oxiranyl]-1-oxa-spiro[2.5]oct-6-yl ester;" with -- (ID#30)-N-Carbamoyl-(3$R$, 4$S$, 5$S$, 6$R$)-5-methoxy-4-[(2R,3R)-2-methyl-3-(3-methyl-butyl)-oxiranyl]-1-oxa-spiro[2.5]oct-6-yl ester; --.

Line 59, replace "(ID#32) N-Carbamoyl (3$R$, 4$S$, 5$S$, 6$R$) 5-methoxy-4-[(2R,3R)2-methyl-3-(3-methyl-butyl)-oxiranyl]-1-oxa-spiro[2.5]oct-6-yl ester;" with -- (ID#32)-N-Carbamoyl-(3$R$, 4$S$, 5$S$, 6$R$)-5-methoxy-4-[(2R,3R)-2-methyl-3-(3-methyl-butyl)-oxiranyl]-1-oxa-spiro[2.5]oct-6-yl ester; --.

Line 62, replace "(ID#40) N-Carbamoyl (3$R$, 4$S$, 5$S$, 6$R$) 5-methoxy-4-[(2R,3R)2-methyl-3-(3-methyl-butyl)-oxiranyl]-1-oxa-spiro[2.5]oct-6-yl ester;" with -- (ID#40)-N-Carbamoyl-(3$R$, 4$S$, 5$S$, 6$R$)-5-methoxy-4-[(2R,3R)-2-methyl-3-(3-methyl-but-2-enyl)-oxiranyl]-1-oxa-spiro[2.5]oct-6-yl ester; --.

Line 65, replace "(ID#39) N-Carbamoyl (3$R$, 4$S$, 5$S$, 6$R$) 5-methoxy-4-[(2R,3R)2-methyl-3-(3-methyl-butyl)-oxiranyl]-1-oxa-spiro[2.5]oct-6-yl ester;" with -- (ID#39)-N-Carbamoyl-(3$R$, 4$S$, 5$S$, 6$R$)-5-methoxy-4-[(2R,3R)-2-methyl-3-(3-methyl-but-2-enyl)-oxiranyl]-1-oxa-spiro[2.5]oct-6-yl ester; --.

Column 80,
Line 1, replace "(ID#26) N-Carbamoyl (3$R$, 4$S$, 5$S$, 6$R$) 5-methoxy-4-[(2R,3R)2-methyl-3-(3-(3-methyl-butyl)-oxiranyl]-1-oxa-spiro[2.5]oct-6-yl ester;" with -- (ID#26)-N--Carbamoyl-(3$R$, 4$S$, 5$S$, 6$R$)-5-methoxy-4-[(2R,3R)-2-methyl-3-(3-methyl-but-2-enyl)-oxiranyl]-1-oxa-spiro[2.5]oct-6-yl ester; --.

Line 4, replace "(ID#27) N-Carbamoyl (3$R$, 4$S$, 5$S$, 6$R$) 5-methoxy-4-[(2R,3R)2-methyl-3-(3-(3-methyl-butyl)-oxiranyl]-1-oxa-spiro[2.5]oct-6-yl ester;" with -- (ID#27)-N--Carbamoyl-(3$R$,4$S$, 5$S$, 6$R$)-5-methoxy-4-[(2R,3R)-2-methyl-3-(3-methyl-but-2-enyl)-oxiranyl]-1-oxa-spiro[2.5]oct-6-yl ester; --.

Line 8, replace "(ID#24)-(2R-{(3$R$, 4$S$, 5$S$, 6$R$) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with
-- (ID#24)-(2R-{(3$R$, 4$S$, 5$S$, 6$R$)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester; --.

UNITED STATES PATENT AND TRADEMARK OFFICE
CERTIFICATE OF CORRECTION

PATENT NO. : 6,919,307 B2
DATED : July 19, 2005
INVENTOR(S) : Gary L. Olson et al.

It is certified that error appears in the above-identified patent and that said Letters Patent is hereby corrected as shown below:

<u>Column 80 (cont'd),</u>
Line 13, replace "(ID#36)-(2*R*-{(3*R*, 4*S*, 5*S*, 6*R*) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester" with -- (ID#36)-(2*R*-{(3*R*, 4*S*, 5*S*, 6*R*)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester --.

Line 17, replace "(ID#37)-(2*R*-{(3*R*, 4*S*, 5*S*, 6*R*) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#37)-(2*R*-{(3*R*, 4*S*, 5*S*, 6*R*) 5-methoxy-4-[(2R,3R)2-methyl-3-(3-methyl-but-2-enyl)-oxiranyl]-1-oxa-spiro[2.5]oct-6-yloxycarbonyl}-amino-3-methyl-butanol) ester; --.

Line 22, replace "(ID#38)-(2*R*-{(3*R*, 4*S*, 5*S*, 6*R*) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#38)-(2*R*-{(3*R*, 4*S*, 5*S*, 6*R*)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester; --.

Line 26, replace "(ID#34)-(2*R*-{(3*R*, 4*S*, 5*S*, 6*R*) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#34)-(2*R*-{(3*R*, 4*S*, 5*S*, 6*R*)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester; --.

Line 31, replace "{2-Methyl-l-[methyl-(1-methyl-piperidin-4-yl)-carbamoyl]-propyl}-carbamic acid 5-methoxy-4-[2-methyl-3-(3-methyl-but-2-enyl)-oxiranyl]-1-oxaspiro[2.5] oct-6-yl ester;" with -- {2-Methyl-1-[methyl-(1-methyl-piperidin-4-yl)-carbamoyl]-propyl}-carbamic acid-5-methoxy-4-[2-methyl-3-(3-methyl-but-2-enyl)-oxiranyl]-1-oxa-spiro[2.5] oct-6-yl ester; --.

Line 35, replace "[1-(2-Dimethylamino-ethylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;" with -- [1-(2-Dimethylamino-ethylcarbamoyl)-2-methyl-propyl]-carbamic acid-5-methoxy-4-[2-methyl-3-(3-methyl-but-2-enyl)-oxiranyl]-1-oxa-spiro[2.5]oct-6-yl ester; --.

Line 40, replace "{1-[(2-Dimethylamino-ethyl)-methyl-carbamoyl]-2-methyl-Propyl}-carbamic acid 5-methoxy-4-[2-methyl-3-(3-methyl-but-2-enyl)-oxiranyl]-1-oxaspiro[2.5] oct-6-yl ester;" with -- {1-[(2-Dimethylamino-ethyl)-methyl-carbamoyl]-2-methyl-propyl}-carbamic acid-5-methoxy-4-[2-methyl-3-(3-methyl-but-2-enyl)-oxiranyl]-1-oxa-spiro[2.5] oct-6-yl ester; --.

UNITED STATES PATENT AND TRADEMARK OFFICE
CERTIFICATE OF CORRECTION

PATENT NO. : 6,919,307 B2
DATED : July 19, 2005
INVENTOR(S) : Gary L. Olson et al.

It is certified that error appears in the above-identified patent and that said Letters Patent is hereby corrected as shown below:

Column 80 (cont'd),
Line 44, replace "[1-(3-Dimethylamino-propylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;" with -- [1-(3-Dimethylamino-propylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester; --.

Line 48, replace "[1-(3-Dimethylamino-2,2-dimethyl-propylcarbamol)-2-methyl-propyl]-carbamic acid 5-methoxy-4-[2-methyl-3-(3-methyl-but-2-enyl)-oxiranyl]-1-oxa-spiro[2.5]oct-6-yl ester;" with -- [1-(3-Dimethylamino-2,2-dimethyl-propylcarbamoyl)-2-methyl-propyl]-carbamic acid-5-methoxy-4-[2-methyl-3-(3-methyl-but-2-enyl)-oxiranyl]-1-oxa-spiro[2.5]oct-6-yl ester; --.

Line 53, replace "[2-Methyl-1-(4-methyl-piperazine-1-carbonyl)-propyl] carbamic acid 5-methoxy-4-(2-methyl-3-(3-methyl-but-2-enyl)-oxiranyl]-1-oxa-spiro[2.5]oct-6-yl ester;" with -- (2-Methyl-1-(4-methyl-piperazine-1-carbonyl)-propyl]-carbamic acid-5-methoxy-4-[2-methyl-3-(3-methyl-but-2-enyl)-oxiranyl]-1-oxa-spiro[2.5]oct-6-yl ester; --.

Line 56, replace "{2-Methyl-1-[2-(1-methyl-pyrrolidin-2-yl)-ethylcarbamoyl]-propyl}-carbamic acid 5-methoxy-4-[2-methyl-3-(3-methyl-but-2-enyl)-oxiranyl]-1-oxa-spiro[2.5]oct-6-yl ester;" with -- {2-Methyl-1-[2-(1-methyl-pyrrolidin-2-yl)-ethylcarbamoyl]-propyl}-carbamic acid-5-methoxy-4-[2-methyl-3-(3-methyl-but-2-enyl)-oxiranyl]-1-oxa-spiro[2.5]oct-6-yl ester; --.

Line 61, replace "[2-Methyl-1-(4-pyrrolidin-1-yl-piperidine-1-carbonyl)-propyl]-carbamic acid 5-methoxy-4-[2-methyl-3-(3-methyl-but-2-enyl)-oxiranyl]-1-oxa-spiro[2.5]oct-6-yl ester; and" with -- [2-Methyl-1-(4-pyrrolidin-1-yl-piperidine-1-carbonyl)-propyl]-carbamic acid-5-methoxy-4-[2-methyl-3-(3-methyl-but-2-enyl)-oxiranyi]-1-oxa-spiro[2.5]oct-6-yl ester; and --.

Line 65, replace "[1-(4-Benzyl-piperazine-1-carbonyl)-2-methyl-propyl]-carbamic acid 5-methoxy-4-[2-methyl-3-(3-methyl-but-2-enyl)-oxiranyl]-1-oxa-spiro[2.5]oct-6-yl ester." with -- [1-(4-Benzyl-piperazine-1-carbonyl)-2-methyl-propyl]-carbamic acid-5-methoxy-4-[2-methyl-3-(3-methyl-but-2-enyl)-oxiranyl]-1-oxa-spiro[2.5]oct-6-yl ester. --.

Column 82,
Line 50, replace "{(3$R$, 4$S$, 5$S$, 6$R$)-5-Methoxy-4-(2$R$, 3$R$)-2-methyl-3-(3-methyl-but-2-enyl)-oxiranyl]-1-oxa-spiro[2.5]oct-6-yloxycarbonylamino}-3-methyl-butyric acid methyl ester;" with -- {(3$R$, 4$S$, 5$S$, 6$R$)-5-Methoxy-4-[(2$R$, 3$R$)-2-methyl-3-(3-methyl-but-2-enyl)-oxiranyl]-1-oxa-spiro[2.5]oct-6-yloxycarbonylamino}-3-methyl-butyric acid methyl ester; --.

UNITED STATES PATENT AND TRADEMARK OFFICE
CERTIFICATE OF CORRECTION

PATENT NO.      : 6,919,307 B2
DATED           : July 19, 2005
INVENTOR(S)     : Gary L. Olson et al.

It is certified that error appears in the above-identified patent and that said Letters Patent is hereby corrected as shown below:

Column 82 (cont'd),
Line 58, replace "2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanaic acid methyl ester;" with -- 2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-4-methyl-pentanoic acid methyl ester; --.

Line 65, replace "(1-Carbamoyl-2-methyl-propyl)-caxbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester;" with -- (1-Carbamoyl-2-methyl-propyl)-carbamic acid-(3R, 4S, 5S, 6R)-5-methoxy-4-[(2R, 3R)-2-methyl-3-(3-methyl-but-2-enyl)-oxiranyl]-1-oxa-spiro[2.5]oct-6-yl ester; --.

Column 83,
Line 8, replace "2-{(3R, 4S, 5S, 6R]-5-Methoxy-4-[2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester;" with -- 2-{(3R, 4S, 5S, 6R )-5-Methoxy-4-[(2R, 3R)-2-methyl-3-(3-methyl-but-2-enyl)-oxiranyl]-1-oxa-spiro[2.5]oct-6-yloxycarbonylamino}-3,3-dimethyl-butyric acid methyl ester; --.

Line 16, replace "2-{(3R, 4S, 5S, 6R)-5-Methoxy-4-[(2R, 3R)-2-methyl-3 (3-methyl-but-2-enyl)-oxiranyl]-1-oxa-spiro[2.5]oct-6-yloxycarbonylamino}-3-methyl-pentanoic acid methyl ester;" with -- 2-{(3R, 4S, 5S, 6R)-5-Methoxy-4-[(2R, 3R)-2-methyl-3-(3-methyl-but-2-enyl)-oxiranyl]-1-oxa-spiro[2.5]oct-6-yloxycarbonylamino}-3-methyl-pentanoic acid methyl ester; --.

Line 30, replace "(ID#31) N-Carbamoyl (3R, 4S, 5S, 6R) 5-methoxy-4-[(2R,3R)2-methyl-3-(3-methyl-butyl)-oxiranyl]-1-oxa-spiro[2.5]oct-6-yl ester;" with -- (ID#31)-N-Carbamoyl-(3R, 4S, 5S, 6R)-5-methoxy-4-[(2R,3R)-2-methyl-3-(3-methyl-butyl)-oxiranyl]-1-oxa-spiro[2.5]oct-6-yl ester; --.

Line 33, replace "(ID#30) N-Carbamoyl (3R, 4S, 5S, 6R) 5-methoxy-4-[(2R,3R)2-methyl-3-(3-methyl-butyl)-oxiranyl]-1-oxa-spiro[2.5]oct-6-yl ester;" with -- (ID#30)-N-Carbamoyl-(3R, 4S, 5S, 6R)-5-methoxy-4-[(2R,3R)-2-methyl-3-(3-methyl-butyl)-oxiranyl]-1-oxa-spiro[2.5]oct-6-yl ester; --.

Line 36, replace "(ID#32) N-Carbamoyl (3R, 4S, 5S, 6R) 5-methoxy-4-[(2R,3R)2-methyl-3-(3-methyl-butyl)-oxiranyl]-1-oxa-spiro[2.5]oct-6-yl ester;" with -- (ID#32)-N-Carbamoyl-(3R, 4S, 5S, 6R)-5-methoxy-4-[(2R,3R)-2-methyl-3-(3-methyl-butyl)-oxiranyl]-1-oxa-spiro[2.5]oct-6-yl ester; --.

UNITED STATES PATENT AND TRADEMARK OFFICE
CERTIFICATE OF CORRECTION

PATENT NO. : 6,919,307 B2
DATED : July 19, 2005
INVENTOR(S) : Gary L. Olson et al.

It is certified that error appears in the above-identified patent and that said Letters Patent is hereby corrected as shown below:

Column 83 (cont'd),
Line 39, replace "(ID#40) N-Carbamoyl ($3R$, $4S$, $5S$, $6R$) 5-methoxy-4-[(2R,3R)2-methyl-3-(3-methyl-butyl)-oxiranyl]-1-oxa-spiro[2.5]oct-6-yl ester;" with -- (ID#40)-N-Carbamoyl-($3R$, $4S$, $5S$, $6R$)-5-methoxy-4-[(2R,3R)-2-methyl-3-(3-methyl-but-2-enyl)-oxiranyl]-1-oxa-spiro[2.5]oct-6-yl ester; --.

Line 43, replace "(ID#39) N-Carbamoyl ($3R$, $4S$, $5S$, $6R$) 5-methoxy-4-[(2R,3R)2-methyl-3-(3-methyl-butyl)-oxiranyl]-1-oxa-spiro[2.5]oct-6-yl ester;" with -- (ID#39)-N-Carbamoyl-($3R$, $4S$, $5S$, 6R)-5-methoxy-4-[(2R,3R)-2-methyl-3-(3-methyl-but-2-enyl)-oxiranyl]-1-oxa-spiro[2.5]oct-6-yl ester; --.

Line 46, replace "(ID#26) N-Carbamoyl ($3R$, $4S$, $5S$, $6R$) 5-methoxy-4-[(2R,3R)2-methyl-3-(3-(3-methyl-butyl)-oxiranyl]-1-oxa-spiro[2.5]oct-6-yl ester;" with -- (ID#26)-N-Carbamoyl-($3R$, $4S$, $5S$, $6R$)-5-methoxy-4-[(2R,3R)-2-methyl-3-(3-methyl-but-2-enyl)-oxiranyl]-1-oxa-spiro[2.5]oct-6-yl ester; --.

Line 49, replace "(ID#27) N-Carbamoyl ($3R$, $4S$, $5S$, $6R$) 5-methoxy-4-[(2R,3R)2-methyl-3-(3-(3-methyl-butyl)-oxiranyl]-1-oxa-spiro[2.5]oct-6-yl ester;" with -- (ID#27)-N-Carbamoyl-($3R$, $4S$, $5S$, $6R$)-5-methoxy-4-[(2R,3R)-2-methyl-3-(3-methyl-but-2-enyl)-oxiranyl]-1-oxa-spiro[2.5]oct-6-yl ester; --.

Line 52, replace "(ID#24)-($2R$-{($3R$, $4S$, $5S$, $6R$) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#24)-($2R$-{($3R$, $4S$, $5S$, $6R$)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester; --.

Line 56, replace "(ID#36)-($2R$-{($3R$, $4S$, $5S$, $6R$) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#36)-($2R$-{($3R$, $4S$, $5S$, $6R$)-5-methoxy-4-[(2R,3R)-2-methyl-3-(3-methyl-but-2-enyl)-oxiranyl)-1-oxa-spiro[2.5]oct-6-yloxycarbonyl}-amino-3-methyl-butanol) ester; --.

Line 60, replace "(ID#37)-($2R$-{($3R$, $4S$, $5S$, $6R$) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with
-- (ID#37)-($2R$-{($3R$, $4S$, $5S$, $6R$)-5-methoxy-4-[(2R,3R)-2-methyl-3-(3-methyl-but-2-enyl)-oxiranyl]-1-oxa-spiro[2.5]oct-6-yloxycarbonyl]-amino-3-methyl-butanol) ester; --.

UNITED STATES PATENT AND TRADEMARK OFFICE
CERTIFICATE OF CORRECTION

PATENT NO.  : 6,919,307 B2
DATED       : July 19, 2005
INVENTOR(S) : Gary L. Olson et al.

It is certified that error appears in the above-identified patent and that said Letters Patent is hereby corrected as shown below:

Column 84,
Line 1, replace "(ID#38)-(2R-{(3R, 4S, 5S, 6R) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#38)-(2R-{(3R, 4S, 5S, 6R)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester; --.

Line 6, replace "(ID#34)-(2R-{(3R, 4S, 5S, 6R) 5-methoxy-4-[(2R,3R)2-methyl-3-(3-(3-methyl-butyl)-oxiranyl]-1-oxa-spiro[2.5]oct-6-yloxycarbonyl} amino-3-methyl-butanol) ester;" with -- (ID#34)-(2R-{(3R, 4S, 5S, 6R)-5-methoxy-4-[(2R,3R)-2-methyl-3-(3-methyl-but-2-enyl)-oxiranyl]-1-oxa-spiro[2.5]oct-6-yloxycarbonyl}-amino-3-methyl-butanol) ester; --.

Line 10, replace "{2-Methyl-1-[methyl-(1-methyl-piperidin-4-yl)-carbamoyl]-propyl}-carbamic acid 5-methoxy-4-[2-methyl-3-(3-methyl-but-2-enyl)-oxiranyl]-1-oxaspiro[2.5] oct-6-yl ester;" with -- {2-Methyl-l-[methyl-(1-methyl-piperidin-4-yl)-carbamoyl]-propyl}-carbamic acid-5-methoxy-4-[2-methyl-3-(3-methyl-but-2-enyl)-oxiranyl]-1-oxa-spiro[2.5] oct-6-yl ester; --.

Line 15, replace "[1-(2-Dimethylamino-ethylcarbamoyl)-2-methylpropyl]-carbamic acid 5-methoxy-4-[2-methyl-3-(3-methyl-but-2-enyl)-oxiranyl]-1-oxa-spiro[2.5]oct-6-yl ester;" with -- [1-(2-Dimethylamino-ethylcarbamoyl)-2-methyl-propyl)-carbamic acid-5-methoxy-4-[2-methyl-3-(3-methyl-but-2-enyl)-oxiranyl]-1-oxa-spiro[2.5]oct-6-yl ester; --.

Line 19, replace "{1-[(2-Dimethylamino-ethyl)-methyl-carbamoyl]-2-methyl-Propyl}-carbamic acid 5-methoxy-4-[2-methyl-3-(3-methyl-but-2-enyl)-oxiranyl]-1-oxaspiro[2.5] oct-6-yl ester;" with -- {1-[(2-Dimethylamino-ethyl)-methyl-carbamoyl]-2-methyl-propyl}-carbamic acid-5-methoxy-4-[2-methyl-3-(3-methyl-but-2-enyl)-oxiranyl]-1-oxa-spiro[2.5] oct-6-yl ester; --.

Line 24, replace "[1-(3-Dimethylamino-propylcarbamoyl)-2-methyl-propyl]-carbamic acid 5-methoxy-4-[2-methyl-3-(3-methyl-but-2-enyl)-oxiranyl]-1-oxa-spiro[2.5]oct-6-yl ester;" with -- [1-(3-Dimethylamino-propylcarbamoyl)-2-methyl-propyl]-carbamic acid-5-methoxy-4-[2-methyl-3-(3-methyl-but-2-enyl)-oxiranyl]-1-oxa-spiro[2.5]oct-6-yl ester; --.

Line 28, replace "[1-(3-Dimethylamino-2,2dimethyl-propylcarbamol)-2-methyl-propyl]-carbamic acid 5-methoxy-4-(2-methyl-3-(3-methyl-but-2-enyl)-oxiranyl]-1-oxaspiro[2.5] oct-6-yl ester;" with -- [1-(3-Dimethylamino-2,2-dimethyl-propylcarbamoyl)-2-methyl-propyl]-carbamic acid-5-methoxy-4-[2-methyl-3-(3-methyl-but-2-enyl)-oxiranyl]-1-oxa-spiro[2.5]oct-6-yl ester; --.

UNITED STATES PATENT AND TRADEMARK OFFICE
CERTIFICATE OF CORRECTION

PATENT NO. : 6,919,307 B2
DATED : July 19, 2005
INVENTOR(S) : Gary L. Olson et al.

It is certified that error appears in the above-identified patent and that said Letters Patent is hereby corrected as shown below:

<u>Column 84 (cont'd),</u>
Line 32, replace "[2-Methyl-1-(4-methyl-piperazine-1-carbonyl)-propyl]carbamic acid 5-methoxy-4-[2-methyl-3-(3-methyl-but-2-enyl)-oxiranyl]-1-oxa-spiro[2.5]oct-6-yl ester;" with -- [2-Methyl-1-(4-methyl-piperazine-1-carbonyl)-propyl]-carbamic acid-5-methoxy-4-(2-methyl-3-(3-methyl-but-2-enyl)-oxiranyl]-1-oxa-spiro[2.5]oct-6-yl ester; --.

Line 36, replace "{2-Methyl-1-[2-(1-methyl-pyrrolidin-2-yl)-ethylcarbamoyl]-propyl}-carbamic acid 5-methoxy-4-[2-methyl-3-(3-methyl-but-2-enyl)-oxiranyl]-1-oxa-spiro[2.5]oct-6-yl ester;" with -- {2-Methyl-1-[2-(1-methyl-pyrrolidin-2-yl)-ethylcarbamoyl]-propyl)-carbamic acid-5-methoxy-4-[2-methyl-3-(3-methyl-but-2-enyl)-oxiranyl]-1-oxa-spiro[2.5]oct-6-yl ester; --.

Line 40, replace "[2-Methyl-1-(4-pyrrolidin-1-yl-piperidne-1-carbonyl)-propyl]-carbamic acid 5-methoxy-4-[2-methyl-3-(3-methyl-but-2-enyl)-oxiranyl]-l-oxa-spiro[2.5]oct-6-yl ester; and" with -- [2-Methyl-1-(4-pyrrolidin-1-yl-piperidne-1-carbonyl)-propyl]-carbamic acid 5-methoxy-4-[2-methyl-3-(3-methyl-but-2-enyl)-oxiranyl]-1-oxa-spiro[2.5]oct-6-yl ester; and --.

Line 44, replace "[1-(4-Benzyl-piperazine-1-carbonyl)-2-methyl-propyl]-carbamic acid 5-methoxy-4-[2-methyl-3-(3-methyl-but-2-enyl)-oxiranyl]-1-oxa-spiro[2.5]oct-6-yl ester." with -- [1-(4-Benzyl-piperazine-1-carbonyl)-2-methyl-propyl]-carbamic acid-5-methoxy-4-[2-methyl-3-(3-methyl-but-2-enyl)-oxiranyl]-1-oxa-spiro[2.5]oct-6-yl ester. --.

Signed and Sealed this

Ninth Day of May, 2006

JON W. DUDAS
*Director of the United States Patent and Trademark Office*